(12) United States Patent
Trautman et al.

(10) Patent No.: US 10,781,477 B2
(45) Date of Patent: Sep. 22, 2020

(54) MOLECULAR DETECTION USING LIGATION AMPLIFICATION

(71) Applicant: ARATOME, LLC, Menlo Park, CA (US)

(72) Inventors: Jay Trautman, Los Altos, CA (US); Gordon Wang, San Jose, CA (US); David Lenzi, Menlo Park, CA (US)

(73) Assignee: ARATOME, LLC, Menlo Park, CA (US)

( * ) Notice: Subject to any disclaimer, the term of this patent is extended or adjusted under 35 U.S.C. 154(b) by 0 days.

(21) Appl. No.: 16/254,926

(22) Filed: Jan. 23, 2019

(65) Prior Publication Data

US 2019/0153522 A1    May 23, 2019

Related U.S. Application Data

(63) Continuation of application No. PCT/US2017/066841, filed on Dec. 15, 2017.

(60) Provisional application No. 62/509,995, filed on May 23, 2017, provisional application No. 62/480,107, filed on Mar. 31, 2017, provisional application No. 62/435,424, filed on Dec. 16, 2016.

(51) Int. Cl.

| | | |
|---|---|---|
| *C12Q 1/68* | (2018.01) | |
| *C07H 21/00* | (2006.01) | |
| *G01N 33/53* | (2006.01) | |
| *C12Q 1/6827* | (2018.01) | |
| *G01N 33/58* | (2006.01) | |
| *G01N 33/533* | (2006.01) | |
| *C12Q 1/44* | (2006.01) | |
| *G01N 33/532* | (2006.01) | |
| *C12Q 1/6816* | (2018.01) | |
| *C07K 16/20* | (2006.01) | |
| *C12Q 1/6818* | (2018.01) | |
| *C12Q 1/6823* | (2018.01) | |
| *C12Q 1/6886* | (2018.01) | |
| *C12Q 1/6888* | (2018.01) | |
| *G01N 1/36* | (2006.01) | |
| *C12Q 1/6809* | (2018.01) | |

(52) U.S. Cl.
CPC ............ *C12Q 1/6827* (2013.01); *C07K 16/20* (2013.01); *C12Q 1/44* (2013.01); *C12Q 1/68* (2013.01); *C12Q 1/6816* (2013.01); *C12Q 1/6818* (2013.01); *C12Q 1/6823* (2013.01); *C12Q 1/6886* (2013.01); *C12Q 1/6888* (2013.01); *G01N 1/36* (2013.01); *G01N 33/532* (2013.01); *G01N 33/533* (2013.01); *G01N 33/582* (2013.01); *G01N 33/585* (2013.01); *C12Q 1/6809* (2013.01); *C12Q 2563/107* (2013.01); *C12Y 605/01001* (2013.01)

(58) Field of Classification Search
CPC ............ C12Q 1/68; C07H 21/00; G01N 33/53
See application file for complete search history.

(56) References Cited

U.S. PATENT DOCUMENTS

| | | | | |
|---|---|---|---|---|
| 5,386,020 A | * | 1/1995 | Seeman | B82Y 10/00 536/23.1 |
| 5,437,977 A | * | 8/1995 | Segev | C12Q 1/6813 435/6.12 |
| 5,635,352 A | * | 6/1997 | Urdea | C12Q 1/6813 435/6.18 |
| 5,854,033 A | * | 12/1998 | Lizardi | C12Q 1/6804 435/91.2 |
| 6,072,044 A | * | 6/2000 | Seeman | C07H 21/02 435/6.15 |
| 6,261,771 B1 | * | 7/2001 | Bohannon | C12Q 1/682 422/129 |
| 6,403,309 B1 | * | 6/2002 | Iris | C12Q 1/6804 435/18 |
| 6,531,283 B1 | | 3/2003 | Kingsmore et al. | |
| 8,309,306 B2 | | 11/2012 | Nolan et al. | |
| 8,927,210 B2 | * | 1/2015 | Adler | C12Q 1/6804 435/6.1 |
| 8,946,389 B2 | | 2/2015 | Gao et al. | |
| 9,376,717 B2 | | 6/2016 | Gao et al. | |
| 2002/0172950 A1 | * | 11/2002 | Kenny | C12Q 1/682 435/6.11 |
| 2004/0214199 A1 | * | 10/2004 | Schwartz | C07H 19/00 435/6.12 |
| 2005/0079520 A1 | | 4/2005 | Wu | |
| 2007/0048759 A1 | * | 3/2007 | Luo | C12Q 1/6816 435/6.19 |
| 2008/0268462 A1 | * | 10/2008 | Kosmeder | C07D 495/04 435/7.1 |
| 2009/0299046 A1 | * | 12/2009 | Crea | C07H 21/04 536/25.3 |

(Continued)

FOREIGN PATENT DOCUMENTS

| | | |
|---|---|---|
| JP | 2001013139 A | 1/2001 |
| WO | WO-02068695 A2 | 9/2002 |

(Continued)

OTHER PUBLICATIONS

Niemeyer et al., Immuno-PCR: high sensitivity detection of proteins by nucleic acid amplification . Trends in Biotechnology 23(4) : 208 (Year: 2005).*

(Continued)

*Primary Examiner* — Ethan C Whisenant
(74) *Attorney, Agent, or Firm* — Wilson Sonsini Goodrich & Rosati

(57) ABSTRACT

Disclosed herein are compositions, kits, methods, and systems for detecting a target molecule in a sample using a detection molecule.

27 Claims, 21 Drawing Sheets

Specification includes a Sequence Listing.

(56) References Cited

U.S. PATENT DOCUMENTS

| | | | |
|---|---|---|---|
| 2009/0311698 A1* | 12/2009 | Huttemann | C12Q 1/682 435/6.14 |
| 2010/0151472 A1* | 6/2010 | Nolan | C12Q 1/682 435/6.1 |
| 2014/0120534 A1* | 5/2014 | Bernitz | C12Q 1/6841 435/6.11 |
| 2014/0194311 A1* | 7/2014 | Gullberg | C12Q 1/6804 506/9 |
| 2015/0368697 A1 | 12/2015 | Samusik et al. | |
| 2016/0083783 A1* | 3/2016 | Blainey | C12Q 1/689 435/5 |
| 2016/0161472 A1* | 6/2016 | Jungmann | G01N 33/5308 506/9 |
| 2016/0186245 A1 | 6/2016 | Luo et al. | |
| 2016/0201117 A1 | 7/2016 | Wu et al. | |
| 2017/0101672 A1 | 4/2017 | Luo et al. | |
| 2017/0107563 A1 | 4/2017 | Samusik et al. | |
| 2017/0307627 A1 | 10/2017 | Wang et al. | |
| 2018/0088112 A1* | 3/2018 | Fan | C12Q 1/68 |
| 2019/0145982 A1* | 5/2019 | Chee | G01N 33/6803 |

FOREIGN PATENT DOCUMENTS

| | | | |
|---|---|---|---|
| WO | WO-03031591 A2 | | 4/2003 |
| WO | WO-2007023390 A2 | | 3/2007 |
| WO | WO 2007/076128 | * | 5/2007 |
| WO | WO-2007076128 A2 | | 7/2007 |
| WO | WO-2014065756 A1 | | 5/2014 |
| WO | WO 2015/0117589 | * | 5/2015 |
| WO | WO-2016057842 A2 | | 4/2016 |

OTHER PUBLICATIONS

Rothemund et al., Folding DNA to create nanoscale shapes and patterns. Nature 440 (7082) : 297-302 (Year: 2006).*

Xu et al., Nonenzymatic autoligation in direct three-color detection of RNA and DNA point mutations. Nature Biotechnology 19 : 148 (Year: 2001).*

Dirks et al., Triggered amplification by hybridization chain reaction. PNAS 101(43) : 15275 (Year: 2004).*

Sarkar et al.,Condensation of oligonucleotides assembled into nicked and gapped duplexes: potential structures for oligonucleotide delivery. Nucleic Acids Research 33(1) : 143-151 (Year: 2005).*

Han et al., Bioconjugate Chemistry 21 : 2190 (Year: 2010).*

Kristina D. Micheva and Stephen J Smith, "Array tomography: A new tool for imaging the molecular architecture and ultrastructure of neural circuits", Neuron. Jul. 5, 2007; 55(1): 25-36.

Sarit S. Agasti et al., "Photocleavable DNA barcode-antibody conjugates allow sensitive and multiplexed protein analysis in single cell", J Am Chem Soc. Nov. 14, 2012; 134(45): 18499-18502.

Afaf H. El-Sagheer et al., "Click Nucleic Acid Ligation: Applications in Biology and Nanotechnology", Accounts of Chemical Research, vol. 45, No. 8, 1258-1267, 2012.

Frederick M. Ausubel et al., Molecular biology, Current Protocols in Molecular Biology, vol. 1, 1-12, 0-555-01747-8, Supplement 78, 1994.

Janssen, K. P. F. et al., "Nucleic acids for ultra-sensitive protein detection", Sensors, 2013, vol. 13, 1353-1384.

Joerger, R. D. et al., "Analyte detection with DNA-labeled antibodies and polymerase chain reaction", Clinical Chemistry, 1995, vol. 41, No. 9, 1371-1377.

Joseph Sambrook et al., "Molecular Cloning: A Laboratory Manual", Cold Spring Harbor Laboratory Press, vol. 1, 1-18, 2001.

Kristina D. Micheva et al., "Array Tomography: Rodent Brain Fixation and Embedding", Cold Spring Harbor Protocols, 1264-1267, 2010.

Malou, N. et al., "Immuno-PCR: a promising ultrasensitive diagnostic method to detect antigens and antibodies", Trends in Microbiology, Jun. 2011, vol. 19, No. 6, 295-302.

Michael Kriegler, Gene Transfer and Expression , A Laboratory Manual, 1-9, 1990.

Nong, R. Y. et al., "DNA-assisted protein detection technologies", Expert Review of Proteomics, 2012, vol. 9, No. 1, 21-32.

PCT/US2017/066841 Written Opinion and International Search Report dated Apr. 20, 2018.

Zhang, H. et al., "Yoctomole detection of proteins using solid phase binding-induced DNA assembly", Methods, 2013, vol. 64, 322-330.

Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.

Bentley, et al. Accurate whole human genome sequencing using reversible terminator chemistry. Nature. Nov. 6, 2008;456(7218):53-9. doi: 10.1038/nature07517.

EP15849036.7 European Search Report and Search Opinion dated Feb. 15, 2018.

International search report with written opinion dated Jan. 29, 2016 for PCT/US2015/054771.

Janssen, et al. Nucleic acids for ultra-sensitive protein detection. Sensors (Basel). Jan. 21, 2013;13(1):1353-84.

Kohl, et al. Ultrafast tissue staining with chemical tags. PNAS, Aug. 25, 2014, vol. 111, No. 36, pp. E3805-E3814.

Li, et al. Photoaffinity labeling of small-moelcular-binding proteins by DNA-templated chemistry. Angewandte International Edition, 2013, vol. 52, Issue 36, pp. 9544-9549.

Micheva, et al. Array tomography: rodent brain fixation and embedding. Cold Spring Harb Protoc. Nov. 1, 2010;2010(11):pdb.prot5523. doi: 10.1101/pdb.prot5523.

Nam, Jwa-Min, et al. Nanoparticle-based bio-barcode for the ultrasensitive detection of proteins. Science, 2003, vol. 301, p. 1884-1886.

U.S. Appl. No. 15/481,141 Non-Final Office Action dated Jan. 23, 2019.

Zhang, et al. Antibody-linked spherical nucleic acids for cellular targeting. JACS, 2012, vol. 134, Issue 40, pp. 16488-16491.

Ki-Cheol Han et al: "An Approach to Multiplexing an Immunosorbent Assay with Antibody-Oligonucleotide Conjugates", Bioconjugate Chemistry, vol. 21, No. 12, Dec. 15, 2010 (Dec. 15, 2010), pp. 2190-2196, XP055159581, ISSN: 1043-1802, DOI: 10.1021/bc100147a.

Supplementary European Search Report dated Jul. 15, 2020 for Application No. EP 17 88 1278, (8 pages).

* cited by examiner

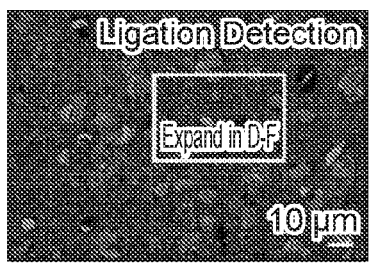
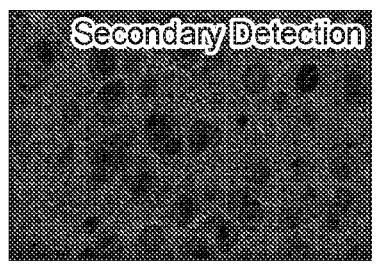
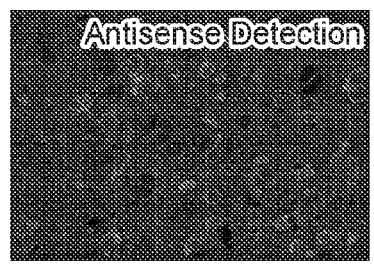
FIG. 7A     FIG. 7B     FIG. 7C
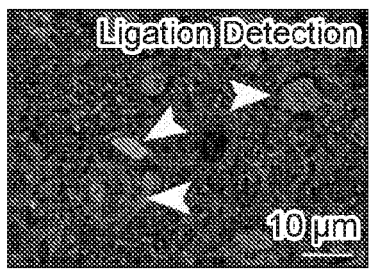
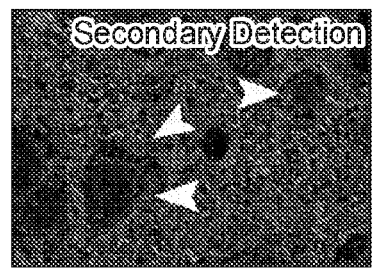
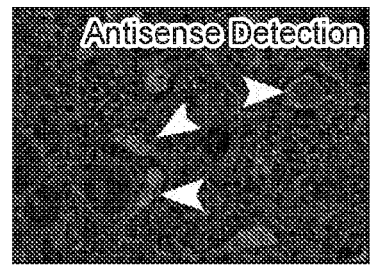
FIG. 7D     FIG. 7E     FIG. 7F
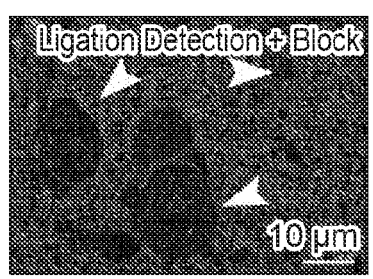
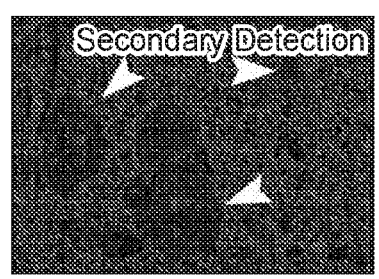
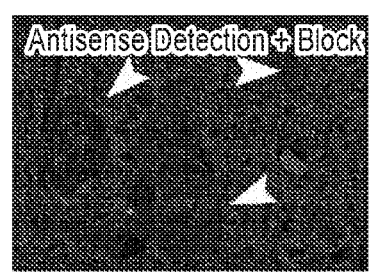
FIG. 7G     FIG. 7H     FIG. 7I
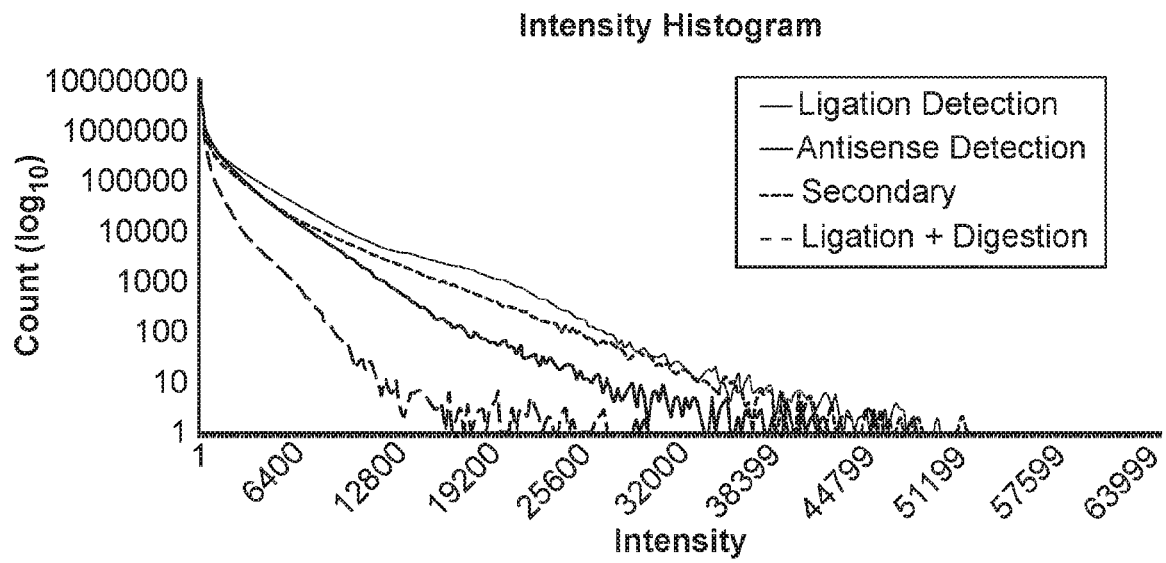
FIG. 7J

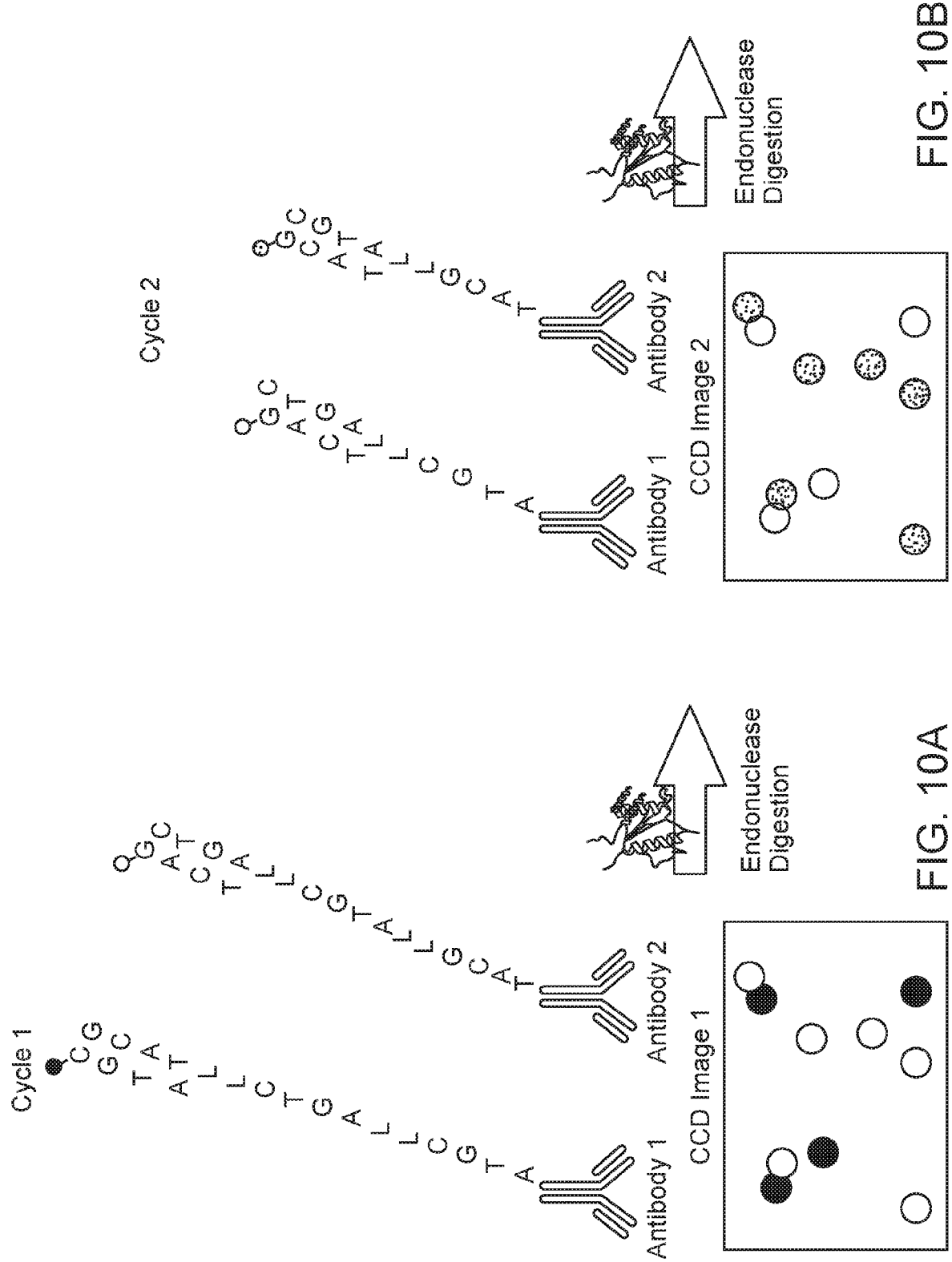

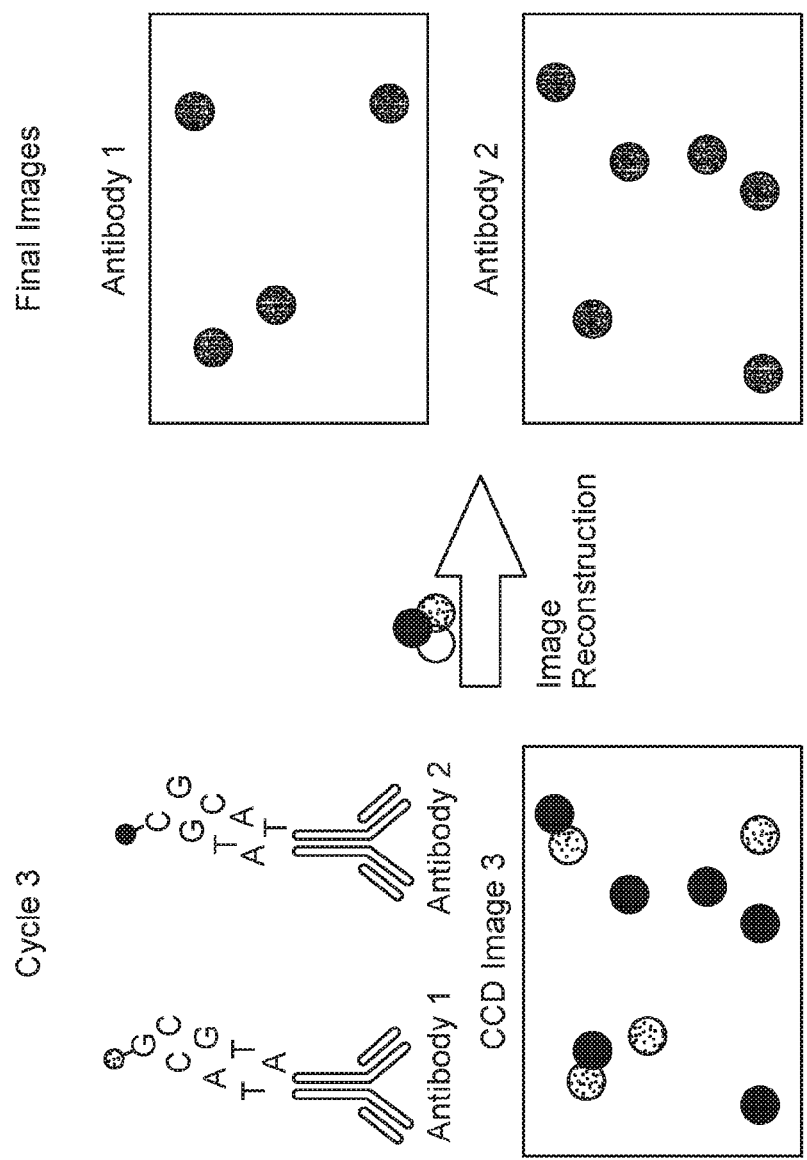

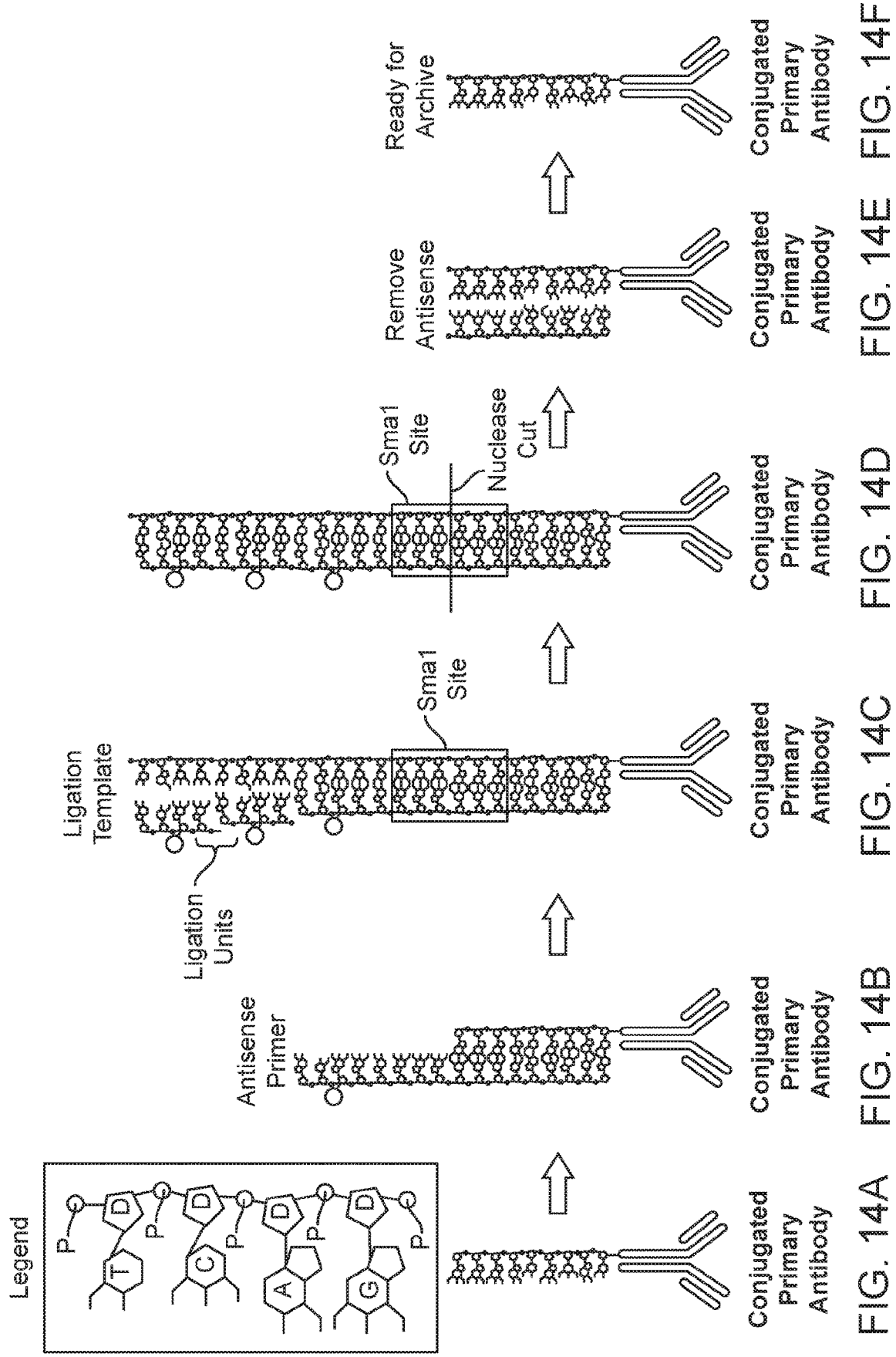

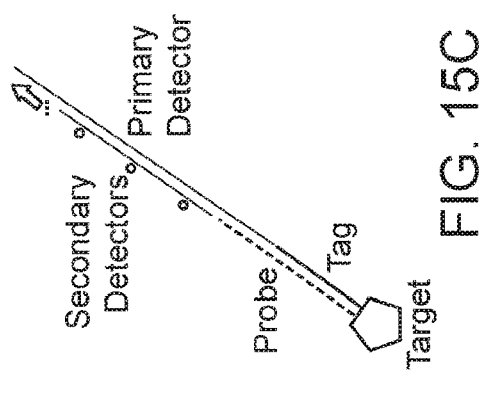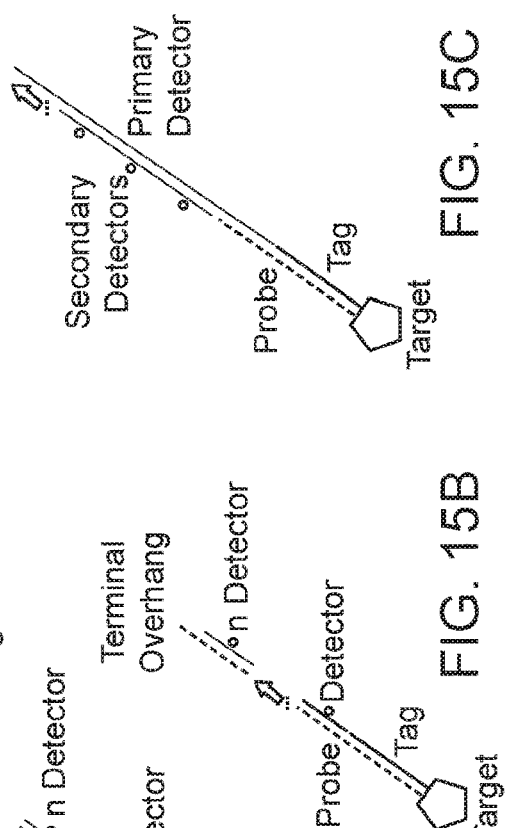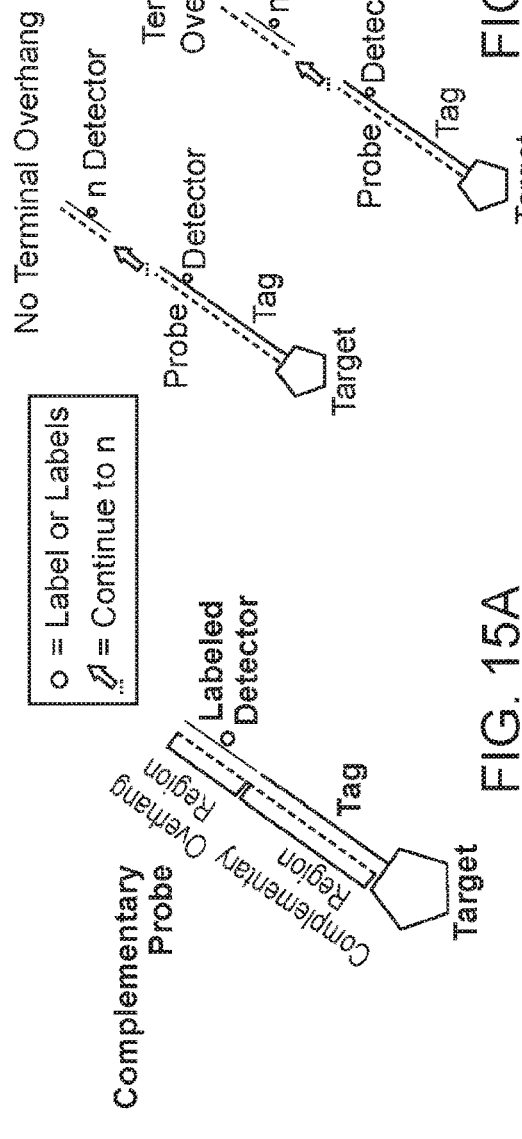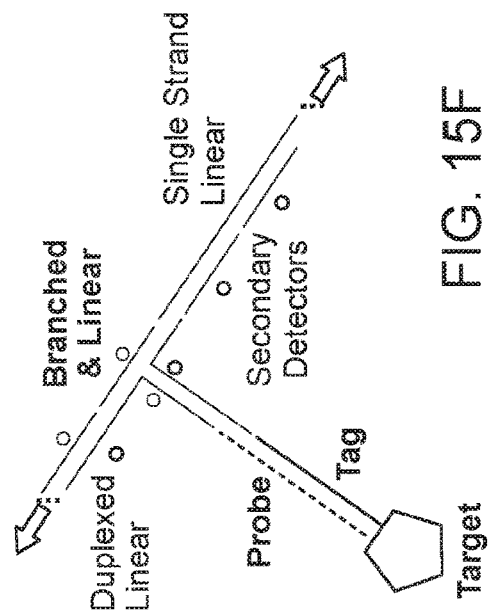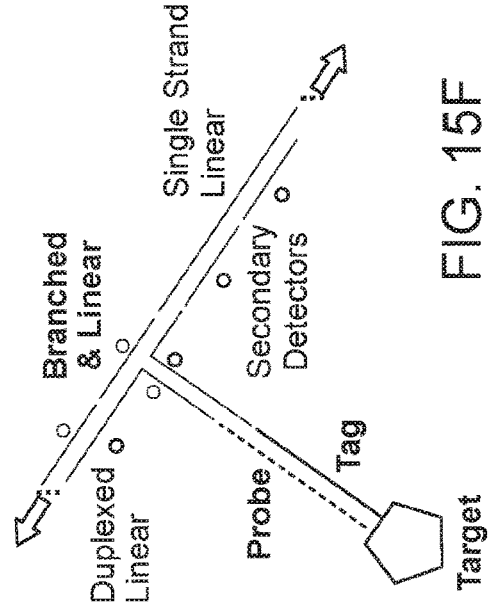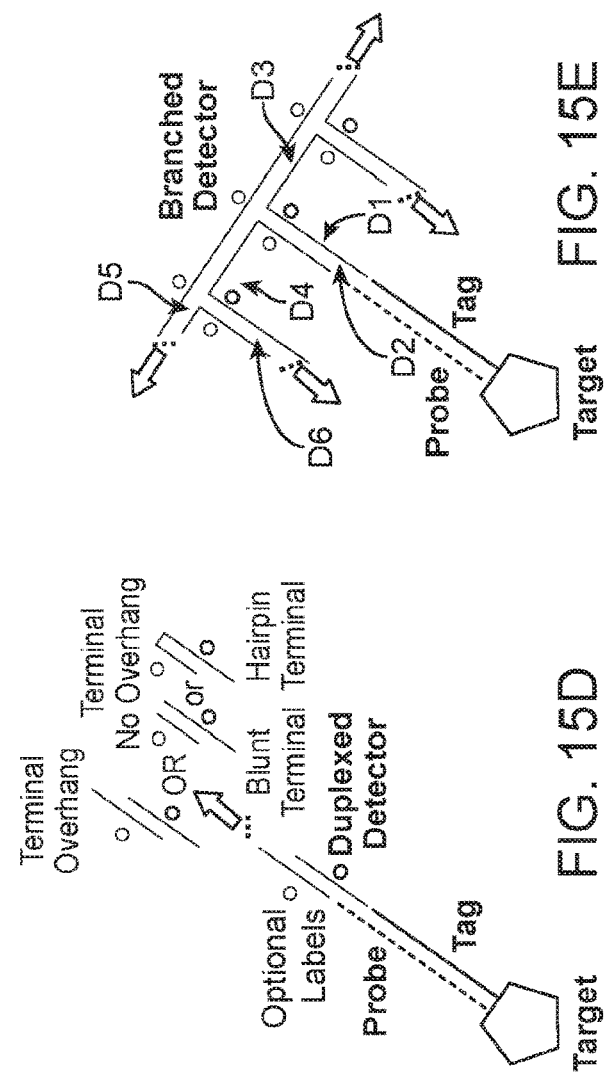

MOLECULAR DETECTION USING LIGATION AMPLIFICATION

CROSS-REFERENCE

This application claims the benefit of U.S. Provisional Application No. 62/435,424, filed Dec. 16, 2016, U.S. Provisional Application No. 62/480,107, filed Mar. 31, 2017, and U.S. Provisional Application No. 62/509,995, filed May 23, 2017, each of which is incorporated herein by reference in its entirety.

STATEMENT AS TO FEDERALLY SPONSORED RESEARCH

This invention was made with government support under NINDS Grant SBIR 1R43NS092180-01 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 31, 2020, is named 47206-702_301_SL.txt and is 1,097 bytes in size.

BACKGROUND

It can be challenging to obtain signal levels comparable to traditional secondary antibody staining, which results on average in a signal on the order of about 15 fluorophores per primary antibody. Multiply labeled antisense oligomers can provide signals on the order of a few fluorophores per primary antibody, but dense labeling of the antisense oligomer may result in quenching among the fluorophores. A ligation amplification method is disclosed herein to provide a higher signal intensity that is comparable to secondary amplification.

SUMMARY

Disclosed herein are compositions, kits, methods, and systems for detecting a target molecule in a sample. In one aspect, disclosed here is a method comprising contacting a target molecule in a sample with a detection couplet, wherein the detection couplet comprises a first nucleic acid and a second nucleic acid, wherein each nucleic acid has a target recognition region and a self-hybridization region, wherein the target recognition region of the first nucleic acid binds a first region of the target molecule, wherein the target recognition region of the second nucleic acid binds a second region of the target molecule, and wherein the self-hybridization region of the first nucleic acid and the self-hybridization region of the second nucleic acid are hybridized to form a double-stranded nucleic acid label.

In some cases, the double-stranded nucleic acid label has at least two consecutive base pairs, for example, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 100, at least 150, at least 200, or at least 250 consecutive base pairs.

In some cases, the double-stranded nucleic acid label has an overhang. In some cases, the overhang has at least 1 unpaired nucleotide, for example, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 100, at least 150, at least 200, or at least 250 unpaired nucleotides.

In some cases, the target molecule is a RNA molecule. In some cases, the target molecule is an mRNA molecule. In some cases, the first nucleic acid and the second nucleic acid are single-stranded DNA. In some cases, the first region and the second region of the target molecule are separated by 2 to 15 nucleotides. In some cases, the first region and the second region of the target molecule are separated by 2 to 5 nucleotides. In some cases, the first region and the second region of the target molecule are separated by 5 to 10 nucleotides. In some cases, the first region and the second region of the target molecule are separated by 10 to 15 nucleotides. In some cases, the first region and the second region of the target molecule are separated by 15 to 20 nucleotides.

In some cases, the method further comprises fixing the detection couplet to the sample using a crosslinker. In some cases, the first nucleic acid or the second nucleic acid has a free amine (—NH2) modification. In some cases, the fixing the detection couplet comprises contacting the detection couplet with an amine-specific crosslinker.

In some cases, the overhang comprises one nucleotide. In some cases, the overhang comprises a plurality of nucleotides. In some cases, the overhang comprises at least about 2, 3, 4, 5, 10, 15, 20, 25, 30, 40, 50, 60, 70, 80, 90, 100, 150, 200, 250, 300, 350, 400, 450, or 500 of nucleotides. In some cases, the method further comprises contacting the double-stranded nucleic acid label with a DNA ligase. In some cases, the method further comprises contacting the double-stranded nucleic acid label with at least one detection label. In some cases, the at least one detection label is a double-stranded nucleic acid with an overhang that is complementary to the overhang of the double-stranded nucleic acid label. In some cases, the at least one detection label is a single-stranded nucleic acid that is complementary to the overhang of the double-stranded nucleic acid label. In some cases, the at least one detection label comprises a plurality of detection labels. In some cases, the double-stranded nucleic acid label and the at least one detection label are ligated using the DNA ligase. In some cases, the at least one detection label comprises at least 5, 10, 15, 20, 25, or 30 detection labels. In some cases, the at least one detection label comprises a cleavable linker. In some cases, the at least one detection label does not comprise a cleavable linker.

In some cases, the at least one detection label comprises a detection tag. In some cases, the at least one detection label comprises a plurality of detection tags. In some cases, the detection tag comprises a quantum dot. In some cases, the detection tag comprises a fluorophore. In some cases, the fluorophore comprises coumarin, rhodamine, xanthene, fluorescein, or cyanine. In some cases, the method comprises detecting the detection tag, thereby detecting the presence of the target molecule in the sample. In some cases, the method comprises contacting the sample with a plurality of detection couplets. In some cases, each of the plurality of detection couplets binds a different target molecule.

In some cases, the sample is an intact tissue sample. In some cases, the method comprises embedding the intact tissue sample in a resin such that the intact tissue sample can be sliced into sections of thickness between 20 and 1000 nm. In some cases, the intact tissue sample is a bone marrow tissue sample, a gastrointestinal tract tissue sample, a lung tissue sample, a liver tissue sample, a prostate tissue sample, a nervous system tissue sample, a urogenital system tissue sample, a brain tissue sample, a breast tissue sample, a muscle tissue sample, or a skin tissue sample. In some cases, the method comprises dehydration of the intact tissue sample. In some cases, the method does not comprise dehydration of the intact tissue sample. In some cases, the method of comprises diagnosing a condition or disease associated with the presence of the target molecule in the sample. In some cases, the condition or disease is a kidney disease, an infectious disease, a metabolic disease, a pre-cancerous condition, a cancerous condition, or a brain disorder. In some cases, the sample is a paraffin-embedded tissue sample. In some cases, the sample is a formalin-fixed paraffin-embedded (FFPE) tissue sample.

In some cases, the method further comprises contacting the double-stranded nucleic acid label with a third nucleic acid, wherein the third nucleic acid comprises a sequence that is complementary to a sequence of the first nucleic acid, a sequence of the second nucleic acid, or both. In one example, the third nucleic acid comprises a sequence that is complementary to a sequence of the first nucleic acid. In one example, the third nucleic acid comprises a sequence that is complementary to a sequence of the second nucleic acid. In one example, the third nucleic acid comprises a sequence that is complementary to a sequence of the first nucleic acid and a sequence of the second nucleic acid. In some cases, the third nucleic acid binds to the sequence of the first nucleic acid, the sequence of the second nucleic acid, or both. In one example, the third nucleic acid binds to the sequence of the first nucleic acid. In one example, the third nucleic acid binds to the sequence of the second nucleic acid. In one example, the third nucleic acid binds to the sequence of the first nucleic acid and the sequence of the second nucleic acid.

In some cases, the first nucleic acid and the second nucleic acid in the double-stranded nucleic acid label each has at least one unpaired nucleotide. In some cases, the first nucleic acid and the second nucleic acid in the double-stranded nucleic acid label each has at least 1 unpaired nucleotide, for example, at least 2, at least 3, at least 4, at least 5, at least 6, at least 7, at least 8, at least 9, at least 10, at least 11, at least 12, at least 13, at least 14, at least 15, at least 20, at least 25, at least 30, at least 35, at least 40, at least 45, at least 50, at least 100, at least 150, at least 200, or at least 250 unpaired nucleotides. In some cases, the third nucleic acid comprises a sequence that is complementary to an unpaired sequence of the first nucleic acid, an unpaired sequence of the second nucleic acid, or both. In some cases, the third nucleic acid comprises a sequence that is complementary to the entire unpaired sequence of the first nucleic acid. In some cases, the third nucleic acid comprises a sequence that is complementary to the entire unpaired sequence of the second nucleic acid. In some cases, the third nucleic acid comprises a first sequence that is complementary to the entire unpaired sequence of the first nucleic acid and a second sequence that is complementary to the entire unpaired sequence of the second nucleic acid and.

In some cases, the third nucleic acid binds to the sequence of the first nucleic acid and the sequence of the second nucleic acid, thereby creating a multi-way branch. In some cases, the multi-way branch is a n-way branch, wherein the n-way branch comprises n single stranded nucleic acid that are linked together to form a nucleic acid structure. The nucleic acid structure can have n terminals and/or n overhangs. For example, the multi-way branch can be a three-way branch, wherein the three-way branch comprises three single stranded nucleic acid that are linked together to form a nucleic acid structure that have three terminals and/or three overhangs (see e.g., FIG. 17A-C and FIG. 16C). In some cases, the three-way branch comprises at least two overhangs. In some cases, at least two of said at least two overhangs comprise same sequence or unique sequences. In some cases, at least two of said at least two overhangs comprise complementary sequences.

In some cases, the method further comprises contacting the third nucleic acid with a fourth nucleic acid, wherein the fourth nucleic acid comprises a sequence that is complementary to a sequence of the first nucleic acid, a sequence of the second nucleic acid, a sequence of the third nucleic acid, or any combination thereof. In some cases, the fourth nucleic acid binds to the sequence of the third nucleic acid and the sequence of the first or second nucleic acid, thereby creating a four-way branch (see e.g., FIG. 16C). In some cases, the four-way branch comprises four single stranded nucleic acid that are linked together to form a nucleic acid structure that have four terminals and/or four overhangs. In some cases, the four-way branch comprises at least three overhangs. In some cases, at least two of the at least three overhangs comprise same sequence or unique sequences. In some cases, at least two of the at least three overhangs comprise complementary sequences.

In some cases, the method further comprises contacting at least one of the overhangs with a detection label. In some cases, the method further comprises contacting the third nucleic acid with a detection label. In some cases, the method further comprises contacting the fourth nucleic acid with a detection label. In some cases, the detection label comprises a multi-way branch. In some cases, the multi-way branch is a three-way branch or a four-way branch. In some cases, the detection label comprises an overhang that is complementary to the at least one of the overhangs. In some cases, the detection label is linked to the at least one of the overhangs by direct hybridization, enzymatic ligation, or chemical ligation.

In another aspect, disclosed herein is a method comprising contacting a target molecule in a sample with a detection molecule and an antisense oligomer, wherein the detection molecule comprises at least one ligand that binds the target molecule, wherein the at least one ligand is linked to a single-stranded nucleic acid, and wherein the single-stranded nucleic acid is hybridized with the antisense oligomer to form a double-stranded nucleic acid label with an overhang. In some cases, the detection molecule or antisense comprises at least 3 nucleotides, for example at least 5, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, or at least 500 nucleotides. In some cases, the detection molecule or the antisense comprises no more than 500 nucleotides, for example no more than 5, no more than 10, no more than 15, no more than 20, no more than 25, no more than 30, no more than 35, no more than 40, no more than 45, no more than 50, no more than 60, no more than 70, no more than 80, no more than 90, no more than 100, no more than 150, no more than 200, no more than 250, no more than 300, no more than 350, no more than 400, no more than 450, or no more than 500 nucleotides. In some cases, the detection molecule or the antisense comprises about 3-500 nucleotides, for example, from about 3-500, about 3-400, about 3-300, about 3-200, about 3-100, about 3-50, about 3-20, about 3-10, about 10-500, about 10-400, about 10-300, about 10-200, about 10-100, about 10-50, about 10-20, about 20-500, about 20-400, about 20-300, about 20-200, about 20-100, about 20-50, about 50-500, about 50-400, about 50-300, about 50-200, about 50-100, about 100-500, about 100-400, about 100-300, about 100-200, about 200-500, about 200-400, about 200-300, about 300-500, about 300-400, or about 400-500 nucleotides. For instance, the detection molecule or antisense can comprise about 3-150 nucleotides.

In some cases, the ligand is an antibody. In some cases, the target molecule is a protein. In some cases, the overhang comprises one nucleotide. In some cases, the overhang comprises a plurality of nucleotides. In some cases, the method further comprises contacting the double-stranded nucleic acid label with a DNA ligase. In some cases, the method further comprises contacting the double-stranded nucleic acid label with at least one detection label. In some cases, the at least one detection label is a double-stranded nucleic acid with an overhang that is complementary to the overhang of the double-stranded nucleic acid label. In some cases, the at least one detection label is a plurality of detection labels. In some cases, the at least one detection label is a single-stranded nucleic acid that is complementary to the overhang of the double-stranded nucleic acid label. In some cases, the at least one detection label comprises a plurality of detection labels. In some cases, the at least one detection label comprises at least 5, 10, 15, 20, 25, or 30 detection labels. In some cases, the at least one detection label comprises a cleavable linker. In some cases, the at least one detection label does not comprise a cleavable linker.

In some cases, the at least one detection label comprises a detection tag. In some cases, the at least one detection label comprises a plurality of detection tags. In some cases, the detection tag comprises a quantum dot. In some cases, the detection tag comprises a fluorophore. In some cases, the fluorophore comprises coumarin, rhodamine, xanthene, fluorescein, or cyanine. In some cases, the method comprises detecting the detection tag, thereby detecting the presence of the target molecule in the sample. In some cases, the method comprises contacting the sample with a plurality of detection molecules. In some cases, each of the plurality of detection molecules binds a different target molecule.

In some cases, the detection label comprises at least 3 nucleotides, for example at least 5, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, or at least 500 nucleotides. In some cases, the detection label comprises no more than 500 nucleotides, for example no more than 5, no more than 10, no more than 15, no more than 20, no more than 25, no more than 30, no more than 35, no more than 40, no more than 45, no more than 50, no more than 60, no more than 70, no more than 80, no more than 90, no more than 100, no more than 150, no more than 200, no more than 250, no more than 300, no more than 350, no more than 400, no more than 450, or no more than 500 nucleotides. In some cases, the detection label comprises about 3-500 nucleotides, for example, from about 3-500, about 3-400, about 3-300, about 3-200, about 3-100, about 3-50, about 3-20, about 3-10, about 10-500, about 10-400, about 10-300, about 10-200, about 10-100, about 10-50, about 10-20, about 20-500, about 20-400, about 20-300, about 20-200, about 20-100, about 20-50, about 50-500, about 50-400, about 50-300, about 50-200, about 50-100, about 100-500, about 100-400, about 100-300, about 100-200, about 200-500, about 200-400, about 200-300, about 300-500, about 300-400, or about 400-500 nucleotides. For instance, the detection label can comprise about 3-150 nucleotides.

In some cases, the sample is an intact tissue sample. In some cases, the method comprises embedding the intact tissue sample in a resin such that the intact tissue sample can be sliced into sections of thickness between 20 and 1000 nm. In some cases, the intact tissue sample is a bone marrow tissue sample, a gastrointestinal tract tissue sample, a lung tissue sample, a liver tissue sample, a prostate tissue sample, a nervous system tissue sample, a urogenital system tissue sample, a brain tissue sample, a breast tissue sample, a muscle tissue sample, or a skin tissue sample. In some cases, the method comprises dehydration of the intact tissue sample. In some cases, the method does not comprise dehydration of the intact tissue sample. In some cases, the method of comprises diagnosing a condition or disease associated with the presence of the target molecule in the sample. In some cases, the condition or disease is a kidney disease, an infectious disease, a metabolic disease, a precancerous condition, a cancerous condition, or a brain disorder.

In some cases, the target molecule comprises a component in a gene-editing assay. In some cases, the gene-editing assay is a CRISPR assay. In some cases, the gene-editing assay is a CRISPR/Cas assay. In some cases, the gene-editing assay is an NgAgo assay. In some cases, the component comprises a Cas nuclease, a target DNA, a DNA-targeting RNA, a trans-activating crRNA (tracrRNA), a donor repair template, or any combination thereof. In some cases, the component comprises a Cas nuclease. In some cases, the component comprises a Cas9 nuclease. In some cases, the target molecule comprises a cellular molecule. In some cases, the target molecule comprises a cell surface molecule. In some cases, the target molecule comprises a carbohydrate, a lipid, a protein, or a nucleic acid. In some cases, the target molecule comprises a protein. In some cases, the protein comprise a cytoskeletal protein, an extracellular matrix protein, a plasma protein, a coagulation factor, an acute phase protein, a hemoprotein, a cell adhesion, a transmembrane transport protein, an ion channel, a synport/antiport protein, a hormone, a growth factor, a receptor, a DNA-binding protein, a RNA-binding protein, a transcription regulatory protein, an immune system protein, a nutrient storage or transport protein, a chaperone protein, an enzyme, or any combination thereof. In some cases, the target molecule comprises a nucleic acid. In some cases, the nucleic acid comprises an mRNA, a tRNA, a rRNA, a snRNA, an non-coding RNA molecule, or any combination thereof.

In some cases, the method further comprises contacting the double-stranded nucleic acid label with a detection label. In some cases, the detection label comprises a multi-way branch. In some cases, the multi-way branch is a three-way branch or a four-way branch. In some cases, the detection label comprises an overhang that is complementary to the overhang of the double-stranded nucleic acid label. In some cases, the detection label is linked to the overhang of the double-stranded nucleic acid label by direct hybridization, enzymatic ligation, or chemical ligation.

In some cases, the method further comprises contacting the detection label with a second detection label. In some cases, the second detection label comprises a multi-way branch. In some cases, the multi-way branch is a three-way branch or a four-way branch. In some cases, the second detection label comprises an overhang that is complementary to the overhang of the detection label.

In another aspect, disclosed herein is a composition, comprising: a detection couplet, wherein the detection couplet comprises a first nucleic acid and a second nucleic acid, wherein each nucleic acid has a target recognition region and a self-hybridization region, wherein the target recognition region of the first nucleic acid binds a first region of a target molecule, wherein the target recognition region of the second nucleic acid binds a second region of the target molecule, and wherein the self-hybridization region of the first nucleic acid and the self-hybridization region of the second nucleic acid are hybridized to form a double-stranded nucleic acid label. In some cases, the double-stranded nucleic acid label has at least two consecutive base pairs, for example, at least 2, at least 3, at least 4, at least 5, at least 6, at least 7, at least 8, at least 9, at least 10, at least 11, at least 12, at least 13, at least 14, or at least 15 consecutive base pairs. In some cases, the double-stranded nucleic acid label has an overhang. In some cases, the overhang comprises one nucleotide. In some cases, the overhang comprises a plurality of nucleotides. In some cases, the overhang comprises at least 5, 10, 15, 20, 25, or 30 nucleotides. In some cases, the overhang has at least 1 unpaired nucleotide, for example, at least 2, at least 3, at least 4, at least 5, at least 6, at least 7, at least 8, at least 9, at least 10, at least 11, at least 12, at least 13, at least 14, or at least 15 unpaired nucleotides. In some cases, the target molecule is an mRNA molecule. In some cases, the first nucleic acid and the second nucleic acid are single-stranded DNA. In some cases, each of the first nucleic acid and the second nucleic acid has a free amine (—NH2) modification. In some cases, the composition further comprises a DNA ligase. In some cases, the composition further comprises at least one detection label. In some cases, the at least one detection label is a double-stranded nucleic acid with an overhang that is complementary to the overhang of the double-stranded nucleic acid label. In some cases, the at least one detection label is a single-stranded nucleic acid that is complementary to the overhang of the double-stranded nucleic acid label. In some cases, the at least one detection label comprises a plurality of detection labels. In some cases, the at least one detection label comprises at least 5, 10, 15, 20, 25, or 30 detection labels. In some cases, the at least one detection label does not comprise a cleavable linker. In some cases, the at least one detection label comprises a cleavable linker. In some cases, the at least one detection label comprises a detection tag. In some cases, the at least one detection label comprises a plurality of detection tags. In some cases, the detection tag comprises a quantum dot. In some cases, the detection tag comprises a fluorophore. In some cases, the fluorophore comprises coumarin, rhodamine, xanthene, fluorescein, or cyanine. In some cases, the composition comprises a plurality of detection couplets. In some cases, each of the plurality of detection couplets binds a different target molecule.

In another aspect, the composition further comprises a third nucleic acid, wherein the third nucleic acid comprises a sequence that is complementary to a sequence of the first nucleic acid, a sequence of the second nucleic acid, or both. In some cases, the third nucleic acid comprises a sequence that is complementary to a sequence of the first nucleic acid. In some cases, the third nucleic acid comprises a sequence that is complementary to a sequence of the second nucleic acid. In some cases, the third nucleic acid comprises a sequence that is complementary to a sequence of the first nucleic acid and a sequence of the second nucleic acid. In some cases, the third nucleic acid binds to the sequence of the first nucleic acid and the sequence of the second nucleic acid, thereby creating a multi-way branch. In some cases, the multi-way branch is a three-way branch. In some cases, the three-way branch comprises at least two overhangs.

In some cases, the composition further comprises a fourth nucleic acid, wherein the fourth nucleic acid comprises a sequence that is complementary to a sequence of the first nucleic acid, a sequence of the second nucleic acid, a sequence of the third nucleic acid, or any combination thereof. In some cases, the fourth nucleic acid binds to the sequence of the third nucleic acid and the sequence of the first or second nucleic acid, thereby creating a four-way branch. In some cases, the four-way branch comprises at least three overhangs. In some cases, at least two of the overhangs comprise same sequence or unique sequences. In some cases, at least two of said overhangs comprise complementary sequences.

In some cases, the composition further comprises a detection label. In some cases, the detection label comprises a multi-way branch. In some cases, the multi-way branch is a three-way branch or a four-way branch. In some cases, the detection label comprises an overhang that is complementary to the at least one of the overhangs.

In another aspect, disclosed herein is a composition, comprising: a detection molecule and an antisense oligomer, wherein the detection molecule comprises at least one ligand that binds a target molecule. wherein the at least one ligand is linked to a single-stranded nucleic acid, and wherein the single-stranded nucleic acid is hybridized to the antisense oligomer to form a double-stranded nucleic acid label with an overhang. In some cases, the ligand is an antibody. In some cases, the target molecule is a protein. In some cases, the overhang comprises one nucleotide. In some cases, the overhang comprises a plurality of nucleotides. In some cases, the overhang comprises at least 5, 10, 15, 20, 25, or 30 nucleotides. In some cases, the composition further comprises a DNA ligase. In some cases, the composition further comprises at least one detection label. In some cases, the at least one detection label is a double-stranded nucleic acid with an overhang that is complementary to the overhang of the double-stranded nucleic acid label. In some cases, the at least one detection label is a single-stranded nucleic acid that is complementary to the overhang of the double stranded nucleic acid label. In some cases, the at least one detection label comprises at least 5, 10, 15, 20, 25, or 30 detection labels. In some cases, the at least one detection label comprises a cleavable linker. In some cases, the at least one detection label does not comprise a cleavable linker. In some cases, the at least one detection label comprises a detection tag. In some cases, the at least one detection label comprises a plurality of detection tags. In some cases, the detection tag comprises a quantum dot. In some cases, the detection tag comprises a fluorophore. In some cases, the fluorophore comprises coumarin, rhodamine, xanthene, fluorescein, or cyanine. In some cases, the composition comprises a plurality of detection molecules. In some cases, each of the plurality of detection molecules binds a different target molecule.

In some cases, the target molecule comprises a component in a gene-editing assay. In some cases, the gene-editing assay is a CRISPR assay. In some cases, the gene-editing assay is a CRISPR/Cas assay. In some cases, the gene-editing assay is an NgAgo assay. In some cases, the component comprises a Cas nuclease, a target DNA, a DNA-targeting RNA, a trans-activating crRNA (tracrRNA), a donor repair template, or any combination thereof. In some cases, the component comprises a Cas nuclease. In some cases, the component comprises a Cas9 nuclease. In some cases, the target molecule comprises a cellular molecule. In some cases, the target molecule comprises a cell surface molecule. In some cases, the target molecule comprises a carbohydrate, a lipid, a protein, or a nucleic acid. In some cases, the target molecule comprises a protein. In some cases, the protein comprise a cytoskeletal protein, an extracellular matrix protein, a plasma protein, a coagulation factor, an acute phase protein, a hemoprotein, a cell adhesion, a transmembrane transport protein, an ion channel, a synport/antiport protein, a hormone, a growth factor, a receptor, a DNA-binding protein, a RNA-binding protein, a transcription regulatory protein, an immune system protein, a nutrient storage or transport protein, a chaperone protein, an enzyme, or any combination thereof. In some cases, the target molecule comprises a nucleic acid. In some cases, the nucleic acid comprises an mRNA, a tRNA, a rRNA, a snRNA, an non-coding RNA molecule, or any combination thereof.

In some cases, the at least one detection label comprises an overhang that is complementary to the overhang of the double-stranded nucleic acid label. In some cases, the at least one detection label comprises a multi-way branch. In some cases, the multi-way branch is a three-way branch or a four-way branch. In some cases, the at least one detection label is linked to the overhang of the double-stranded nucleic acid label by direct hybridization, enzymatic ligation, or chemical ligation.

In some cases, the composition further comprises a second detection label. In some cases, the second detection label comprises an overhang that is complementary to said overhang of said at least one detection label. In some cases, the second detection label comprises a multi-way branch. In some cases, the multi-way branch is a three-way branch or a four-way branch.

In another aspect, disclosed herein is a kit, which can be used in methods described above, comprising: a detection couplet, wherein the detection couplet comprises a first nucleic acid and a second nucleic acid, wherein each nucleic acid has a target recognition region and a self-hybridization region, wherein the target recognition region of the first nucleic acid binds a first region of a target molecule, wherein the target recognition region of the second nucleic acid binds a second region of the target molecule, and wherein the self-hybridization region of the first nucleic acid and the self-hybridization region of the second nucleic acid are hybridized to form a double-stranded nucleic acid label; and a first reagent for use when contacting the detection couplet with the target molecule. In some cases, the double-stranded nucleic acid label has an overhang. In some cases, the kit comprises one or more compositions described above.

In another aspect, disclosed herein is a kit, which can be used in methods described above, comprising: a detection molecule and an antisense oligomer, wherein the detection molecule comprises at least one ligand that binds a target molecule, wherein the at least one ligand is linked to a single-stranded nucleic acid, and wherein the single-stranded nucleic acid is hybridized to the antisense oligomer to form a double-stranded nucleic acid label with an overhang; and a first reagent for use when contacting the detection couplet with the target molecule.

In some cases, the kit further comprises a second reagent for use in detection of the target molecule.

In some cases, the target molecule comprises a component in a gene-editing assay. In some cases, the gene-editing assay is a CRISPR assay. In some cases, the gene-editing assay is a CRISPR/Cas assay. In some cases, the gene-editing assay is an NgAgo assay. In some cases, the component comprises a Cas nuclease, a target DNA, a DNA-targeting RNA, a trans-activating crRNA (tracrRNA), a donor repair template, or any combination thereof. In some cases, the component comprises a Cas nuclease. In some cases, the component comprises a Cas9 nuclease. In some cases, the target molecule comprises a cellular molecule. In some cases, the target molecule comprises a cell surface molecule. In some cases, the target molecule comprises a carbohydrate, a lipid, a protein, or a nucleic acid. In some cases, the target molecule comprises a protein. In some cases, the protein comprise a cytoskeletal protein, an extracellular matrix protein, a plasma protein, a coagulation factor, an acute phase protein, a hemoprotein, a cell adhesion, a transmembrane transport protein, an ion channel, a synport/antiport protein, a hormone, a growth factor, a receptor, a DNA-binding protein, a RNA-binding protein, a transcription regulatory protein, an immune system protein, a nutrient storage or transport protein, a chaperone protein, an enzyme, or any combination thereof. In some cases, the target molecule comprises a nucleic acid. In some cases, the nucleic acid comprises an mRNA, a tRNA, a rRNA, a snRNA, an non-coding RNA molecule, or any combination thereof.

In some cases, the kit comprises any of the compositions disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

FIGS. 7A-7J illustrate the max projection of DNA-tagged acetylated tubulin from 10 (70 nm) sections. FIG. 7A illustrates DNA-labeled primary visualized via ligation oligomerization. FIG. 7B illustrates the same DNA-primary visualized by traditional fluorescent secondary in the same tissue sections. FIG. 7C illustrates DNA-labeled primary visualized with fluorescently labeled antisense oligomers in the same tissue as FIG. 4A and FIG. 4B. FIGS. 7 D-7F illustrate the close-up views of FIGS. 7A-7C (as highlighted by yellow box). FIG. 7D illustrates point to off-target ligation visualization of nucleus, which are absent in FIG. 7E (white arrowheads). FIG. 7F illustrates antisense detection also incurred off-target signal, although the nucleus has lesser labeling. FIGS. 7G-7I illustrate in different tissue, DNA-labeled synapsin antibody can be visualized post phosphatase and sonicated DNA block. FIG. 7G illustrates significant decrease in nuclear labeling, bringing off-target labeling (white arrowheads) on par with secondary detection FIG. 7H (white arrowheads). FIG. 7I illustrates the sonicated DNA block also improved antisense detection noise. FIG. 7J illustrates the superimposed intensity histograms of each method on logarithmic scale.

FIGS. 10A-D illustrate an example of fast detection of multiplexed antigens using tag sequencing. FIG. 10A illustrates cycle 1 of the sequential detection of oligomer modules followed by removal of the fluorescently labeled oligomers by restriction endonuclease cleavage.

FIG. 10B illustrates cycle 2 of the sequential detection of oligomer modules followed by removal of the fluorescently labeled oligomers by restriction endonuclease cleavage. FIG. 10C illustrates cycle 3 of the sequential detection of oligomer modules followed by removal of the fluorescently labeled oligomers by restriction endonuclease cleavage. FIG. 10D illustrates using the color combinations generated across imaging cycles, final images for each antigen can be reconstructed.

FIG. 13A illustrates fluorescence amplification through ligation oligomerization method. Small DNA duplexes with fluorophores are sequentially ligated to a growing strand through specific recognition of sticky ends, leading to amplification of florescence signal. FIG. 13B illustrates fluorescence amplification through template oligomerization. Fluorescence amplification occurs through the sequential hybridization and ligation of single stranded small DNA with fluorophores, leading to amplification of fluorescence signal.

FIGS. 14A-14F illustrate DNA-antibody archival immunohistochemistry for archival imaging. FIG. 14A illustrates DNA conjugated primary on antigen. FIG. 14B illustrates antisense detection of conjugate. FIG. 14C illustrates templated ligation detection and imaging of tissue. FIG. 14D illustrates removal all detection DNA using endonuclease.

FIGS. 14E-14F illustrate that tissue can be dehydrated and stored in either double stranded (FIG. 14E) or single stranded form (FIG. 14F). FIG. 14E illustrates that tissue can be dehydrated and stored in either double stranded or single stranded form. Antisense can be removed through denaturation or enzymatic digestion. FIG. 14F illustrates that upon removal of the antisense, the stained tissue with DNA conjugate primary is returned to the original antibody stained state, thus ready to fresh fluorescent detection.

FIGS. 15A-15F illustrate examples of signal amplification and detection. FIG. 15A shows that a tagged target can be recognized by a single probe that base-pairs to a complementary region on the tag. FIG. 15B shows that a long probe can dock n detection label (e.g. detector . . . n detector). FIG. 15C shows that a long primary detector label (e.g., primary detector) can be hybridized to a short probe. FIG. 15D shows that instead of the addition of single-stranded oligos, a singly or multiply labeled duplex detector can be used. FIG. 15E shows that instead of linear duplex detectors, n-branched detectors can be used to build an extended labeled structure. FIG. 15F shows that linear and branched detectors can be mixed in the extension of an n-branched structure.

FIG. 16A shows labeled duplexed nucleic acid units with unique complementary ends [α and α'] and [β and β']. FIG. 16B shows the linear amplification using alternating α/β and α'/β' labeled duplex units. FIG. 16C shows exemplary 3-way and 4-way branch structures. FIG. 16D shows the structure generated by cycling of 3-way branches. FIG. 16E shows the structure generated by cycling of 4-way branches.

FIG. 17A shows that two adjacent nucleic acid probes can generate a stem hairpin structure upon which a secondary probe hybridizes. FIG. 17B shows the two nucleic acid adjoining probes can generate a 3-way branched structure. FIG. 17C shows the hybridization of the probe generates a three-way branch structure that can directly be used in branched amplification.

FIG. 18A shows the image with an alexa-594 labelled secondary antibody. FIG. 18B shows the image with branched "T" and alexa-594-labelled linear detectors through two cycles. FIG. 18C shows the image with branched "T" and alexa-594-labelled linear detectors through four cycles. FIG. 18D shows the image with branched "T" and alexa-594-labelled linear detectors through six cycles. FIG. 18E shows the image with branched "T" and alexa-594-labelled linear detectors through eight cycles. FIG. 18F shows the image with branched "T" and alexa-594-labelled linear detectors through ten cycles. FIG. 18G shows example of 6-cycle amplification with an overlay of a cell body mask. FIG. 18H shows the cell body mask used in FIG. 18G. FIG. 18I shows the mean pixel intensity for pixels within the cell body mask for secondary antibody (diamond) and 2-10 cycles of branched oligomerization (circles).

FIG. 19A shows the image with an alexa-594 labelled secondary antibody. FIG. 19B shows the image with branched "T" and alexa-594-labelled linear detectors through two cycles. FIG. 19C shows the image with branched "T" and alexa-594-labelled linear detectors through four cycles. FIG. 19D shows the image with branched "T" and alexa-594-labelled linear detectors through six cycles. FIG. 19E shows the image with branched "T" and alexa-594-labelled linear detectors through eight cycles. FIG. 19F shows the mean image intensity (grey value from the 16-bit image) for secondary antibody (diamond) and 2-8 cycles of branched oligomerization (circles).

DETAILED DESCRIPTION OF THE DISCLOSURE

Figure 1:
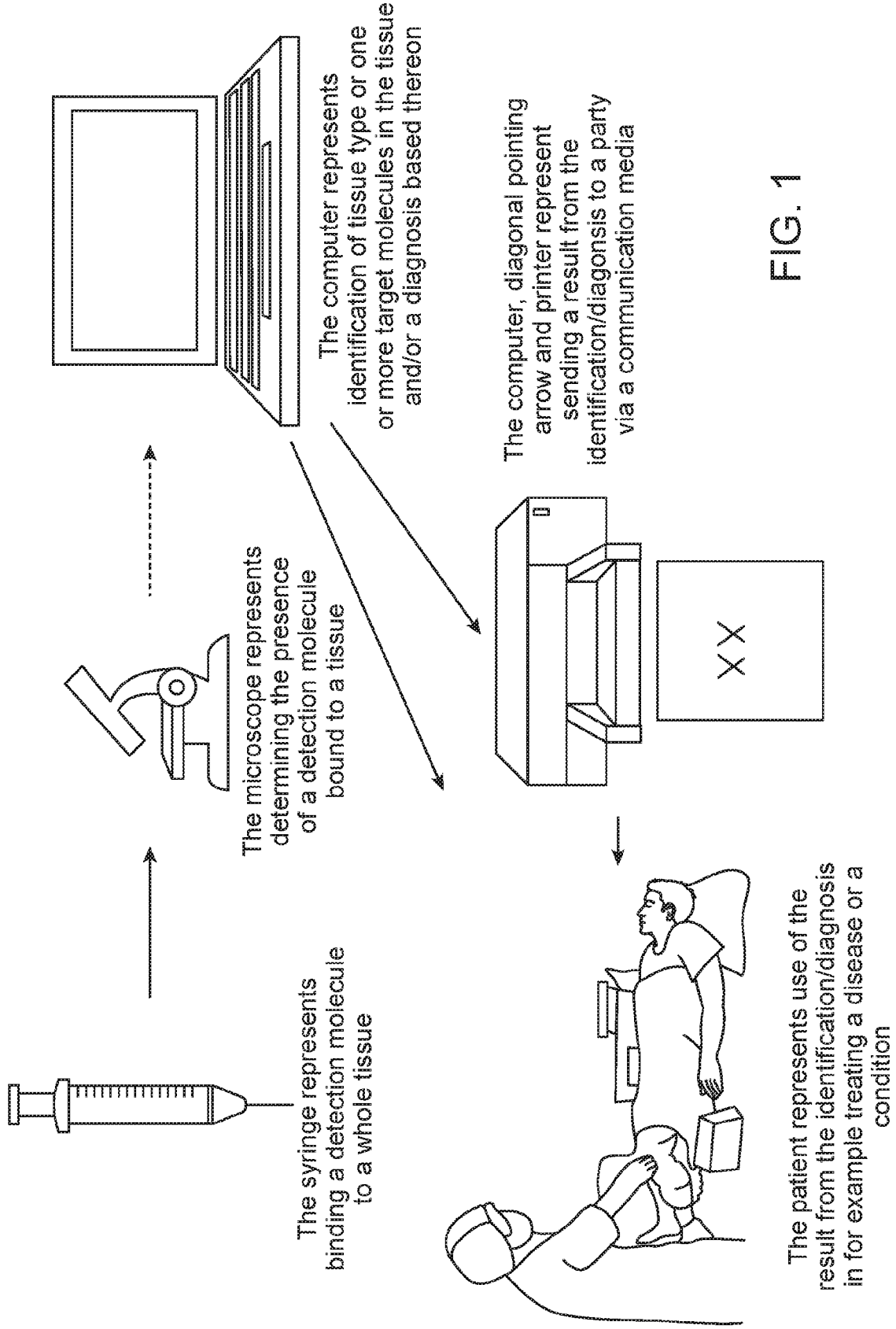
FIG. 1 illustrates an exemplary process of using the compositions, kits, methods, and systems described herein.

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

As used herein, unless otherwise indicated, terms such as "contain," "containing," "include," "including," and the like mean "comprising."

As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The singular forms "a", "an", and "the" are used herein to include plural references unless the context clearly dictates otherwise.

The use of the alternative (e.g., "or") should be understood to mean either one, both, or any combination thereof of the alternatives.

The term "nucleic acid" as used herein generally refers to a polymeric form of nucleotides of any length. Nucleic acids can include ribonucleotides, deoxyribonucleotides or peptide nucleic acids (PNAs), that comprise purine and pyrimidine bases, or other natural, chemically or biochemically modified, non-natural, or derivatized nucleotide bases. A nucleic acid can be single or double stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose, or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule. The nucleic acid molecule may be a synthetic molecule. The nucleic acid molecule may be a synthetic molecule that pair to a DNA or RNA molecule.

As used herein, the term "IHC" or "immunohistochemistry" refers to the process of selectively imaging antigens (e.g. proteins or nucleic acids) in cells of a tissue section. This method can employ antibodies that bind to specific antigens in biological tissues. The detection signal (e.g. fluorescence) can be amplified by ligation amplification methods as provided herein. In some embodiments, the detection signal is amplified via ligation oligomerization. In some embodiments, the detection signal is amplified via templated oligomerization.

Practicing this invention utilizes routine techniques in the field of molecular biology. Basic texts disclosing the general methods of use in this invention include Sambrook and Russell, Molecular Cloning, A Laboratory Manual (3rd ed. 2001); Kriegler, *Gene Transfer and Expression: A Laboratory Manual* (1990); and *Current Protocols' in Molecular Biology* (Ausubel et al., eds., 1994)).

Overview

Disclosed herein are compositions, kits, methods, and systems for detecting a target molecule in a sample. FIG. 1 illustrates an exemplary process of using the compositions, kits, methods, and systems described herein. First, a detection molecule can be used to contact a sample (e.g., whole tissue sample). The presence of the detection molecule can be detected by an imaging instruction (e.g., a microscope). Then a computer system can be used to identify one or more tissue types, one or more target molecules in the sample, and/or one or more conditions. The results can be communicated to doctor or physicians for identification or diagnosis of a disease or a condition.

In some embodiments, a ligation amplification method provided herein may comprise: contacting a target molecule in a sample with a detection molecule (e.g., detection couplet) with an overhang; contacting the detection molecule with one or more double-stranded nucleic acids with complimentary overhangs; and ligating the one or more double-stranded nucleic acids to the detection molecule (e.g., to amplify the detection signal) using a DNA ligase. This method may also be referred to herein as ligation oligomerization.

Figure 2A:
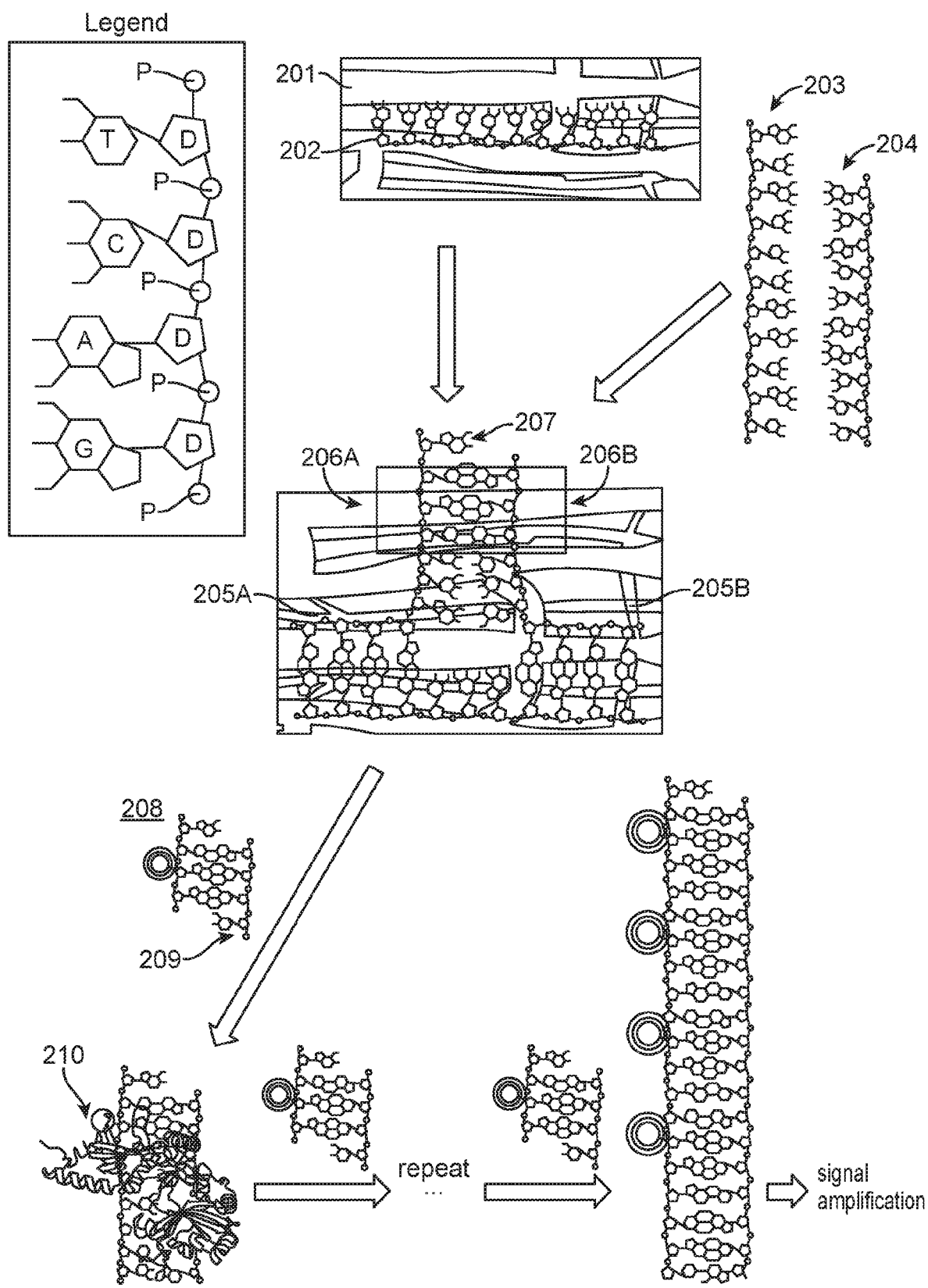
FIG. 2A illustrates an exemplary ligation oligomerization method for detecting a target molecule in a tissue sample.
Figure 2B:
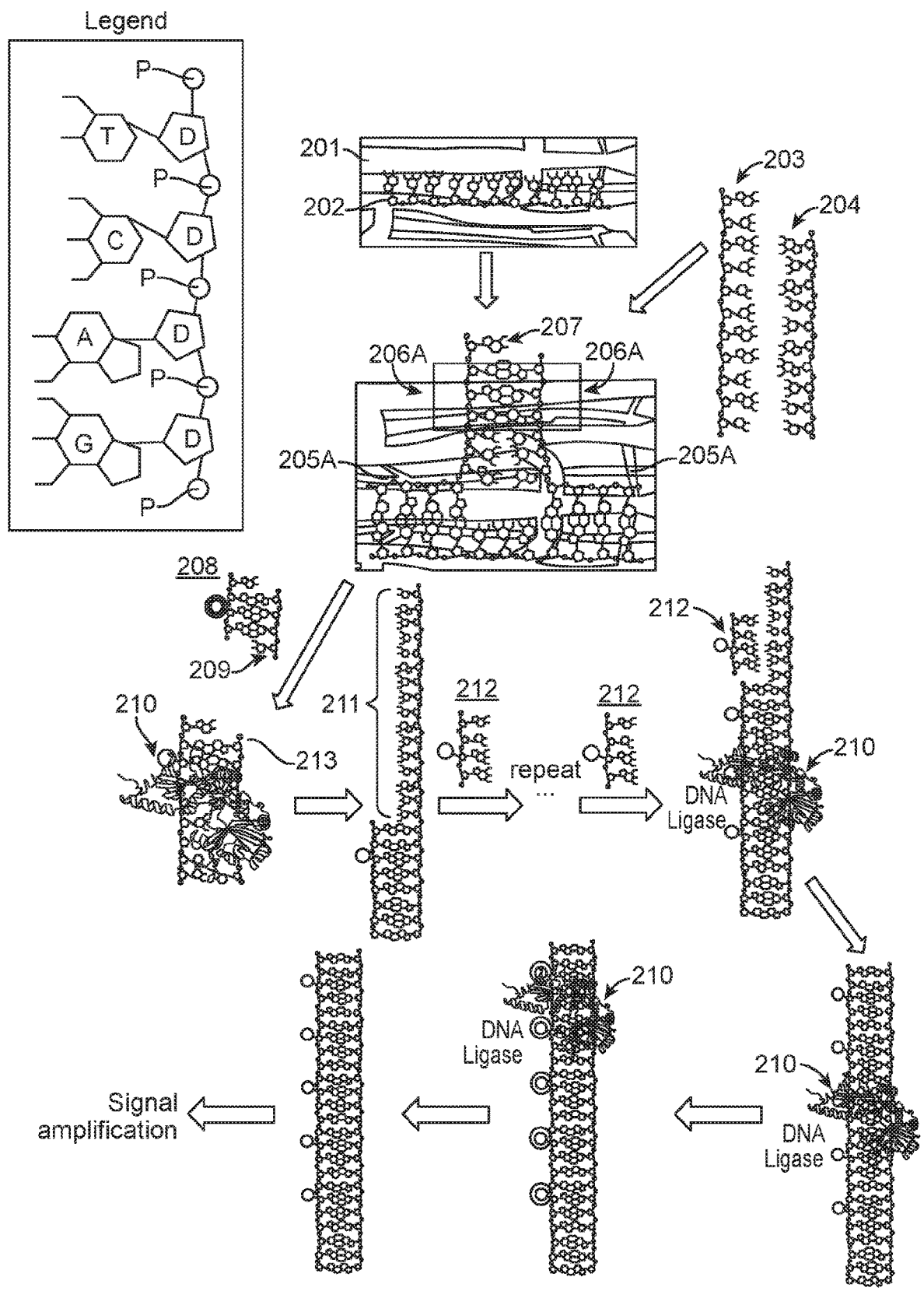
FIG. 2B illustrates an exemplary templated oligomerization method for detecting a target molecule in a tissue sample.

In another embodiment, a ligation amplification method provided herein may comprise: contacting a target molecule in a sample with a detection molecule (e.g., detection couplet) with an overhang; contacting the detection molecule with one or more single-stranded nucleic acids that is complimentary to the overhang sequence of the detection molecule; and ligating the one or more single-stranded nucleic acids to the detection molecule (e.g., to amplify the detection signal) using a DNA ligase. This method may also be referred to herein as templated oligomerization. The terms "templated oligomerization" and "controlled oligomerization" can be used interchangeably herein to refer to the methods of ligation amplification comprising contacting at least one single-stranded detection label complementary to a detection couplet overhang. Exemplary methods comprising ligation oligomerization or templated oligomerization for detecting a target molecule in a tissue sample 201 are illustrated in FIGS. 2A, 2B and 13. FIG. 2A illustrates an exemplary ligation oligomerization method for detecting a target molecule in a tissue sample 201. In some cases, the target molecule can be an mRNA molecule 202. The method can comprise contacting the target molecule with a detection couplet, wherein the detection couplet comprises a first nucleic acid 203 and a second nucleic acid 204. The first nucleic acid 203 and second nucleic acid 204 each can have a target recognition region 205A & 205B, as well as a self-hybridization region 206A & 206B. The target recognition region of the first nucleic acid 205A can bind a first region of the target molecule, and the target recognition region of the second nucleic acid 205B can bind a second region of the target molecule. The self-hybridization region of the first nucleic acid 206A and the self-hybridization region of the second nucleic acid 206B can be hybridized to form a double-stranded nucleic acid label 206A & 206B. The double-stranded nucleic acid label 206A & 206B can have at least three consecutive base pairs. The double-stranded nucleic acid label 206A & 206B can have an overhang 207. The method can further comprise contacting the double-stranded nucleic acid label 206A & 206B with a detection label 208, wherein the detection label 208 is a double-stranded nucleic acid with an overhang 209 that is complementary to the overhang 207 of the double-stranded nucleic acid label 206. The detection label 208 can comprise a detection tag (e.g., fluorophore). The method can further comprise contacting the detection label with a DNA ligase 210, wherein the DNA ligase 210 can ligate the detection label 208 and the double-stranded nucleic acid label 206A & 206B.

The ligation oligomerization method provided herein can further comprise the DNA ligase 210 repeating the ligation process multiple times and add a plurality of double-stranded detection label 208 to the double-stranded nucleic acid label 206A & 206B, amplifying the detection signal for imaging applications.

FIG. 2B illustrates an exemplary templated oligomerization method for detecting a target molecule in a tissue sample 201. For example, the templated oligomerization method provided herein can further comprise a detection couplet, wherein the detection couplet comprises a first nucleic acid 203 and a second nucleic acid 204. The first nucleic acid 203 and second nucleic acid 204 each can have a target recognition region 205A & 205B and a self-hybridization region 206A & 205B. In some embodiments of templated oligomerization, the method can further comprise contacting the double-stranded nucleic acid label 206A & 206B with a detection label 208, wherein the detection label 208 is a double-stranded nucleic acid with an overhang 209 that is complementary to the overhang 207 of the double-stranded nucleic acid label 206. The detection label 208 can comprise a detection tag (e.g., fluorophore). The method can further comprise contacting the detection label with a DNA ligase 210, wherein the DNA ligase 210 can ligate the detection label 208 and the double-stranded nucleic acid label 206A & 206B. The method can further comprise synthesizing an overhang 211 onto the strand 213. In another embodiment of templated oligomerization, the detection couplet can further comprise an overhang 211 comprising a plurality of nucleotides, for example, 1, 2, 3, 4, 5, 6, 7, 8, 9, 10, 11, 12, 13, 14, 15, 16, 17, 18, 19, or 20 nucleotides, wherein the overhang is complementary to a plurality of single-stranded nucleic acid detection label 212. The detection label 212 can comprise a detection tag (e.g., fluorophore). The templated oligomerization method can further comprise contacting the plurality of the detection label 212 with a DNA ligase 210, wherein the DNA ligase 210 can ligate the plurality of the detection label 212 and the overhang 211. In some embodiments, the sequences of at least two detection labels are identical, for example, at least 2, at least 3, at least 4, at least 5, at least 6, at least 7, at least 8, at least 9, at least 10, at least 11, at least 12, at least 13, at least 14, or at least 15, or at least 16, or at least 17, or at least 18, or at least 19, or at least 20 detection labels. In some embodiments, the sequences of at least a first detection label are different from the sequences of at least a second detection label. In some embodiments, the plurality of the detection label may comprise at least 2, 3, 4, 5, 6, 7, 8, 9, 10, 11, 12, 13, 14, 15, 16, 17, 18, 19 or 20 detection labels 212, wherein the sequence of a first detection label is complementary to at least a first two consecutive nucleotides of the overhang 211, the sequence of a second detection label is complementary to at least a second two consecutive nucleotides of the overhang 211, the sequence of a third detection label is complementary to at least a third two consecutive nucleotides of the overhang 211, and so forth. The methods provided herein can amplify the detection signal for imaging applications.

Figures 13A, 13B:
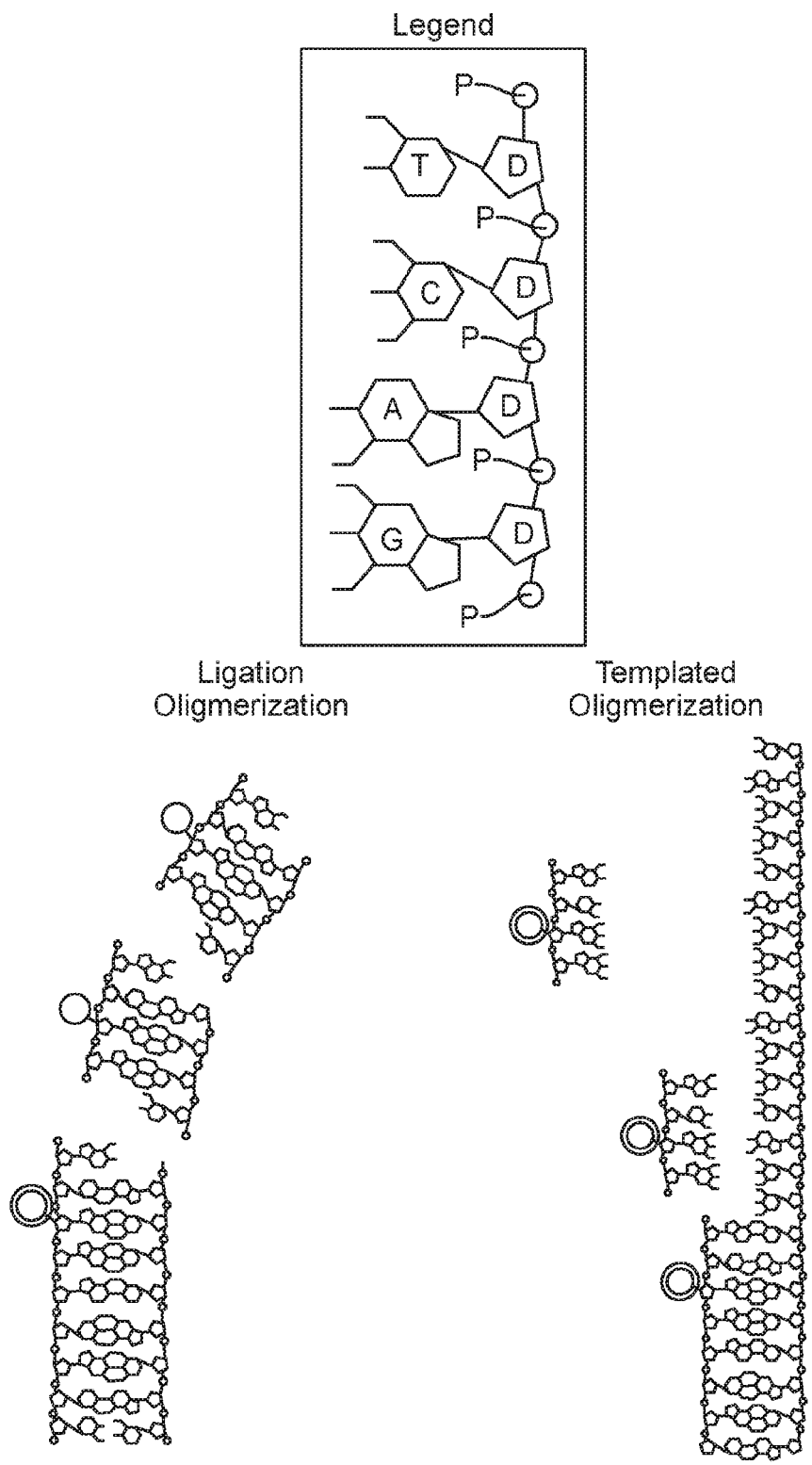
FIGS. 13A-13B compare two ligation implication methods.

In some embodiments, fluorescence detection signal is amplified through ligation oligomerization, as shown in FIG. 13A. In some embodiments, fluorescence detection signal is amplified through template oligomerization, in which fluorescence amplification occurs through the sequential hybridization and ligation of single stranded small DNA with fluorophores, as shown in FIG. 13B.

The methods disclosed herein can comprise contacting the sample or the detection molecule with at least one detection label (e.g., double-stranded DNA), wherein the at least one detection label has an overhang that is complementary to the overhang of the double-stranded nucleic acid label. The methods disclosed herein can comprise contacting the sample or the detection molecule with at least one detection label (e.g., single-stranded DNA), wherein the at least one detection label is complementary to the overhang of either the first or the second strand of the detection couplet. The at least one detection label can be a nucleic acid molecule, such as a single-stranded DNA, a single-stranded RNA, or double-stranded DNA. For example, if the double-stranded nucleic acid label has an overhang sequence of: 5'-TAG-3', then the detection label can have a complementary overhang sequence of: 3'-ATC-5'. For example, if a sequence of a single-stranded nucleic acid label is 5'-GGTA-3', then the overhang sequence comprises 3'-CCAT-5'. The overhang sequence of the detection label can be uniquely complementary to the overhang of a particular double-stranded nucleic acid label. The overhang sequence of the detection label can be complementary to the overhangs of a plurality of double-stranded nucleic acid labels, for example, between 1, 2, 3, 4, 5, 6, 7, 8, 9, 10, 11, 12, 13, 14, 15, 16, 17, 18, 19 and 20 double-stranded nucleic acid labels. Similarly, the overhang sequence of the double-stranded nucleic acid label can be uniquely complementary to the overhangs of a particular detection label. The overhang sequence of the double-stranded nucleic acid label can be complementary to the overhangs of a plurality of detection labels, for example, between 1, 2, 3, 4, 5, 6, 7, 8, 9, 10, 11, 12, 13, 14, 15, 16, 17, 18, 19 and 20 detection labels.

The methods disclosed herein can comprise contacting the sample or the detection molecule with at least one DNA ligase. The DNA ligase can facilitate the joining of DNA strands together by catalyzing the formation of a phosphodiester bond. For example, the DNA ligase can comprise a *E. coli* DNA ligase, a T4 DNA ligase, or a mammalian DNA ligase I, II III, or IV.

Figure 5:
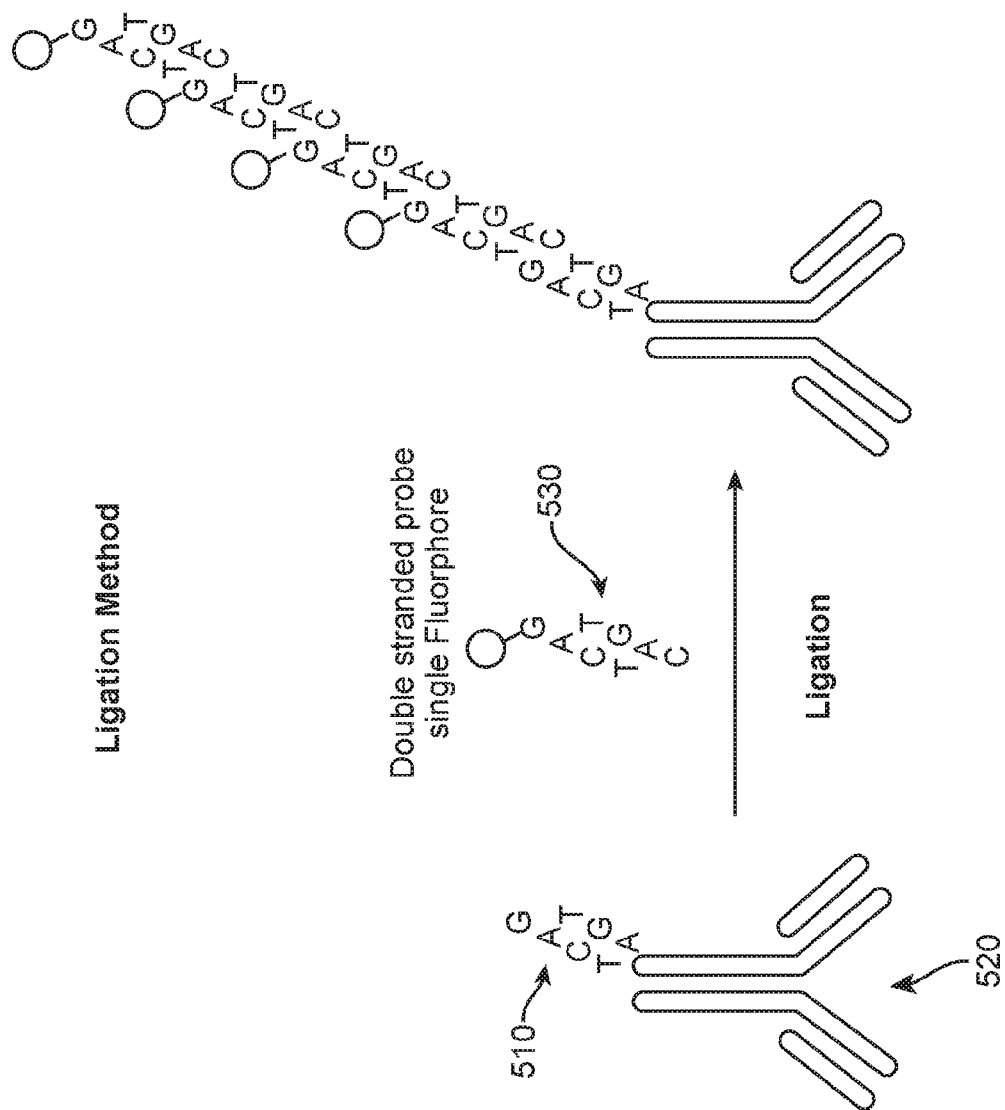
FIG. 5 illustrates that a double-stranded nucleic acid label of the detection molecule can be amplified with four double-stranded detection label with the same sequence through a ligation reaction. Figure discloses SEQ ID NOS 2-3, respectively, in order of appearance.

The double-stranded nucleic acid label can be ligated to a first detection label to form an amplified double-stranded nucleic acid label, for example, using a DNA ligase. The amplified double-stranded nucleic acid label can be ligated to a second detection label to form another amplified double-stranded nucleic acid label. This process can be repeated multiple times to form an amplified double-stranded nucleic acid label comprising a plurality of detection labels. In some cases, the first detection label can have the same sequence as the second detection label. As shown in FIG. 5, the double-stranded nucleic acid label 510 of the detection molecule 520 can be amplified with four double-stranded detection labels 530 with the same sequence through a ligation reaction. In some cases, the first detection label can have a different sequence as the second detection label. In some cases, the detection molecule 520 can be amplified with four single-stranded detection labels with the same sequence through a templated oligomerization ligation reaction as illustrated in FIG. 2B. In some cases, the detection molecule 520 can be amplified with one double stranded acid molecule 510 and three single-stranded detection labels with the same sequence through a templated oligomerization ligation reaction as illustrated in FIG. 2B.

Detecting a Target Molecule Using a Detection Molecule

Disclosed herein are compositions, kits, methods, and systems for detecting a target molecule in a sample. The target molecule can be any molecule of interest in the sample. The target molecule can be a carbohydrate, a lipid, a protein, or a nucleic acid (e.g., DNA or RNA). The target molecule can be a RNA molecule, for example, an mRNA, a tRNA, a rRNA, a snRNA, or an non-coding RNA molecule.

The present methods can comprise contacting the sample with a detection molecule that binds the target molecule. The detection molecule can comprise at least one ligand (e.g., antibody), bead, or nucleic acid. The ligand can be an antibody linked to a single-stranded nucleic acid. The single-stranded nucleic acid can be hybridized to an antisense oligomer, which has a sequence complementary to the single-stranded nucleic acid, to form a double-stranded nucleic acid label, wherein the double-stranded nucleic acid label has an overhang. The hybridization of the single-stranded nucleic acid and the antisense oligomer can be performed after the binding of the ligand to the target molecule. The hybridization of the single-stranded nucleic acid and the antisense oligomer can be performed before the binding of the ligand to the target molecule. In some cases, the ligand can be an antibody linked to a double-stranded nucleic acid label, wherein the double-stranded nucleic acid label has an overhang.

Overhang

Figure 3:
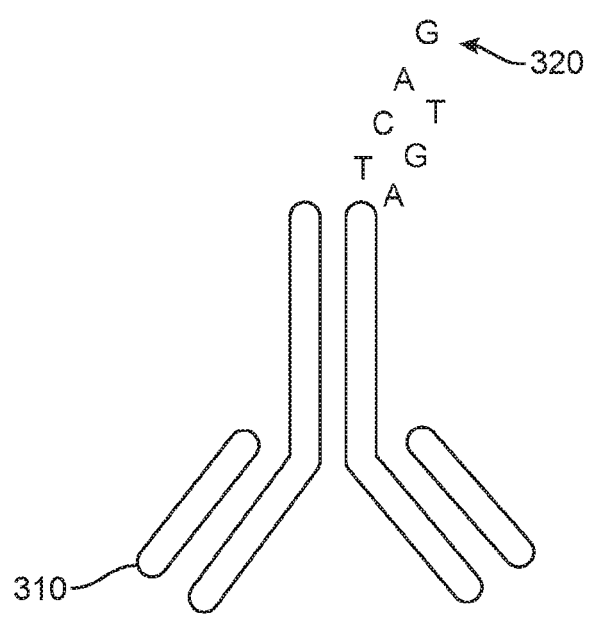
FIG. 3 illustrates an antibody linked to a double-stranded nucleic acid (e.g., DNA) label with a single Guanine (G) overhang.

The term "overhang" as used herein refers to a stretch of unpaired nucleotides in the end of a nucleic acid (e.g., DNA) molecule. These unpaired nucleotides can be in either strand, creating either 3' or 5' overhangs. An overhang can comprise a single nucleotide. For example, in FIG. 3, the detection molecule is an antibody 310 linked to a double-stranded nucleic acid (e.g., DNA) label with a single Guanine (G) overhang 320. In another example, a double-stranded DNA molecule with the following sequences can form a single nucleotide overhang:

```
5'-ATCTGACTA-3'

3'-TAGACTGA-5'
```

An overhang can comprise a single nucleotide or a plurality of nucleotides, for example, 1, 2, 3, 4, 5, 6, 7, 8, 9, 10, 11, 12, 13, 14, 15, 16, 17, 18, 19, or 20 nucleotides. In some cases, the overhang can comprise at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 nucleotides. In some cases, the overhang can comprise from about 1 to about 20 nucleotides, for example, from about 1 to about 2, from about 1 to about 3, from about 1 to about 4, from about 1 to about 5, from about 1 to about 10, from about 1 to about 15, from about 1 to about 20, from about 2 to about 3, from about 2 to about 4, from about 2 to about 5, from about 2 to about 10, from about 2 to about 15, from about 2 to about 20, from about 3 to about 4, from about 3 to about 5, from about 3 to about 10, from about 3 to about 15, from about 3 to about 20, from about 4 to about 5, from about 4 to about 10, from about 4 to about 15, from about 4 to about 20, from about 5 to about 10, from about 5 to about 15, from about 5 to about 20, from about 10 to about 15, from about 10 to about 20, or from about 15 to about 20 nucleotides. For instance, the overhang sequence can be TAG, CAT, ACA, CAT, or AAT. In another example, a double-stranded DNA molecule with the following sequences can form a three-nucleotide overhang:

```
                                    (SEQ ID NO: 1)
                    5'-ATCTGACTA-3'

3'-TAGACTGA-5'
```

Detection Couplet

The detection molecule can comprise a plurality of nucleotides that binds the target molecule. For example, the detection molecule can be a detection couplet, which comprises a first nucleic acid and a second nucleic acid. The first and second nucleic acids can be single-stranded DNA.

The first and/or second nucleic acid can comprise a plurality of nucleotides in length, for example, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides. The first and/or second nucleic acid can comprise about 5-150 nucleotides in length, for example, about 5-150, about 5-130, about 5-110, about 5-90, about 5-70, about 5-50, about 5-30, about 5-10, about 10-150, about 10-130, about 10-110, about 10-90, about 10-70, about 10-50, about 10-30, about 30-150, about 30-130, about 30-110, about 30-90, about 30-70, about 30-50, about 50-150, about 50-130, about 50-110, about 50-90, about 50-70, about 70-150, about 70-130, about 70-110, about 70-90, about 90-150, about 90-130, about 90-110, about 110-150, about 110-130, or about 130-150 nucleotides.

Recognition Region

Figures 4A, 4B:
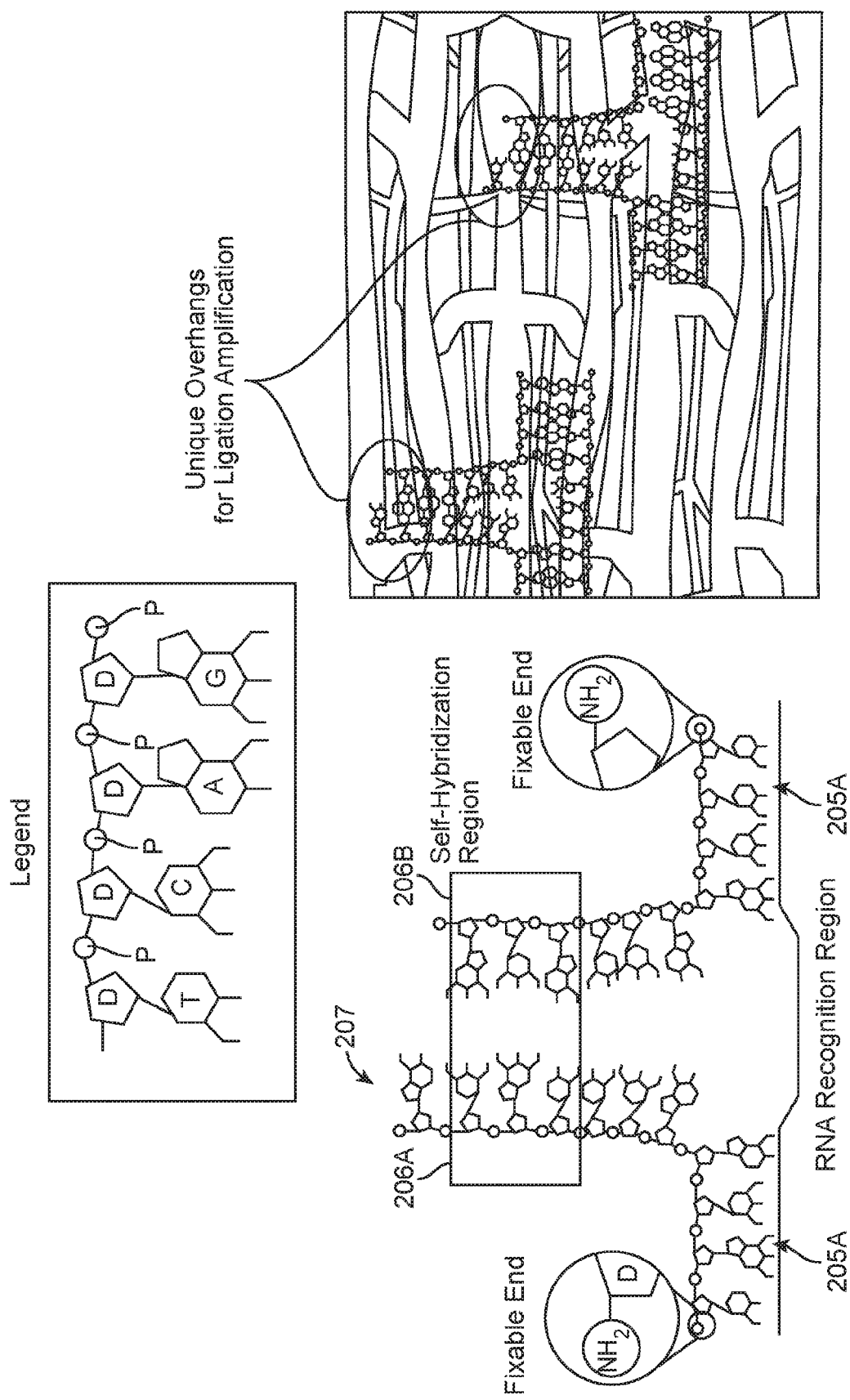
FIG. 4A illustrates a detection couplet, including a first nucleic acid and a second nucleic acid, wherein each nucleic acid can have a recognition region (e.g., RNA recognition region), a self-hybridization region, and a fixable end.
FIG. 4B illustrates that the self-hybridization regions of the first nucleic acid and the second nucleic acid can be hybridized to form a double-stranded nucleic acid label with an overhang.

As illustrated in the example of FIG. 4A, the first nucleic acid has a first recognition region 205A (e.g., RNA recognition region) that binds a first target molecule (e.g., mRNA). Similarly, the second nucleic acid has a second recognition region 205A (e.g., RNA recognition region) that binds a second target molecule (e.g., mRNA). In some cases, the first and second target molecule can be the same molecule. In some cases, the first target molecule and second target molecule can be different molecules. The recognition region of the first and/or second nucleic acid binds to the target molecule by hybridizing to a sequence of the target molecule that is complementary to the sequence of the recognition region.

The recognition region can comprise a single nucleotide or a plurality of nucleotides, for example, 1, 2, 3, 4, 5, 6, 7, 8, 9, 10, 11, 12, 13, 14, 15, 16, 17, 18, 19, or 20 nucleotides. In some cases, the recognition region can comprise at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 nucleotides. In some cases, the recognition region can comprise from about 1 to about 20 nucleotides, for example, from about 1 to about 2, from about 1 to about 3, from about 1 to about 4, from about 1 to about 5, from about 1 to about 10, from about 1 to about 15, from about 1 to about 20, from about 2 to about 3, from about 2 to about 4, from about 2 to about 5, from about 2 to about 10, from about 2 to about 15, from about 2 to about 20, from about 3 to about 4, from about 3 to about 5, from about 3 to about 10, from about 3 to about 15, from about 3 to about 20, from about 4 to about 5, from about 4 to about 10, from about 4 to about 15, from about 4 to about 20, from about 5 to about 10, from about 5 to about 15, from about 5 to about 20, from about 10 to about 15, from about 10 to about 20, or from about 15 to about 20 nucleotides.

The first recognition region and the second recognition region can recognize two sequences of the target molecule that are separated by at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 nucleotides. The first recognition region and the second recognition region can recognize two sequences of the target molecule that are separated by from about 1 to about 20 nucleotides, for example, from about 1 to about 2, from about 1 to about 3, from about 1 to about 4, from about 1 to about 5, from about 1 to about 10, from about 1 to about 15, from about 1 to about 20, from about 2 to about 3, from about 2 to about 4, from about 2 to about 5, from about 2 to about 10, from about 2 to about 15, from about 2 to about 20, from about 3 to about 4, from about 3 to about 5, from about 3 to about 10, from about 3 to about 15, from about 3 to about 20, from about 4 to about 5, from about 4 to about 10, from about 4 to about 15, from about 4 to about 20, from about 5 to about 10, from about 5 to about 15, from about 5 to about 20, from about 10 to about 15, from about 10 to about 20, or from about 15 to about 20 nucleotides. For example, in FIG. 4B, the first recognition region and the second recognition region can recognize two sequences of the target mRNA molecule that are separated by 3 nucleotides ("UCA" and "CCU" on FIG. 4B).

Self-Hybridization Region

The first nucleic acid can comprise a first self-hybridization region 206A (FIG. 4A). Similarly, the second nucleic acid can comprise a second self-hybridization region 206B. The sequences of the first and second self-hybridization regions can be complementary. The first and second self-hybridization regions can hybridize through sense-antisense hybridization to form a double-stranded nucleic acid label. The double-stranded nucleic acid label can be partially double-stranded and partially single-stranded.

The self-hybridization region can comprise a single nucleotide or a plurality of nucleotides, for example, 1, 2, 3, 4, 5, 6, 7, 8, 9, 10, 11, 12, 13, 14, 15, 16, 17, 18, 19, or 20 nucleotides. In some cases, the self-hybridization region can comprise at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 nucleotides. In some cases, the self-hybridization region can comprise from about 1 to about 20 nucleotides, for example, from about 1 to about 2, from about 1 to about 3, from about 1 to about 4, from about 1 to about 5, from about 1 to about 10, from about 1 to about 15, from about 1 to about 20, from about 2 to about 3, from about 2 to about 4, from about 2 to about 5, from about 2 to about 10, from about 2 to about 15, from about 2 to about 20, from about 3 to about 4, from about 3 to about 5, from about 3 to about 10, from about 3 to about 15, from about 3 to about 20, from about 4 to about 5, from about 4 to about 10, from about 4 to about 15, from about 4 to about 20, from about 5 to about 10, from about 5 to about 15, from about 5 to about 20, from about 10 to about 15, from about 10 to about 20, or from about 15 to about 20 nucleotides.

The methods herein can comprise hybridizing the self-hybridization regions of the first nucleic acid and the second nucleic acid to form a double-stranded nucleic acid label with an overhang 207 described herein (examples are shown in FIGS. 4A and 4B).

Fixing Detection Molecule to the Sample

The detection couplet can comprise 3' and/or 5' modification that can be used for fixation of the detection couplet to the sample (e.g., tissue). Fixing detection couplet to the tissue can allow various processing without negatively affecting the detectability of the target molecule (e.g., mRNA).

The detection couplet, including the first and second nucleic acids, can have a 3' or 5' modification, such as a free amine (—NH2) modification (shown in FIG. 4A). The methods disclosed herein can comprise contacting an amine reactive crosslinker, such as a NHS ester crosslinker, a imidoester crosslinker, or a difluoro crosslinker. The NHS ester crosslinker can be disuccinimidyl glutarate (DSG), disuccinimidyl suberate (DSS), bis(sulfosuccinimidyl)suberate (BS3), tris-(succinimidyl)aminotriacetate (TSAT), PEGylated bis(sulfosuccinimidyl)suberate (BS(PEG)5, BS(PEG)9), dithiobis(succinimidyl propionate) (DSP), 3,3'-dithiobis(sulfosuccinimidyl propionate) (DTSSP), disuccinimidyl tartrate (DST), bis(2-(succinimidooxycarbonyloxy) ethyl)sulfone (BSOCOES), ethylene glycol his (succinimidyl succinate) (EGS), or Sulfo-EGS. The imidoester crosslinker can be dimethyl adipimidate (DMA), dimethyl pimelimidate (DMP), dimethyl suberimidate (DMS), or Wang and Richard's Reagent (DTBP). The difluoro crosslinker can be 1,5-difluoro-2,4-dinitrobenzene (DFDNB).

Detection Label and Ligation Amplification

The methods disclosed herein can comprise contacting the sample or the detection molecule with at least one detection label (e.g., double-stranded DNA), wherein the at least one detection label has an overhang that is complementary to the overhang of the double-stranded nucleic acid label. The at least one detection label can be a nucleic acid molecule, such as a single-stranded DNA, a single-stranded RNA, or double-stranded DNA. For example, if the double-stranded nucleic acid label has an overhang sequence of: 5-TAG-3', then the detection label can have a complementary overhang sequence of: 3'-ATC-5'. The overhang sequence of the detection label can be uniquely complementary to the overhang of a particular double-stranded nucleic acid label. The overhang sequence of the detection label can be complementary to the overhangs of a plurality of double-stranded nucleic acid labels, for example, between 1, 2, 3, 4, 5, 6, 7, 8, 9, 10, 11, 12, 13, 14, 15, 16, 17, 18, 19 and 20 double-stranded nucleic acid labels. Similarly, the overhang sequence of the double-stranded nucleic acid label can be uniquely complementary to the overhangs of a particular detection label. The overhang sequence of the double-stranded nucleic acid label can be complementary to the overhangs of a plurality of detection labels, for example, between 1, 2, 3, 4, 5, 6, 7, 8, 9, 10, 11, 12, 13, 14, 15, 16, 17, 18, 19 and 20 detection labels. The detection labels can comprise one or more detection tags. The detection label can have at least one overhang that can be adapted for manual assembly and/or self assembly. In some cases, the detection labels can be adapted for manual assembly and can have the serial application of individual units to build a larger complex (e.g., signaling complex). In some cases, the detection labels can be adapted for self assembly and can have the simultaneous application of all components to build a larger complex (e.g., signaling complex).

The methods disclosed herein can comprise contacting the sample or the detection molecule with at least one DNA ligase. The DNA ligase can facilitate the joining of DNA strands together by catalyzing the formation of a phosphodiester bond. For example, the DNA ligase can comprise a *E. coli* DNA ligase, a T4 DNA ligase, or a mammalian DNA ligase I, II III, or IV.

The double-stranded nucleic acid label can be ligated to a first detection label to form an amplified double-stranded nucleic acid label, for example, using a DNA ligase. The amplified double-stranded nucleic acid label can be ligated to a second detection label to form another amplified double-stranded nucleic acid label. This process can be repeated multiple times to form an amplified double-stranded nucleic acid label comprising a plurality of detection labels. In some cases, the first detection label can have the same sequence as the second detection label. As shown in FIG. 5, the double-stranded nucleic acid label 510 of the detection molecule 520 can be amplified with four double-stranded detection labels 530 with the same sequence through a ligation reaction. In some cases, the first detection label can have a different sequence as the second detection label. In some cases, the detection molecule 520 can be amplified with four single-stranded detection labels with the same sequence through a templated oligomerization ligation reaction as illustrated in FIG. 2B. In some cases, the detection molecule 520 can be amplified with one double stranded acid molecule 510 and three single-stranded detection labels with the same sequence through a templated oligomerization ligation reaction as illustrated in FIG. 2B.

Natural and synthetic nucleic acids can be joined by direct hybridization, enzymatic ligation or chemical ligation. In some cases, direct hybridization comprises the joining of nucleic acids by base pairing only. Direct hybridization can be non-covalent and the stability of the joined structure can be sensitive to environmental factors such as salt concentration and temperature. Enzymatic ligation can provide a direct covalent linkage of nucleic acids, but may require a protein ligase. Chemical ligation can provides a convenient method of covalently joining two nucleic acids. Chemical ligation forms can comprise: crosslinking of nucleic acids with 3' and 5' amino groups using an aldehyde to directly join the strand; oxidation of 3' and 5' sulfhydryl groups to generate a disulfide linked nucleic acid strands; and bio-orthogonal "click" chemistries that can covalently join the 3' and 5' ends of adjacent nucleic acid strands, for example, a 3' labeled azide and a 5' labeled alkyne can be joined via Cu(I) catalyzed cycloaddition to form a triazol covalent linkage instead of the normal phosphate bond (El-Sagheer, A. H. & Brown, T. Click Nucleic Acid Ligation: Applications in Biology and Nanotechnology. *Acc. Chem. Res.* 45, 1258-1267 (2012). The ligation can be by enzymatic ligation, chemical cross-linking, for example aldehyde or sulfhydryl crosslinking, or bio-orthogonal "click" chemistries such as alkyne-azide cycloadditions.

Branched Oligomerization

The detection labels used to generate a larger complex can be either linear or branched. A structure made of only linear detection labels may amplify signals linearly to the number of linear modules. A structure made of branched, or a combination of linear and branched, detection labels may provide a signal that can be amplified exponentially to the number of branching detection labels. The structures and effects of branched oligomerization are shown in Examples 11 to 14.

In some cases, the multi-way branch is a n-way branch, wherein the n-way branch comprises n single stranded nucleic acid that are linked together to form a nucleic acid structure. The nucleic acid structure can have n terminals and/or n overhangs. For example, the multi-way branch can be a three-way branch, wherein the three-way branch comprises three single stranded nucleic acid that are linked together to form a nucleic acid structure that have three terminals and/or three overhangs (see e.g., FIG. 17A-C and FIG. 16C). In another example, the multi-way branch can be a four-way branch. The four-way branch can comprise four single stranded nucleic acid that are linked together to form a nucleic acid structure that have four terminals and/or four overhangs.

Detection Tags

The detection label can comprise at least one detection tag. In some cases, the detection label may also comprise a plurality of detection tags. In some cases, the detection label may comprise between 1, 2, 3, 4, 5, 6, 7, 8, 9, 10, 11, 12, 13, 14, 15, 16, 17, 18, 19 and 20 detection tags. In some cases, the plurality of detection tags can be the same type of detection tag. In some cases, the plurality of detection tags can comprise more than one types of detection tags. In some cases, the plurality of detection tags can comprise more than one types of detection tags with the same color. In some cases, the plurality of detection tags can comprise more than one types of detection tags with different colors. In some cases, the plurality of detection tags can comprise more than one colors.

The at least one detection tag can be attached to the detection label by a linker, for example, a cleavable or a non-cleavable linker. In some cases, a plurality of detection tags are attached to the detection label, each spaced between seven and ten bases apart from each other. In some cases, the plurality of detection tags are attached such that each tag is spaced between 2, 3, 4, 5, 6, 7, 8, 9, 10, 11, 12, 13, 14, and 15 bases apart. In some instances, the plurality of detection tags may comprise between two and ten detection tags. In some cases, the plurality of detection tags may comprise between 1, 2, 3, 4, 5, 6, 7, 8, 9, 10, 11, 12, 13, 14, 15, 16, 17, 18, 19 and 20 detection tags.

In some cases, the detection tag can be a quantum dot (QD). In some cases, the detection tag can be a fluorophore. Any fluorophore and/or QD known to the skilled artisan may be employed in the methods and systems described herein. In some exemplary instances, the fluorophore may comprise a coumarin, rhodamine, xanthene, fluorescein, or cyanine. In some cases, the placement and number of detection tags may be optimized to enhance spatial resolution of the detection.

In some cases, the detection tag can be a hapten. The hapten can comprise aniline, an aniline derivative (o-, m-, or p-aminobenzoic acid), urushiol, hydralazine, fluorescein, biotin, digoxigenin, or dinitrophenol. For example, the hapten can be digoxigenin. The hapten (e.g., digoxigenin) can be recognized by an enzyme labeled antibody (e.g., HRP, AP) that can catalyze the generation of absorptive or fluorescent molecules.

The hybridization of the detection tag with the nucleic acid label may comprise application of an electric field. In some cases, the electric field may be applied for about 1, 2, 3, 4, 5, 6, 7, 8, 9, 10, 12, 15, 20, 25, 30, 35, 40, 45, 50, 55, or 60 seconds. In some cases, the electric field maybe applied for between 0.5, 1, 1.5, 2, 2.5, 3, 3.5, 4, 4.5, and 5 minutes. In some cases, the electric field maybe applied for up to 5, 10, 15, 20, 25, 30, 35, 40, 45, 50, 55, 60, 65, 70, 75, 80, 85, or 90 minutes. In some cases, the electric field maybe applied between 1 and 60 minutes.

The methods disclosed herein can comprise contacting the sample and/or the detection molecule with phosphatase and/or another double-stranded DNA, such as sonicated salmon sperm. The phosphatase and/or another double-stranded DNA (e.g., sonicated salmon sperm) can be used to reduce undesired signals in the nucleus and/or cytosol due to the presence of DNA (chromatin) and DNA binding proteins.

Also provided are systems suitable for carrying out the methods described herein, and kits for use with such systems.

Detection by Sequencing

The methods described herein may comprise a detection step that comprises determining the sequence of each nucleic acid label. In general any sequencing method that can be performed in-situ can be utilized for sequencing the nucleic acid labels herein. These include for instance sequencing by synthesis, sequencing by ligation, sequencing by hybridization among other methods known to the skilled artisan. Commercially available nucleic acid sequencing kits may be optimized for use with the methods and systems described herein.

In some cases the sequence of each nucleic acid label may be determined by sequencing by synthesis. In some instances, the sequence of each nucleic acid label may be determined by sequencing by hybridization. Sequencing by hybridization may involve use of the tag hybridization method described in the examples below.

Tag sequencing is a variant of direct sequencing uses tags that are about 60 base pairs (bp) consisting of 4 about 15mer units as described in the examples below. In some cases each oligomer is 9, 10, 11, 12, 13, 14, 15, 16, 17, 18, 19, or 20 nucleic acids in length. In some cases, tag 'sequencing' by hybridization is used with QD-labeled oligomers. Using QDs enables reasonably high-speed STORM-like imaging. Further, the quantum dots do not need to be photo-activated, are resistant to photobleaching, and require a single color for excitation. In some cases, tag sequencing is used with cleavable fluorescent labels.

Also provided are systems suitable for carrying out the methods described herein, and kits for use with such systems.

Array Tomography

Also disclosed herein are compositions, kits, methods, and systems for performing array tomography (AT) on an intact tissue to facilitate spatially resolved identification of a plurality of proteins in the tissue. In some cases, the methods can image neural circuit architectures, such as brain tissues.

It may be noted that the one version of the AT process as currently practiced comprises tissue processing similar to that used for electron microscopy, including chemical fixation, dehydration, and embedding in resin. Tissue blocks are cut on an ultramicrotome using a diamond knife. Contact cement, applied to the block sides, ensures that serial sections stick together to form long ribbons. These are collected on coated coverslips, the coating having been engineered to tightly adhere to embedded-tissue sections, holding them flat for reliable autofocus and retaining them through multiple staining cycles. Arrays are stained using antibodies, lectins, or other reagents and detected by automated fluorescence microscopy, often at the diffraction limit. Antibodies can be stripped, and staining and imaging repeated multiple times to build up a high-dimensional data set from a given tissue volume. Arrays can also be stained with heavy metals and imaged by field-emission scanning electron microscopy (SEM). Images are stitched, aligned, and each light (and SEM) cycle merged into a 3D volume comprising all channels. Volumes can be analyzed, for example, to assess the spatial relationships among various markers, providing identification and characterization of synapses, cell types, and other features of interest.

Intact Tissue

The methods and systems described herein may be used to perform array tomography on an intact tissue sample. An intact tissue as described herein includes tissues that are sectioned on one dimension and contiguous in the other two dimensions. These tissues are characterized by minimal dissociation. An intact tissue sample is one wherein after sectioning, the sample retains tissue architecture and other cells normally found in the whole tissue. Exemplary methods of fixing intact tissue for the methods and systems described herein are provided in Example 1 below. Additionally methods of isolating and fixing intact tissue samples known to the skilled artisan can be employed for the methods and systems described herein. In some of the methods described herein, the intact tissue may be embedded in a resin such that the tissue can be sliced into sections of thickness between 20 and 1000 nm. In some cases, the sample is a paraffin-embedded tissue sample. In some cases, the sample is a formalin-fixed paraffin-embedded (FFPE) tissue sample. In some methods, the thickness of the section may be 25, 30, 35, 40, 45, 50, 55, 60, 70 80, 90 100, 150, 200, 250, 300, 350, 400, 450, 500, 550, 600, 650, 700, 750, 800, 850, 900, 950 or 1000 nm. In some methods, the thickness of the section may be about 100, 150, 200, 250, 300, 350, 400, 450, 500, 600, 700, 800, 900 or 1000 nm. In some cases, the method may not comprise dehydration of the intact tissue. In some cases, the tissue is not dehydrated and resin embedded. In some cases, a section collector is utilized to automatically collect ribbons produced on an ultramicrotome and place them on pre-defined regions of coated, precision coverslips, of sizes ranging from a microscope slide to a microtiter plate. Intact tissue samples that can be studied by this method may include for instance biopsied tissues for detection of one or more conditions.

Blocking and Washing of Off Target Background Signal in Tissue

Tissue heterogeneity can present a complex chemical environment that can cause non-specific background signal that obscures the specific biological signal. To reduce the undesired off-target signal, blocking solutions comprising mixtures of unlabeled single- or double-stranded nucleic acids, enzymes such as alkaline phosphatase, polymerases, ligases and nucleases, charged polymers such as PEG, charged polysaccharides such as heparin, and proteins such as BSA and casein, can be used. Blocking solutions can be added to any of the solutions used to label, stain, detect or wash the tissue during the procedure. Salt and pH levels can also be used to reduce or remove undesired, off-target background. Salt and pH levels in solutions can be used to improve specificity and/or signal strength. Salt and pH levels can also be used to remove unwanted background; for example, the use of chaotropic salts, such as salts of perchlorate, guanidium, urea or ions high on the Hofmeister series for the disruption of protein stability. Chemicals that can destabilize nucleic acid hybridization, such as formamide, urea or formaldehyde can also be used during labeling, staining, detection or washing to prevent or remove off target signals.

Array Tomography of Intact Tissue

Provided herein are methods comprising: contacting an intact tissue sample with at least one antibody that binds a particular protein, wherein said antibody is linked to a nucleic acid; and detecting said nucleic acid, thereby detecting the presence of said protein in the tissue sample. In an aspect, the methods may comprise contacting the intact tissue with a plurality of antibodies, wherein each antibody that hinds a specific protein is linked to a unique nucleic acid. In some cases each antibody in the plurality of antibodies may bind a different protein. The antibodies may be of the same or different isotypes, and the nucleic acids may comprise DNA and/or RNA. In some cases antibodies that bind different proteins may be of the same or different isotypes. In some methods, the at least one antibody maybe cross-linked to the tissue. In some cases, a method described herein may comprise contacting the intact tissue with a plurality of antibodies, wherein each antibody that binds a specific protein is linked to a unique nucleic acid.

Also provided herein are methods comprising contacting a target molecule in a sample with a detection couplet, wherein the detection couplet comprises a first nucleic acid and a second nucleic acid, wherein each nucleic acid has a target recognition region and a self-hybridization region, wherein the target recognition region of the first nucleic acid binds a first region of the target molecule, wherein the target recognition region of the second nucleic acid binds a second region of the target molecule, and wherein the self-hybridization region of the first nucleic acid and the self-hybridization region of the second nucleic acid are hybridized to form a double-stranded nucleic acid label. In some cases, the double-stranded nucleic acid label has an overhang. In some cases, the method further comprises contacting the double-stranded nucleic acid label with a DNA ligase. In some cases, the method further comprises contacting the double-stranded nucleic acid label with at least one detection label. In some cases, the at least one detection label is a double-stranded nucleic acid with an overhang that is complementary to the overhang of the double-stranded nucleic acid label. In some cases, the double-stranded nucleic acid label and the at least one detection label are ligated using the DNA ligase.

In some of the methods described herein, the detection of the plurality of antibodies may be spatially resolved. Some of the methods and systems described herein comprise use of a microfluidic chamber. Some methods may be fully automated.

Some methods described herein may be used to identify the protein composition of the tissue sample, and/or diagnose a physiological condition or disease as described above. Some methods maybe used to identify the tissue class of a particular intact tissue.

In some of the methods described herein, contacting the tissue with an antibody may comprise application of an electric field. In some cases, the electric field may be applied for about 1, 2, 3, 4, 5, 6, 7, 8, 9, 10, 12, 15, 20, 25, 30, 35, 40, 45, 50, 55, or 60 seconds. In some cases, the electric field maybe applied for between 0.5, 1, 1.5, 2, 2.5, 3, 3.5, 4, 4.5 or 5 minutes. In some cases, the electric field maybe applied for up to 5, 10, 15, 20, 25, 30, 35, 40, 45, 50, 55, 60, 65, 70, 75, 80, 85, or 90 minutes. In some cases, the electric field maybe applied between 1 and 60 minutes.

Also provided are systems suitable for carrying out the methods described herein, and kits for use with such systems.

Multiplex Detection Assay

The compositions, kits, methods, and systems disclosed herein can also be used in a detection assay (e.g., multiplex detection assay). In some cases, the detection assay can be used in a DNA microarray (e.g., for gene expression or SNP detection). In some cases, the detection assay can be used in serial analysis of gene expression (SAGE) (e.g., for gene expression). In some cases, the detection assay can be used in high-throughput sequencing (e.g., produce millions of short DNA sequences in parallel). In some cases, the detection assay can be used in multiplex polymerase chain reaction (PCR) (e.g., for applications requiring the amplification or sequencing of DNA or RNA). In some cases, the detection assay can be used in multiplex ligation-dependent probe amplification (MLPA). In some cases, the detection assay can be used in DNA sequencing by ligation. In some cases, the detection assay can be used in fluorescent microbead array.

In some cases, the detection assay can be used in protein microarray (e.g., for measuring protein-protein interactions or small molecule binding). In some cases, the detection assay can be used in antibody microarray (e.g., a type of protein array in which antibodies are arrayed). In some cases, the detection assay can be used in phage display (e.g., for screening large protein libraries for interacting proteins or other molecules). In some cases, the detection assay can be used in antibody profiling (e.g., multiple HLA antibody identification or reactivity prediction against a panel of organ donor population). In some cases, the detection assay can be used in Luminex/XMAP principle based multiplexing. In some cases, the detection assay can be used in binding antibody multiplex assay (BAMA) (e.g., for profiling multiple antibody isotypes and/or subclasses).

In some cases, the detection assay can be used in tissue microarray (e.g., for analyzing multiple tissue samples). In some cases, the detection assay can be used in cellular microarray (e.g., for observing cellular responses against a panel of materials). In some cases, the detection assay can be used in chemical compound microarray (e.g., for assaying multiple chemical compounds for specific activities). In some cases, the detection assay can be used in multiplex detection of western blot (e.g., for simultaneous detection of two or more targets on a western blot). In some cases, the detection assay can be used in multiplex biomarker analysis (e.g., for analyzing urine). In some cases, the detection assay can be used in enzyme-linked immunosorbent assay (ELISA) (e.g., for parallelized processing using microtiter plates). In some cases, the detection assay can be used in flow cytometry.

In some cases, the detection assay can simultaneously detect a plurality of targets in a sample using a detection assay. In some cases, the detection assay can simultaneously detect at least two targets, for example, at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 350, at least 400, at least 450, or at least 500 targets in a sample. In some cases, the detection assay can simultaneously detect from 2 to 500 targets, for example, from 2 to 5, from 2 to 10, from 2 to 100, from 2 to 500, from 5 to 10, from 5 to 100, from 5 to 500, from 10 to 100, from 10 to 500, or from 100 to 50 targets in a sample.

In some cases, the detection assay can detect a cell. In some cases, the cell can be a specific type of cell. In some cases, the cell can have a specific origin (e.g., from a specific organ). In some cases, the cell can have a specific status (e.g., healthy cell, cancer cell). In some cases, the detection assay can detect a plurality of targets in a sample. In some cases, the plurality of targets are a plurality of cells. In some cases, the plurality of cells are different types of cells. In some cases, the plurality of cells have different origins (e.g., from different organs). In some cases, the plurality of cells have different status (e.g., healthy cells, cancer cells).

In some cases, the detection assay can detect a target molecule. The target molecule can be any molecule of interest in the sample. The target molecule can be a carbohydrate, a lipid, a protein, or a nucleic acid (e.g., DNA or RNA). The target molecule can be a RNA molecule, for example, an mRNA, a tRNA, a rRNA, a snRNA, or an non-coding RNA molecule.

In some cases, the target molecule can be a cellular molecule. In some cases, the cellular molecule can be a molecule inside a cell membrane that separates the interior of all cells from the outside environment. In some cases, the cellular molecule can be a carbohydrate, a lipid, a protein, or a nucleic acid (e.g., DNA or RNA).

In some cases, the target molecule can be a cell surface molecule. In some cases, the cell surface molecule can be a molecule on a cell membrane that separates the interior of all cells from the outside environment. In some cases, the cell surface molecule can be a carbohydrate, a lipid, a protein, or a nucleic acid (e.g., DNA or RNA).

In some cases, the detection assay can detect a protein. In some cases, the detection assay can detect a plurality of proteins. In some cases, the proteins can be cytoskeletal proteins, such as Actin, Arp2/3, Formin, Coronin, Dystrophin, FtsZ, Keratin, Myosin, and Tubulin. In some cases, the proteins can be extracellular matrix proteins, such as Collagen, Elastin, F-spondin, Pikachurin, and Fibronectin. In some cases, the proteins can be plasma proteins, such as Serum Amyloid P Component and Serum albumin. In some cases, the proteins can be coagulation factors, such as Complement proteins (e.g., C1-inhibitor, C3-convertase), Factor VIII, Factor XIII, Protein C, Protein S, Protein Z, Protein Z-related protease inhibitor, Thrombin, and Von Willebrand Factor. In some cases, the proteins can be Acute phase proteins (e.g., C-reactive protein). In some cases, the proteins can be Hemoproteins, such as Hemoglobin (e.g., oxyhemoglobin, deoxyhemoglobin). In some cases, the proteins can be Cell adhesion, such as Cadherin, Ependymin, Integrin, NCAM, and Selectin. In some cases, the proteins can be transmembrane transport proteins, such as CFTR, Glycophorin D, and Scramblase. In some cases, the proteins can be ion channels. In some cases, the proteins can be ligand-gated ion channels, such as Nicotinic acetylcholine receptor and GABAa receptors. In some cases, the proteins can be voltage-gated ion channels, such as Potassium channels, Calcium channels, and Sodium channels. In some cases, the proteins can be Synport/Antiport proteins, such as glucose transporter. In some cases, the proteins can be hormones or growth factors. In some cases, the proteins can be growth factors, such as Colony-stimulating factors (CSFs), Epidermal growth factor (EGF), Fibroblast growth factor (FGF), Platelet-derived growth factor (PDGF), Transforming growth factors (TGFs), and Vascular endothelial growth factor (VEGF). In some cases, the proteins can be peptide hormones, such as Insulin, Insulin-like growth factor (IGF), and Oxytocin. In some cases, the proteins can be receptors. In some cases, the proteins can be transmembrane receptors, such as G-protein-coupled receptor (e.g., rhodopsin). In some cases, the proteins can be intracellular receptors, such as Estrogen receptor. In some cases, the proteins can be DNA-binding protein, such as Histones and Protamines. In some cases, the proteins can be transcription regulatory proteins, such as C-myc, FOXP2, FOXP3, MyoD, and P53. In some cases, the proteins can be RNA-binding proteins, such as SRRT. In some cases, the proteins can be immune system proteins, such as Immunoglobins, Major histocompatibility antigens, and T cell receptors. In some cases, the proteins can be nutrient storage or transport proteins, such as Ferritin. In some cases, the proteins can be chaperone proteins, such as GroEL. In some cases, the proteins can be enzymes.

Genome Editing Applications

The compositions, kits, methods, and systems disclosed herein can also be used in a genome editing assay. The genome editing assay can be a CRISPR (Clustered Regularly Interspaced Short Palindromic Repeats) assay. The genome editing assay can be a CRISPR/Cas (CRISPR-associated protein) nuclease assay. The genome editing assay can be a Zinc finger nucleases (ZFN) assay. The genome editing assay can be a TAL-effector nuclease (TALEN) assay. The genome editing assay can be a meganuclease assay. The genome editing assay can be an NgAgo (*Naironobacterium gregoryi* Argonaute) assay.

The compositions, kits, methods, and systems disclosed herein can detect a component in the CRISPR (e.g., CRISPR/Cas) assay. In some cases, the component can be a Cas nuclease or a variant thereof. The Cas nuclease can direct cleavage of one or both strands at a location in a target DNA sequence. For example, the Cas nuclease can be a nickase having one or more inactivated catalytic domains that cleaves a single strand of a target DNA sequence. Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, homologs thereof, variants thereof, mutants thereof, and derivatives thereof.

In some cases, the component can be a target DNA. In some cases, the component can be a DNA-targeting RNA (e.g., a single guide RNA or sgRNA) containing a guide sequence that targets Cas9 to the target genomic DNA. In some cases, the component can be a scaffold sequence that interacts with Cas9, such as a trans-activating crRNA (tracrRNA). In some cases, the component can be a donor repair template. The nucleotide sequence encoding the DNA-targeting RNA can be cloned into an expression cassette or an expression vector. In some embodiments, the nucleotide sequence is produced by PCR and contained in an expression cassette. For instances, the nucleotide sequence encoding the DNA-targeting RNA can be PCR amplified and appended to a promoter sequence, e.g., a U6 RNA polymerase III promoter sequence. In other embodiments, the nucleotide sequence encoding the DNA-targeting RNA is cloned into an expression vector that contains a promoter, e.g., a U6 RNA polymerase III promoter, and a transcriptional control element, enhancer, U6 termination sequence, one or more nuclear localization signals, etc. In some embodiments, the expression vector is multicistronic or bicistronic and can also include a nucleotide sequence encoding a fluorescent protein, an epitope tag and/or an antibiotic resistance marker. In certain instances of the bicistronic expression vector, the first nucleotide sequence encoding, for example, a fluorescent protein, is linked to a second nucleotide sequence encoding, for example, an antibiotic resistance marker using the sequence encoding a self-cleaving peptide, such as a viral 2A peptide. 2A peptides including foot-and-mouth disease virus 2A (F2A); equine rhinitis A virus 2A (E2A); porcine teschovirus-1 2A (P2A) and Thoseaasigna virus 2A (T2A) have high cleavage efficiency such that two proteins can be expressed simultaneously yet separately from the same RNA transcript.

The compositions, kits, methods, and systems disclosed herein can detect a component in the NgAgo assay. In some cases, the component can be an endonuclease. In some cases, the component can be an Argonaute endonuclease. In some cases, the component can be a single-stranded DNA (ssDNA). In some cases, the component can be a guide ssDNA. In some cases, the component can be a 5' phosphorylated ssDNA (gDNA). In some cases, the gNDA can be from about 10 to about 100 nucleotides, for example, from about 10 to about 20 nucleotides, from about 10 to about 40 nucleotides, from about 10 to about 60 nucleotides, from about 10 to about 80 nucleotides, from about 10 to about 100 nucleotides, from about 20 to about 40 nucleotides, from about 20 to about 60 nucleotides, from about 20 to about 80 nucleotides, from about 20 to about 100 nucleotides, from about 40 to about 60 nucleotides, from about 40 to about 80 nucleotides, from about 40 to about 100 nucleotides, from about 60 to about 80 nucleotides, from about 60 to about 100 nucleotides, or from about 80 to about 100 nucleotides. In some cases, the gNDA can be about 20 nucleotides. In some cases, the gNDA can be about 24 nucleotides. In some cases, the gNDA can be about 30 nucleotides.

Conditions or Diseases

Physiological conditions or diseases can be diagnosed by the methods provided herein by the identification of target molecules (e.g., protein, mRNA) associated with such conditions or diseases. In some cases, the target molecules can be found in the intact tissue sample. The conditions or diseases can include, for instance, kidney diseases such as crescentic glomerulonephritis, infectious diseases that can be diagnosed by studying biopsied lymph node tissue, metabolic diseases including amyloidosis, and fertility levels as may be detected from testicular biopsies. Pre-cancerous and cancerous conditions can be identified by applying the methods described herein to biopsied intact tumor tissues. Other tissues that are generally studied by biopsies can be analyzed by the methods and systems described herein, for instance, bone marrow, gastrointestinal tract, lung, liver, prostate, nervous system, urogenital system, brain, breast, muscle and skin.

In some cases, the conditions or diseases can also include brain disorders, for instance, Acoustic Neuroma, Acquired Brain Injury, Agenesis Corpus Callosum, Alzheimer's Disease, Amyotrophic Lateral Sclerosis, Aneurysm, Aphasia, Arteriovenous Malformation, Attention Deficit Hyperactivity Disorder (ADHD), Autism, Batten Disease, Behcet's Disease, Blepharospasm, Brain Tumour and/or Cancer, Cerebral Lupus, Cerebral Palsy, Cervical Dystonia, Charcot-Marie-Tooth Disorder, Chiari Malformation, Chronic Inflammatory Demyelinating Polyneuropathy, Coma, Concussion, Creutzfeldt-Jakob Disease, Dementia (Non-Alzheimer Type), Down Syndrome, Dysautonomia, Dyslexia, Dyspraxia, Dystonia, Encephalitis, Epilepsy, Essential Tremor, Friedreich's Ataxia, Gaucher Disease, Guillain-Barre Syndrome, Huntington's Disease, Hydrocephalus, Intracranial Hypertension, Leukodystrophy, Locked-In Syndrome (LiS), Meniere's Disease, Meningitis, Meningococcal Disease, Migraine, Minimally Conscious State, Motor Neurone Disease, Multiple Sclerosis, Multiple System Atrophy, Muscular Dystrophy, Myasthenia Gravis, Narcolepsy, Parkinson's Disease, Peripheral Neuropathy, Prader-Willi Syndrome, Progressive Supranuclear Palsy, Restless Legs Syndrome, Rett Syndrome, Shy Drager Syndrome, Sleep Disorders, Spasmodic Dysphonia, Stroke, Subarachnoid Haemorrhage, Sydenham's Chorea, Tay-Sachs Disease, Tourette Syndrome, Transient Ischaemic Attack, Transverse Myelitis, Traumatic Brain Injury, Trigeminal Neuralgia, Tuberous Sclerosis, Vegetative State, and Von Hippel-Lindau Syndrome.

In some cases, the conditions or diseases can also include cancer. The cancer may be a recurrent and/or refractory cancer. Examples of cancers include, but are not limited to, sarcomas, carcinomas, lymphomas or leukemias.

In some cases, sarcomas are cancers of the bone, cartilage, fat, muscle, blood vessels, or other connective or supportive tissue. Sarcomas can include, but not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angio sarcoma, cystosarcoma phylloides, dermatofibrosarcoma, desmoid tumor, epithelioid sarcoma, extraskeletal osteosarcoma, fibrosarcoma, hemangiopericytoma, hemangio sarcoma. Kaposi's sarcoma, leiomyosarcoma, liposarcoma, lymphangio sarcoma, lymphosarcoma, malignant fibrous histiocytoma, neurofibrosarcoma, rhabdomyo sarcoma, and synovial sarcoma).

In some cases, carcinomas are cancers that begin in the epithelial cells, which are cells that cover the surface of the body, produce hormones, and make up glands. Carcinomas can include, but not limited to, breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers can include non-small cell lung carcinoma (NSCLC), small cell lung carcinoma, and mesotheliomia. Examples of NSCLC can include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

The cancer may be a central nervous system (CNS) tumor. CNS tumors may be classified as gliomas or nongliomas. The glioma may be malignant glioma, high grade glioma, diffuse intrinsic pontine glioma. Examples of gliomas can include astrocytomas, oligodendrogliomas (or mixtures of oligodendroglioma and astocytoma elements), and ependymomas. Astrocytomas can include, but not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas can include low-grade oligodendrogliomas (or oligoastrocytomas) and anaplastic oligodendriogliomas. Nongliomas can include meningiomas, pituitary adenomas, primary CNS lymphomas, and medulloblastomas. The cancer may be a meningioma.

Lymphomas can be cancers of the lymphocytes and may develop from either B or T lymphocytes. The two major types of lymphoma can be Hodgkin's lymphoma, previously known as Hodgkin's disease, and non-Hodgkin's lymphoma. Hodgkin's lymphoma can be marked by the presence of the Reed-Sternberg cell. Non-Hodgkin's lymphomas can be all lymphomas which are not Hodgkin's lymphoma. Non-Hodgkin lymphomas may be indolent lymphomas and aggressive lymphomas. Non-Hodgkin's lymphomas can include, but not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The leukemia may be an acute lymphocytic leukemia, acute myelocytic leukemia, chronic lymphocytic leukemia, or chronic myelocytic leukemia. Additional types of leukemias can include hairy cell leukemia, chronic myelomonocytic leukemia, and juvenile myelomonocytic leukemia.

The diseases and/or conditions can include, but not limited to, atherosclerosis, inflammatory diseases, autoimmune diseases, rheumatic heart disease. Examples of inflammatory diseases include, but are not limited to, acne vulgaris. Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

In some cases, the conditions or diseases can be autoimmune diseases including, but not limited to, acute disseminated encephalomyelitis (ADEM), Addison's disease, agammaglobulinemia, alopecia areata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's diseasevDercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditisv Henoch-Schonlein purpuravherpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Meniere's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome. Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis *nodosa*, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The compositions, kits, methods, and systems disclosed herein may also be useful for detecting, monitoring, diagnosing and/or predicting a subject's response to an implanted device. Exemplary medical devices can include but not limited to stents, replacement heart valves, implanted cerebella stimulators, hip replacement joints, breast implants, and knee implants.

The compositions, kits, methods, and systems disclosed herein may also be useful for detecting, monitoring, quantitating, or evaluating one or more pathogen-derived nucleic acid molecules or one or more diseases or conditions caused by one or more pathogens. Exemplary pathogens can include, but not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. Additional pathogens can include, but not limited to, *Mycobacterium tuberculosis, Streptococcus, Pseudomonas, Shigella, Campylobacter,* and *Salmonella*.

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections can include, but not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus can include, but not limited to, jock itch, yeast infection, ringworm, and athlete's foot.

The pathogen may be a virus. Examples of viruses can include, but not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses can include, but not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Computer Control System

Figure 6:
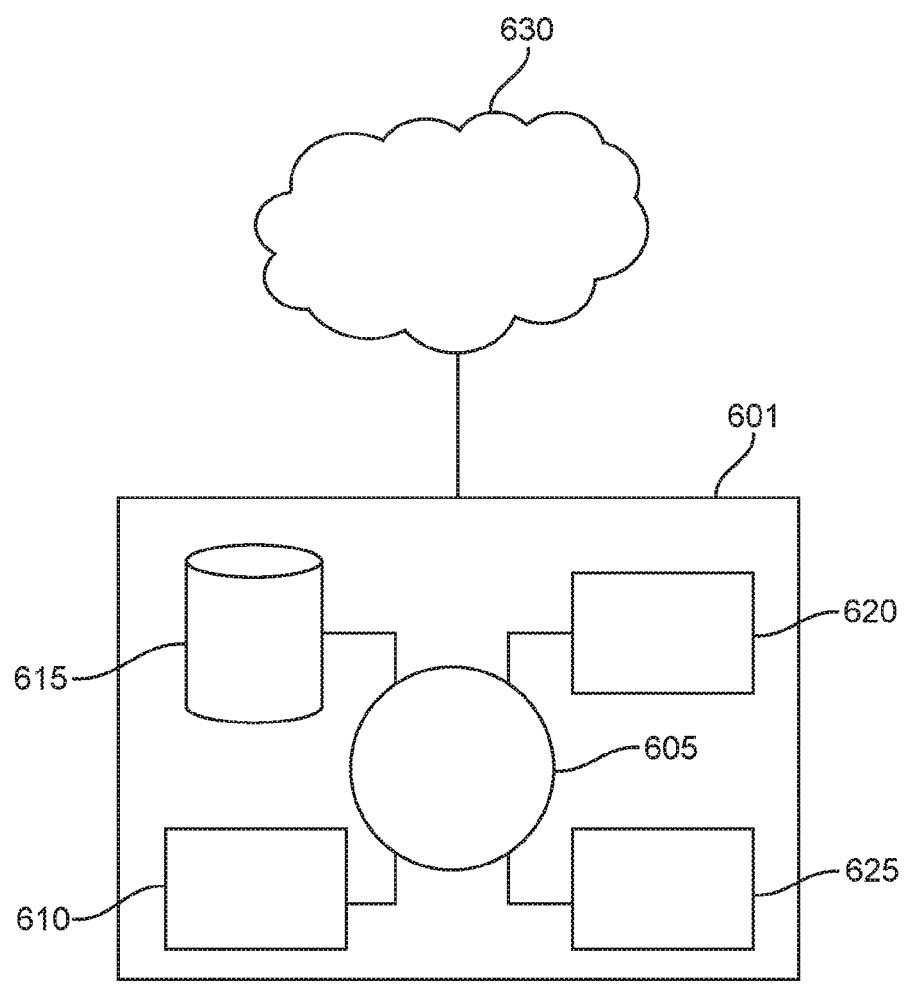
FIG. 6 schematically illustrates an example control system implementing methods of the present disclosure.

The present disclosure provides computer control systems that are programmed to implement methods of the disclosure. FIG. 6 shows a computer system 601 that is programmed or otherwise configured to analyze genotype data according to methods of the disclosure. The computer system 601 can regulate various aspects of genotype analysis of the present disclosure, such as, for example, analysis by inheritance pattern scores, and/or analysis by association pattern scores.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. Examples of operations performed by the CPU 605 can include fetch, decode, execute, and writeback. The CPU 605 can be processor that is programmed for performing the methods of feature-based ranking of genes (FROG), variant inheritance pattern ranking (VIPR), determining segregation patterns, determining inheritance patterns, determining association scores, and ranking phenotypes, genotypes and any data associated with the methods of the disclosure.

The storage unit 615 can store files, such as drivers, libraries and saved programs. The storage unit 615 can store programs generated by users and recorded sessions, as well as output(s) associated with the programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 401, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display that comprises a user interface (UI) for providing, for example, a display, graph, chart and/or list in graphical and/or numerical form of the genotype analysis according to the methods of the disclosure, which may include inheritance analysis, causative variant discovery analysis, and diagnosis. Examples of UI's include, without limitation, a graphical user interface (GUI) and web-based user interface.

The data generated by the ranking can be displayed (e.g., on a computer). The data can be displayed in a numerical and/or graphical form. For example, data can be displayed as a list, as statistics (e.g., p-values, standard deviations), as a chart (e.g., pie chart), as a graph (e.g., line graph, bar graph), as a histogram, as a map, as a heat map, as a timeline, as a tree chart, as a flowchart, as a cartogram, as a bubble chart, a polar area diagram, as a diagram, as a stream graph, as a Gantt chart, as a Nolan chart, as a smith chart, as a chevron plot, as a plot, as a box plot, as a dot plot, as a probability plot, as a scatter plot, and as a biplot, or any combination thereof.

Subjects

Often, the methods are used on a subject, preferably human. The subject may be a male or a female. The subject may be a fetus, infant, child, adolescent, teenager or adult. The subject may be patients of any age. For example, the subject may be a patient of less than about 10 years old. For example, the subject may be a patient of at least about 0, 5, 10, 20, 30, 40, 50, 60, 70, 80, 90, or 100 years old. The subject may be in utero. Often, the subject is a patient or other individual undergoing a treatment regimen, or being evaluated for a treatment regimen (e.g., immunosuppressive therapy). However, in some instances, the subject is not undergoing a treatment regimen. For example, the subject may be a healthy subject.

In some cases, the subjects may be mammals or non-mammals. Preferably, the subjects are a mammal, such as, a human, non-human primate (e.g., apes, monkeys, chimpanzees), cat, dog, rabbit, goat, horse, cow, pig, rodent, mouse, SCID mouse, rat, guinea pig, or sheep. In some methods, species variants or homologs of these genes can be used in a non-human animal model. Species variants may be the genes in different species having greatest sequence identity and similarity in functional properties to one another. Many of such species variants human genes may be listed in the Swiss-Prot database.

The methods disclosed herein may be used on a transplant recipient who is a recipient of a solid organ or a fragment of a solid organ. The solid organ may be a lung, kidney, heart, liver, pancreas, large intestine, small intestine, gall bladder, reproductive organ or a combination thereof. In some instances, the transplant recipient may be a recipient of a tissue or cell. The tissue or cell may be amnion, skin, bone, blood, marrow, blood stem cells, platelets, umbilical cord blood, cornea, middle ear, heart valve, vein, cartilage, tendon, ligament, nerve tissue, embryonic stem (ES) cells, induced pluripotent stem cells (IPSCs), stem cells, adult stem cells, hematopoietic stem cells, or a combination thereof.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Example 1. Tissue Preparation

Generally tissue preparation methods outlined in Micheva, K. D., O'Rourke, N., Busse, B., & Smith, S. J. (2010). Array Tomography: Rodent Brain Fixation and Embedding. Cold Spring Harbor Protocols, 2010(11), were used (by adapting and optimizing for the difference in the tissue type and the organism from which the tissue is obtained).

Mouse brain was dissected and fixed as follows:

Dissection tools were set up and PBS and filtered fixative were prepared, ready to flow, without air bubbles. 2% glutaraldehyde and 2% depolymerized paraformaldehyde, were dissolved in 0.1 M phosphate buffer, with pH between 6.8 and 7.2.

The rodent was anesthetized without killing, the heart was exposed and the right atrium was cut and a cannula inserted into the left ventricle. A blunted ~20 G needle, shortened to about 1 cm was used. In some cases, for organisms where the aorta is not fragile or easily destroyed, it is optimal to cannulate the aorta. The fixative was then allowed to flow for about 10 minutes by use of gravity flow; or in some instances a perfusion pump. This was then perfused with up to 5 ml of PBS.

About 5 cc of heparinized saline was then put in the tube, to help flush blood. Perfusion with fixative was performed for 10 minutes. The brain was removed within 20 minutes of fixation. The whole brain was postfixed in the same fixative overnight in the refrigerator. After rinsing 2× in 0.1M Phosphate buffer, the tissue was stored up to one week at 4° C.

In certain cases, thick tissue sections are analyzed, approximately 200 nm-1 µm for resin-embedded tissue. It is noted that thick sections allow imaging larger volumes per unit time. Imaging may be performed at high magnification or with relatively low magnification objectives, 10-20×. For instance in the analysis of biopsied tissues such as tumors, it may be preferred to perform analysis of thick sections at lower magnifications. The lower magnification allows analysis of large fields of tissue with subcellular resolution.

In some cases, the tissue is not dehydrated and resin embedded, rather the labeling methods described below are applied to antibodies that have been validated for staining of fixed, hydrated tissue.

In some cases, a section collector is utilized to automatically collect ribbons produced on an ultramicrotome and place them on pre-defined regions of coated, precision coverslips, of sizes ranging from a microscope slide to a microtiter plate.

Example 2. Ligation Amplified Multiplexed Detection Antigens (LAMDA)

Reagents:
1. DNA conjugated Antibodies
2. Antisense detection oligomers with sticky overhang (e.g., GGG)
3. Double Stranded oligomers (DSO) with 5' phosphate, internal fluorophore (e.g., Alexa 594) and terminal sticky ends (e.g., 5' CCC & 3' GGG)
4. T4 DNA ligase—Ligase Solution with PEG
5. Restriction endonucleases—Used to remove the fluorophores. The DSO's are designed so that a unique endonuclease can remove a specific color (e.g., CCCGGG=SMA1). Endonucleases with 100% activity at room temperature is use (e.g., SMA1, BamH1 & Sac1)
6. Tris buffer—0.05M Tris with 0.1% Tween and 50 mM Glycine—made in nuclease free water, then autoclaved
7. Roche Blocking Reagent for nucleic acid hybridization and detection (Sigma 11096176001)—10% (w/v) stock [10×]
8. Glutaraldehyde
9. Sodium Borohydride
10. Nuclease-free water Procedure:
1. Pre-Block—place tissue in Tris buffer in 1% (w/v) [1×] Blocking Reagent for 1 min.
2. Antibody Stain—Dilute DNA-Antibody in Tris buffer in 1% (w/v) [1×] Blocking Reagent Overnight. Concentration of antibody is determined on an antibody to antibody basis.
3. Primary Wash—Wash tissue in Tris buffer, 1 min each 3 times. Finish by washing with Nuclease Free Water 1 time (do not need to incubate). If >3 DNA-antibodies are used, i.e., multi-detection rounds are expected, fix with 1% gluteraldehyde in water for 1 min. Wash with Water 1 min, then treat the tissue with 1% Sodium Borohydride in Tris (Without Tween and Glycine) for 1 min (to remove autofluorescence). Wash with water 1 min.
4. DNA Hybridization (All steps at room temperature)—Dilute antisense detection oligomers in Ligase buffer to a final concentration of 100 nM. Place ligase buffer on tissue. Meanwhile, prepare a 2× concentration 200 nM DSO in ligase buffer at the same volume as the detection oligo solution on tissue.
5. Ligation Reaction—Put 1 ul T4 DNA ligase per 20 ul solution with tissue oligo mixture, then add the DSO ligase buffer mixture and mix. Let stand for 5 min.
6. Secondary Wash—Wash tissue with Nuclease Free Water, followed by 1 min each 3 times wash of Tris buffer.
7. Mount and Image—Wash again with Water, then mount sample and image.
8. Wash and destain—Wash with Nuclease Free Water, place restriction endonucleases in digest buffer on tissue and incubate for 5 min. Follow with a Water wash.
9. Restain—If there are other DNA-Antibodies to be imaged, restart DNA Hybridization.

Cleavable Linkers
1. Cleavage in 2% hydrazine in phosphate buffer; 30-120 min, RT: Dde
2. Cleavage in 10 mM sodium periodate (NaIO4) phosphate buffer; 20 min, RT, dark; diol
3. Cleavage in 50 mM sodium dithionite (Na2S204); diazo Example 3. Ligation Amplification with Phosphatase and Sonicated DNA Block Similar reagents and protocols as described in Examples 1 and 2 were used in this example.

As shown in FIGS. 7A to 7J, ligation amplification with phosphatase and sonicated DNA block improved signal to noise ratio. FIG. 7A show the max projection of DNA-tagged acetylated tubulin from 10 (70 nm) sections. FIG. 7A shows DNA-labeled primary visualized via ligation oligomerization. FIG. 7B shows the same DNA-primary visualized by traditional fluorescent secondary in the same tissue sections. FIG. 7C shows DNA-labeled primary visualized with fluorescently labeled antisense oligomers in the same tissue as FIGS. 7A and 7B. FIGS. 7D-7F show the close-up views of FIGS. 7A-7C (as highlighted by yellow box). White arrowheads in FIG. 7D shows point to off-target ligation visualization of nucleus, which are absent in FIG. 7E (white arrowheads). FIG. 7F shows antisense detection also incurred off-target signal, although the nucleus has lesser labeling. FIGS. 7G-7I show in different tissue, DNA-labeled synapsin antibody is visualized post phosphatase and sonicated DNA block. FIG. 7G shows significant decrease in nuclear labeling, bringing off-target labeling (white arrowheads) on par with secondary detection FIG. 7H (white arrowheads). FIG. 7I shows the sonicated DNA block also improved antisense detection noise. FIG. 7J shows the superimposed intensity histograms of each method on logarithmic scale.

Example 4. Deep Multiplexing Using DNA Conjugated Antibodies

Similar reagents and protocols as described in Examples 1 and 2 were used in this example.

Figure 8:
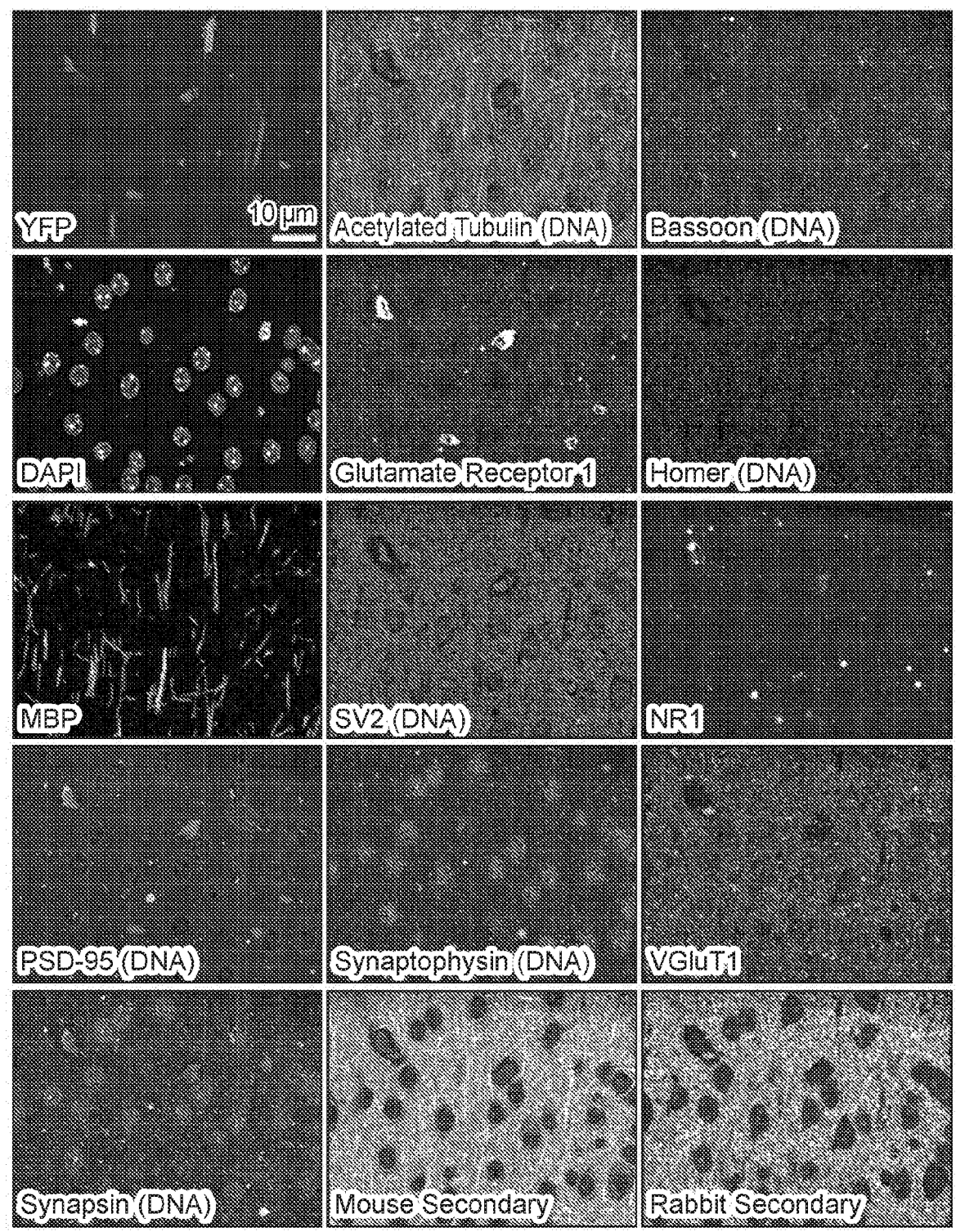
FIG. 8 illustrates the panels that contain projection of 27 sections in cortex.

FIG. 8 shows the panels that contain projection of 27 sections in cortex. All proteins marked (DNA) were detected using fluorescently labeled DNA oligomers. GluR1 (rabbit) and NR1 (mouse) were detected first using secondary antibodies, the primaries having been applied to the tissue and fixed with glutaraldehyde. All other antibodies were simultaneously incubated then fixed to tissue using glutaraldehyde. VGluT1 (guinea pig) and MBP (chicken) were detected using the appropriate species-specific antibody. Each antibody presented similar patterns individually and under the dense-labeling condition. Final application of mouse and rabbit antibodies shows the dense labeling of tissue by all antibodies in this panel.

Example 5. Deep Multiplexing Targeting 9 Antibodies

Similar reagents and protocols as described in Examples 1 and 2 were used in this example.

Figure 9:
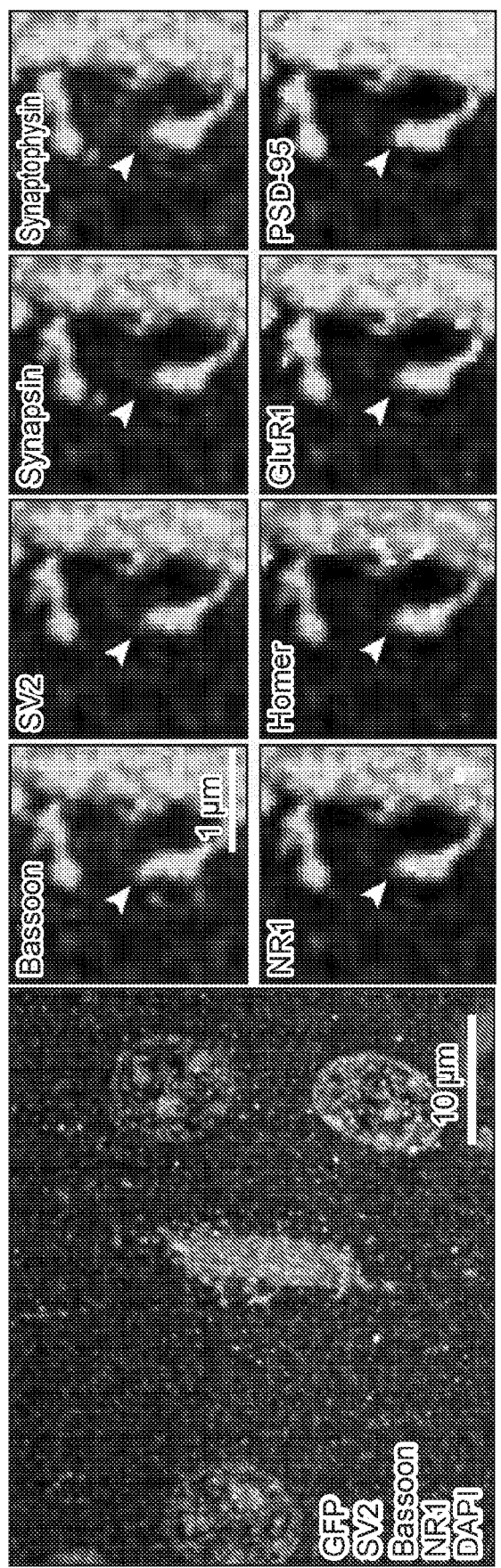
FIG. 9 illustrates the simultaneous targeting the same structure (cortical synapse) using nine antibodies.

This example (shown in FIG. 9) demonstrated that simultaneous targeting the same structure (cortical synapse) using 9 antibodies did not affect antibody labeling and did not disrupt tight protein detection around synapse. The 9 antibodies are: 2 presynaptic scaffolding proteins (Bassoon, Synapsin), 3 presynaptic vesicular proteins (Synaptic Vesicle Protein 2, Synaptophysin, Vesicular Glutamate Transporter 1), 2 post-synaptic scaffolding proteins (Homer, Post-synaptic Density Protein 95), and 2 post-synaptic receptor proteins (Glutamate Receptor 1, NMDA Receptor 1).

The protein markers that define pre- and post-synaptic structures labeled under dense condition (9 simultaneous targeting the same structure) as it did on as a single label. Furthermore, the acquisition of this 18 protein channel data using our current method required only a single day with multiple imaging sessions, whereas using tradition array tomography methods (Micheva, et. al.) this would have taken a week.

Example 6. Fast Detection of Multiplexed Antigens Using Tag Sequencing

Similar reagents and protocols as described in Examples 1 and 2 were used in this example.

In some cases, tag sequencing by hybridization is employed. This is a variant of direct sequencing uses tags that are about 60 base pairs (bp) consisting of 4 about 15mer units. With this approach, the number of unique combinations is 4n, or 256 for n=4. For the detection of for instance 100 proteins in a tissue sample, each of the 100 antibodies has a tag consisting of 4 unique 15mers (corresponding to A, T, C or G) at each of the positions, requiring 16 unique oligomers, in total. The 'sequencing' could be from either end. All that is required is that when sequencing position m, the 4 oligomers that are complementary to the tag oligomers in position m are introduced. For example, oligomers, each labeled with a distinguishable fluorophore, complementary to the 4 unique sequences on the distal end of the tags, are introduced and read out; the fluorophores are then removed, either by cleaving the linker, or by enzymatically cleaving the dsDNA to release the fluorophore. The latter method requires sequencing from the distal end. Because this tag-sequencing method allows using each fluorophore in each round, the formula for the number of unique tags is pn (p=number of fluorescent channels, n=number of reads) (above we assumed p=4 as shown in FIG. 10).

For example in FIGS. 10A-D, an example of fast detection of multiplexed antigens using tag sequencing is shown. FIGS. 10A-C show sequential detection of oligomer modules followed by removal of the fluorescently labeled oligomers by restriction endonuclease cleavage. FIG. 10D shows using the color combinations generated across imaging cycles, final images for each antigen are reconstructed. The potential number of unique antigens is pn (p=number of fluorescent channels, e.g., unique detection oligomers; n=number of modules). In FIG. 10, there are 3 modules and 3 fluorescent channels, thus 33=27 potential antigens. By increasing either the module number of fluorescent channel number, we could easily image hundreds of antigens in a short amount of time, e.g., 4 module groups and 4 fluorescent channels=256 potential antigens.

Tag 'sequencing' by hybridization works well with QD-labeled oligomers. Using QDs allows increasing p, from 4 to 6, or more. Assuming p=6, and n=3, 216 antibodies could be uniquely labeled, using only 6×3=18, unique oligomers and 3 reads. Using QDs enables reasonably high-speed STORM-like imaging. It has been demonstrated that one can take advantage of quantum dot blinking to obtain three-dimensional super-resolution imaging with ~15 nm in the plane. Further, the quantum dots do not need to be photo-activated, are resistant to photobleaching, and require a single color for excitation.

Example 7. Multi-Round Sequencing of Single Antibody

Similar reagents and protocols as described in Examples 1 and 2 were used in this example.

Antibodies with long DNA tags were generated using the method in Example 6, imaged through sequential reads, and obtained good read-to-read consistency between individual tags. Merging the images allowed us to uniquely identify single antigens (shown in FIGS. 11A-E).

Figure 11A:
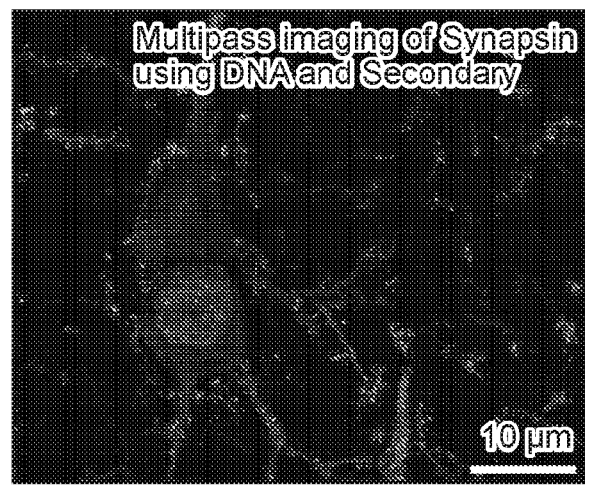
FIG. 11A illustrates the synapsin labels surrounding GFP labeled neurons.
Figure 11B:
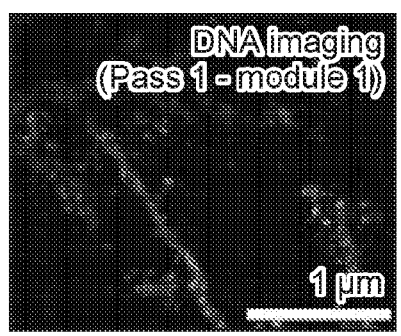
FIG. 11B illustrates the pass one detection of synapsin using fluorescent DNA oligomers.
Figure 11C:
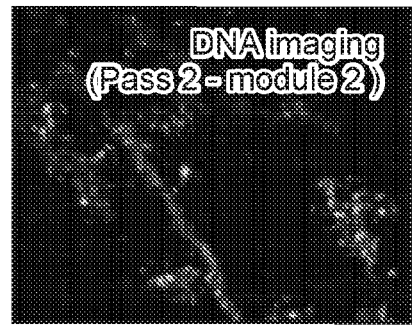
FIG. 11C illustrates the pass two detection of synapsin using fluorescent DNA oligomers.
Figure 11D:
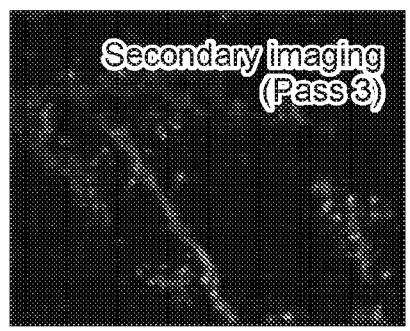
FIG. 11D illustrates the pass three detection of synapsin using secondary antibody.
Figure 11E:
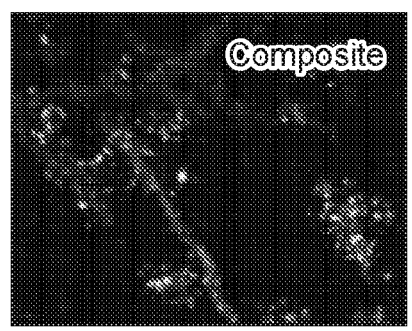
FIG. 11E illustrates the composite of all three passes.

FIG. 11A shows the synapsin labels surrounding GFP labeled neurons. The synapsin labels around the GFP dendrite and cell body were computationally highlighted using a dilated version of the GFP label as a mask to extract the synapsin puncta from the total volume. FIG. 11B shows the pass one detection of synapsin using fluorescent DNA oligomers. Using secondary detection of the same synapsin stain as fiducial, it was determined that 103761 out of 111970 secondary labeled synapsin puncta were detected (or a 7.3% false negative rate) using DNA. There was also a 3.9% false positive rate where DNA labeled puncta did not correspond to a secondary labeled puncta (shown in FIG. 11D). FIG. 11C shows the pass two detection of synapsin using fluorescent DNA oligomers. Compared to secondary (shown in FIG. 11D), pass two had a 9.5% false negative rate and a 3.5% false positive rate. Compared to first pass, pass two had a 5% false negative rate and a 2.4% false positive rate. FIG. 11E shows the composite of all three passes.

This example demonstrated that "tag sequencing" was indeed possible even without one-to-one DNA antibody conjugation and super-resolution imaging and the method can be used to image highly multiplexed antigens without the use of difficult and inefficient chemistry or complicated imaging methods.

Example 8. Visualizing Antigen in Thick Paraffin Sections of Tumor Tissue Using DNA Conjugated Antibodies Similar reagents and protocols as described in Examples 1 and 2 were used in this example.

This example demonstrated that the method disclosed herein is useful beyond thin (50-100 nm) resin-embedded tissue. Samples in this example were obtained on thicker paraffin-embedded tissue sections (5-20 um) (e.g., formalin-fixed paraffin-embedded (FFPE) tissue), which are commonly used in cancer research and diagnostic applications. Using an antibody against acetylated tubulin, it was demonstrated that the detection methods revealed a density of acetylated tubulin in the cellularly differentiated normal brain tissue while the less differentiated cancer cells did not express this stable form of tubulin.

Figure 12A:
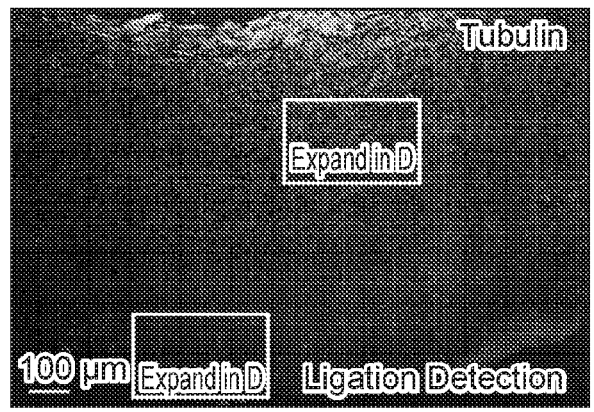
FIG. 12A illustrates the acetylated tubulin visualized using DNA conjugated anti-ac Tubulin antibody obtained on 10 um paraffin sections (e.g., formalin-fixed paraffin-embedded (FFPE) tissue).
Figure 12B:
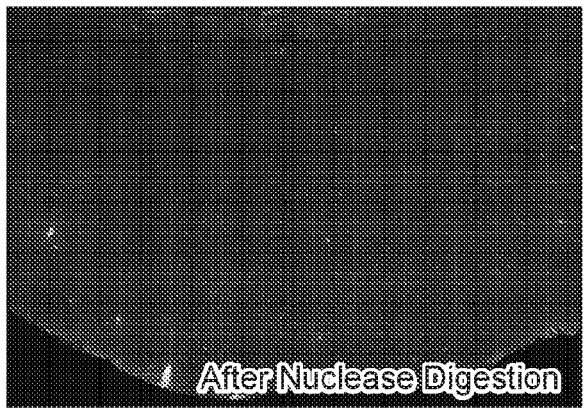
FIG. 12B illustrates that the same section after 30 min in endonuclease solution removed acetylated tubulin signal.
Figure 12C:
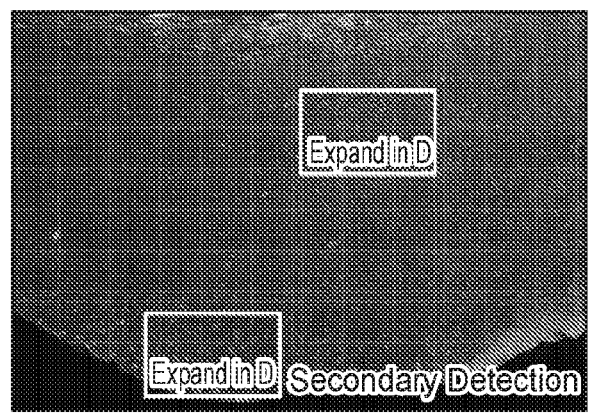
FIG. 12C illustrates that the same tissue restained using secondary antibodies.
Figure 12D:
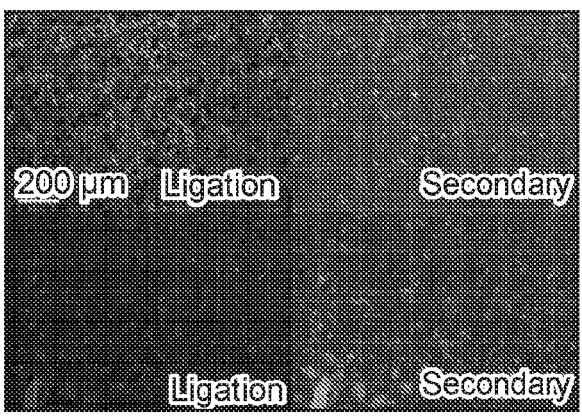
FIG. 12D illustrates the close-up view of the acetylated tubulin structures in the yellow boxes from FIGS. 12A and 12C.
Figure 12E:
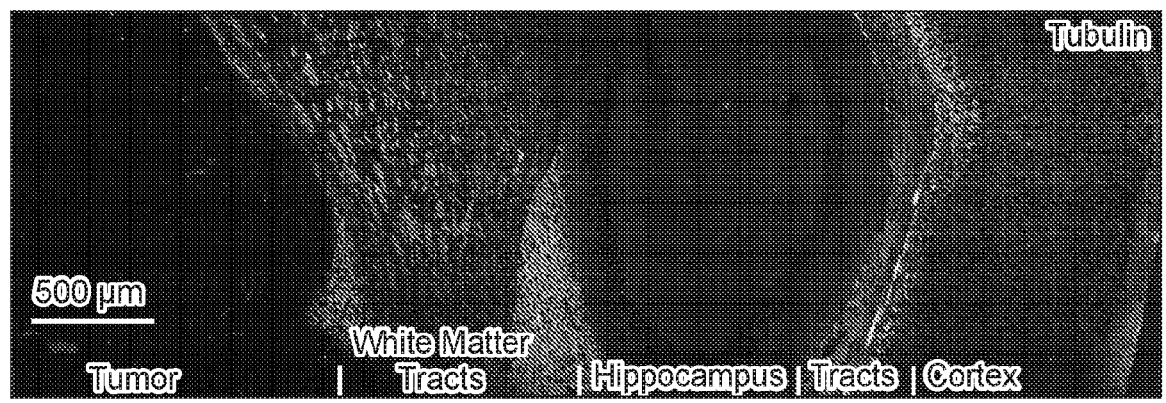
FIG. 12E illustrates the acetylated tubulin staining in cortical tissue with glioma.

As shown in FIGS. 12A-E, all the samples were obtained on 10 um paraffin sections. FIG. 12A shows the acetylated tubulin visualized using DNA conjugated anti-ac Tubulin antibody. The detection was performed using ligation amplification following phosphatase and sonicated DNA block. FIG. 12B shows that the same section after 30 min in endonuclease solution removed acetylated tubulin signal. Residual fluorescence due to auto-fluorescence of blood vessels and longer exposure times. FIG. 12C shows that the same tissue was restained using secondary antibodies. FIG. 12D shows the close-up view of the acetylated tubulin structures in the yellow boxes from FIGS. 12A and 12C. FIG. 12E shows the acetylated tubulin staining in cortical tissue with glioma. The strong staining of axon traced where stable acetylated tubulin was densest, while the undifferentiated tumor did not express this stable form of tubulin.

Example 9. DNA-Antibody for Archival Imaging

The stability of DNA (e.g., half-life of 500 years) and the ability of DNA to retain its functional characteristics even after long periods if dehydration makes DNA conjugated antibodies an ideal archival reagent for immunohistochemistry (IHC) detection. In this embodiment, the DNA conjugated antibodies is designed with a terminal restriction site that upon digestion and removal of ligated fluorescent detection oligos returns to its original sequence, thus preparing it for future archival detection. A terminal ( . . . GGG [hemi-SMA1 site]) on an antibody conjugated DNA may generate a complete SMA1 site ( . . . GGGccc . . . ) after ligation detection (FIG. 14A). After imaging and cleavage by SMA1 ( . . . GGGxccc . . . ), the antibody conjugated DNA strand returns to the original sequence with the terminal ( . . . GGG) (FIGS. 14B-14D). The DNA attached to the antibody may be double stranded. The DNA conjugated antibody may be archived in double stranded form. In another embodiment, the DNA conjugated antibody may be archived in single stranded form. Double stranded DNA may be more stable than single stranded DNA. When the archived DNA conjugated antibody is in double stranded form, the anti-sense strand may be removed upon archival retrieval before ligation detection commences for imaging. Removal of the antisense strand may occur before storage. Removal of the anti-strand may be accomplished via denaturation (chemical or heat), nickase facilitated denaturation (in which a nickase makes the antisense into shorter segments thus reducing the melting temperature), or RNA antisense (in which an RNAse can selectively remove the RNA portion of the duplex (FIG. 14E). Upon removal of the antisense, the stained tissue may be returned to the original antibody stained state, thus ready to fresh fluorescent detection (FIG. 14F).

Example 10. Signal Amplification by Branched Oligomerization

FIG. 15A-F provided examples of improved detection of nucleic acid and protein-binding reagents in biological samples by signal amplification using branched labeled nucleic acids.

FIG. 15A shows that a target molecule (e.g., target) in a sample is detected by the method described herein. The target molecule can be a protein, RNA, DNA, or other molecule or structure detected by the amplification process. The target is contacted by a detection molecule comprising a ligand that is capable of binding the target molecule. The ligand is linked to one or more single-stranded nucleic acid (e.g., tag). The tag can be DNA, RNA, unnatural derivatives of DNA or RNA, or synthetic bases that can base pair like DNA or RNA. The tag is recognized by an antisense oligomer (e.g., probe) that comprises a complementary region and overhang region. The complementary region of the tag can be hybridized to a complementary region on the tag. The probe can form a double-stranded nucleic acid with an overhang. The overhang region can allows the docking, via base paring, of a detection label (e.g., labeled detector in FIG. 15A). One or more detection label can be added via a ligation oligomerization or templated (hybridization) oligomerization. The probe can be of any length, for example, shorter than 250 bases.

FIG. 15B shows that a long probe can dock n detection label (e.g. detector . . . n detector). Detector strands can be from 3 to 150 bases. In some cases, the docking of the detectors may create a nucleic acid without a terminal overhang. In some cases, the docking of the detectors may create a terminal overhang. When present, the terminal overhang can allow for linear or branched extension or the addition of a hairpin terminal (See FIG. 15D), which may be labeled or not labeled.

FIG. 15C shows the probe can be relatively short, and a long primary detector label (e.g., primary detector) may be hybridized to the probe. And then the primary detector may be the base-paring target of multiple, labeled secondary detector strands. The primary detector, probe and tag may be labeled or not labeled.

FIG. 15D shows that instead of the addition of single-stranded oligos, a singly or multiply labeled duplex detector can be used. This duplex can be extended n times either via manual cycling or self-assembly. The terminal end of this structure can be an overhang, blunt end or hairpin.

FIG. 15E shows that instead of linear duplex detectors, n-branched detectors can be used to build an extended labeled structure. For example, a part of the sequence of a first detection label (D1) is complementary to the overhang of the probe. D1 is hybridized to the probe. A second detection label (D2) hybridizes to another part of the sequence of D1. A third detection label (D3) is complementary and hybridized to a part of D1 and D2, and thus creates branched detector. The branched detector can further be extended by binding to a fourth detection label (D4), which can be further hybridized to a fifth detection label (D5) and a sixth detection label (D6). The terminal end of this structure can be an overhang, blunt end or hairpin.

FIG. 15F shows that linear and branched detectors can be mixed in the extension of an n-branched structure. The linear detectors can be either duplexes or short or long single strands with secondary detectors as noted in FIG. 15C. This structure can be built either through cycling of units or self-assembly. The terminal end of this structure can be an overhang, blunt end or hairpin.

Example 11. Linear and Branched Duplex Ligation Oligomerization

Figure 16A:
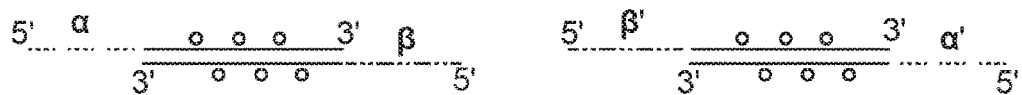
FIGS. 16A-16E illustrate examples of linear and branched duplex ligation oligomerization.

FIG. 16A-F provided examples of linear and branched duplex ligation oligomerization. A labeled linear nucleic acid module (e.g., detection label) can be ligated on one end to a double-stranded nucleic acid (e.g., formed by a single-stranded nucleic acid linked to a ligand and an antisense oligomer) that can target a molecule of interest in a sample. The labeled linear nucleic acid module can ligate on the other end to a branched duplexed nucleic acid module. The ligation can be effected by enzymatic ligation or chemical cross-linking. The linear nucleic acid module can be either duplex or single-strand nucleic acid. The linear nucleic acid module can be tagged with one or more detection tag (e.g., fluorophores). If linear nucleic acid module is single-stranded, it can be labeled by annealing one or more complementary single-stranded nucleic acid oligos that have been labeled with one or more detection tags. The linear module can be of any length and designed with either unique or complementary overhangs on both the 5' and 3' ends. If the overhangs are unique (e.g., α and β are unique ends), the linear module may not self-oligomerize (see FIG. 16A). FIG. 16A shows labeled duplexed nucleic acid units with unique complementary ends [α and α'] and [β and β']. Round dots represent labels that can be detected by a variety of modalities. Labels can include fluorescent molecules and other fluorescent entities, as well as enzymes, peptides and radioisotopes. In some cases, the number of labels per nucleic acid strand is not restricted to the number of round dots shown, as density will depend on label type and nucleic acid strand length. To achieve amplification, cycling of units can be used. If the overhangs are complementary (not shown), for example, the linear nucleic acid module has complementary ends α and α', the detection units can self-assemble.

Figure 16B:
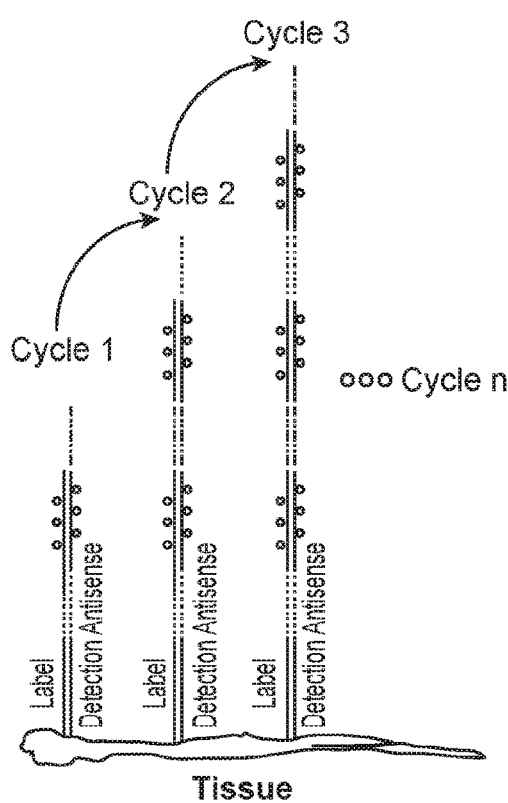

As shown in FIG. 16B, a nucleic acid-tagged structure, such as an antibody or another nucleic acid, can be detected by annealing a complementary single-stranded probe, thus forming an overhang compatible with the linear and branched labeled units. Shown in FIG. 16B is linear amplification using alternating α/β and α'/β' labeled duplex units.

Figure 16C:
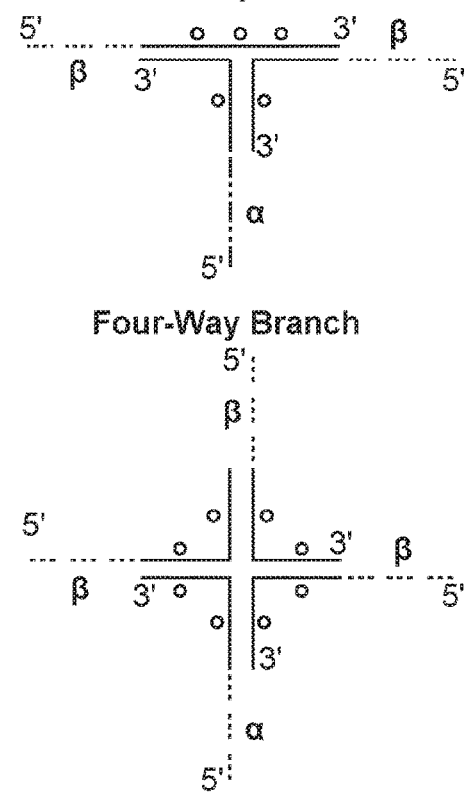

FIG. 16C shows that branched nucleic acid structures can be generated with the same unique complementary ends. Exemplary 3-way and 4-way branch structures are shown in FIG. 16C.

Figure 16D:
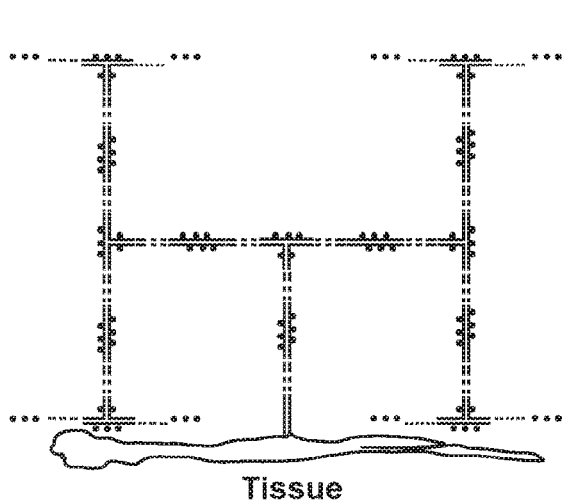

FIG. 16D shows the cycling of 3-way branches that can result in $2^y$ amplification of signal, where y=number of cycles. The shown structure can be generated by cycling alternating α/β and α'/β' labeled three-way branch units (FIG. 16C).

Figure 16E:
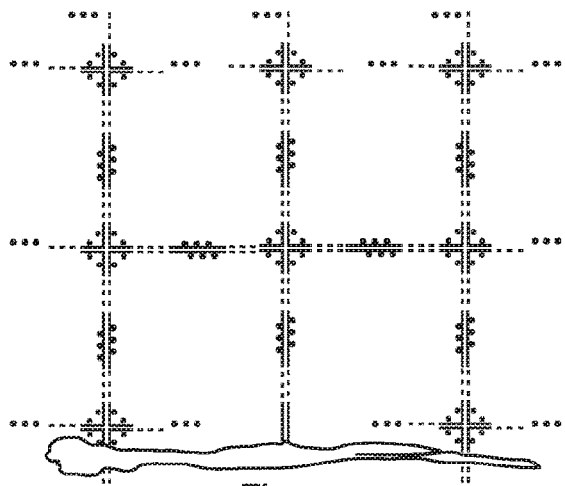

FIG. 16E shows the cycling of 4-way branches that can result in $3^y$ amplification of signal, where y=number of cycles. The shown structure can be generated by cycling alternating α/β and α'/β' labeled four-way branch units (FIG. 16C). Cycling of n branched units can provide amplification of $(n-1)^y$, where: n=the number of branches of the branch unit, and y=the number of cycles performed. The ends of branched units described in the figure can be designed with complementary ends, thus allowing the self-assembling of the structures.

Controlled sequential application of two complementary modules through serial cycling can promote oligomerization and signal amplification (FIG. 16B). 3-way, 4-way or n-way branches can be introduced within the cycling of modules to increase signal amplification (FIG. 16C-E). 3-way branches can be generated by 3 single stranded nucleic acids creating a T-structure with 3 overhangs. 4-way branches can be generated by 4 single stranded nucleic acids creating a cross structure with 4 overhangs and so on. The sequential application of branched and/or unbranched structures can allow exponential amplification of signal dictated by the number of oligomerization cycles that can be represented by the formula: $(n-1)^y$, where: n=the number of branches of the branch unit, and y=the number of cycles performed.

Moreover, the branched nucleic acid structures can be designed with endonuclease sites or labels with cleavable linkers, either of which can be used for the subsequent removal of the detection tag (e.g., fluorescent moieties). This can allow serial application, detection and removal of labeled nucleic acid structures for highly multiplexed identification of proteins and/or nucleic acids in tissue samples. Furthermore, the branched and linear detector units, as described here, can have complementary ends, such that it can allow the self-assembling of described structures.

Example 12. Branched Amplification of in In Situ Nucleic Acids Detection

Figure 17A:
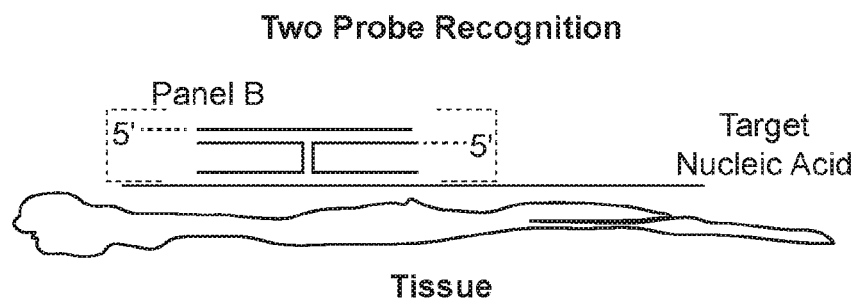
FIGS. 17A-17C illustrate examples of branched amplification of in in situ nucleic acids detection.
Figure 17B:
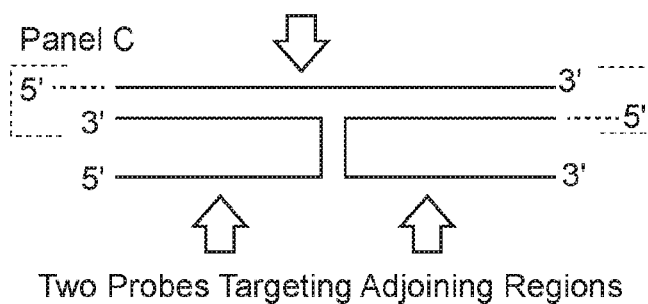
Figure 17C:
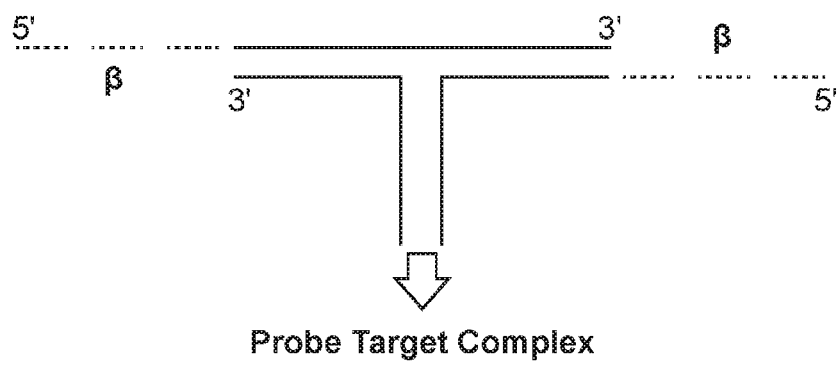

The branched detection method can be used to detect nucleic acids in tissue (FIG. 17A-17C). In this application, two specific recognition probes can target adjacent sequences in a target nucleic acid (FIG. 17A). The probes can have a complementary region whereby nucleic acid hybridization can bring the two molecules together if they are in close proximity (FIG. 17A). In this example, two adjacent nucleic acid probes generate a stem hairpin structure upon which a secondary probe can hybridize. Furthermore, FIG. 17B-17C show that the two probes can have two unique sequences that can be recognized by a secondary single stranded nucleic acid probe where upon hybridization to the adjoining probes can generate a 3-way branched structure that can be the initiation point of branched oligomerization as described above (FIG. 16C-D).

Example 13. Branched Oligomerization Greatly Amplifies the Signal in Formalin-Fixed Paraffin Embedded (FFPE) Tissue FIG. 18A-18F shows exemplary images of 5 μm-thick sections of FFPE mouse brain cortex labelled with a DNA-tagged anti-acetylated tubulin primary antibody. The primary antibody was detected with an alexa-594 labelled secondary antibody (FIG. 18A) or branched oligomerization (FIG. 18B-18F). Tissues were incubated with a detector probe complementary to the tag, and then with cycles of branched "T" and alexa-594-labelled linear detectors through two (FIG. 18B), four (FIG. 18C), six (FIG. 18D), eight (FIG. 18E) or ten (FIG. 18F) cycles, where a cycle comprises one "T" and one linear detector ligation reaction. Main images are shown at identical exposure and contrast; insets show a sub-region of each at optimum contrast settings.

Figure 18A:
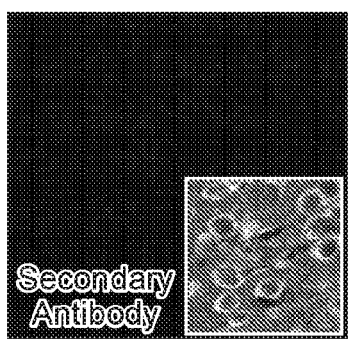
FIGS. 18A-18I illustrate that branched oligomerization greatly amplifies the signal in formalin-fixed paraffin embedded (FFPE) tissue.
Figure 18B:
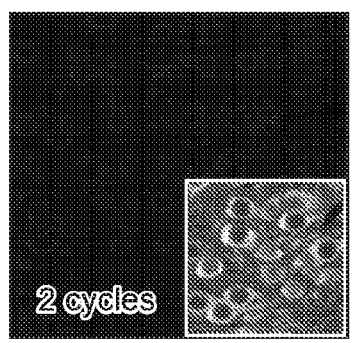
Figure 18C:
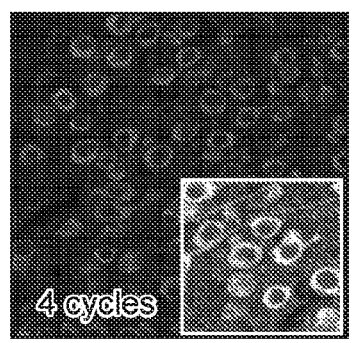
Figure 18D:
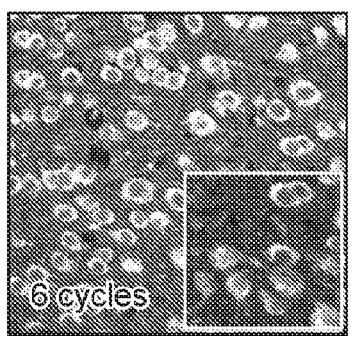
Figure 18E:
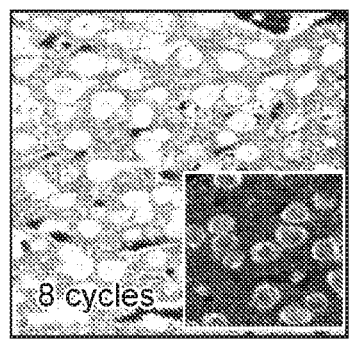
Figure 18F:
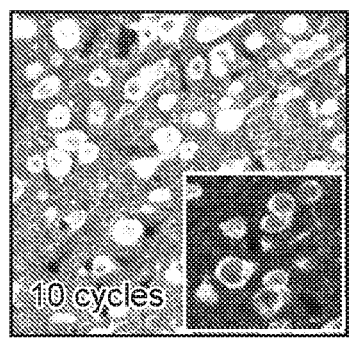
Figure 18G:
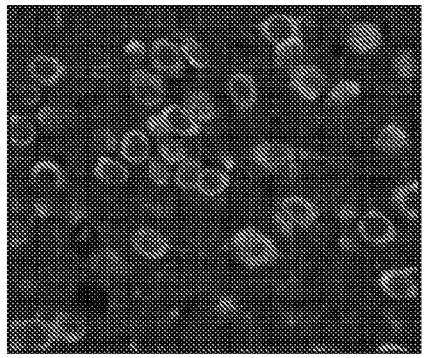
Figure 18H:
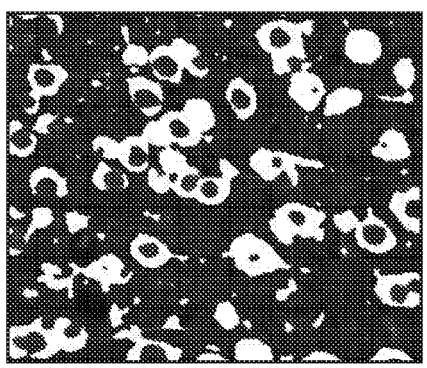
Figure 18I:
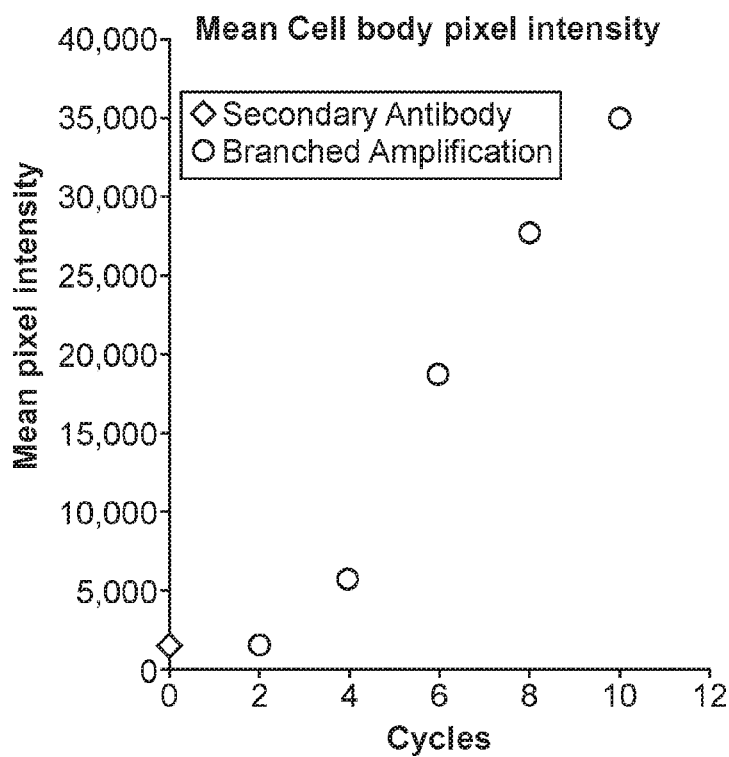

FIG. 18G shows example of 6-cycle amplification with an overlay of a cell body mask (white regions in FIG. 18H). FIG. 18I shows the mean pixel intensity for pixels Within the cell body mask for secondary antibody (diamond) and 2-10 cycles of branched oligomerization (circles). Masks were created using the staining pattern of a fluorescent secondary antibody in a different channel (Alexa 647). Overall, the branched oligomerization example demonstrated the signal amplification as the number of cycle increases.

Figure 19A:
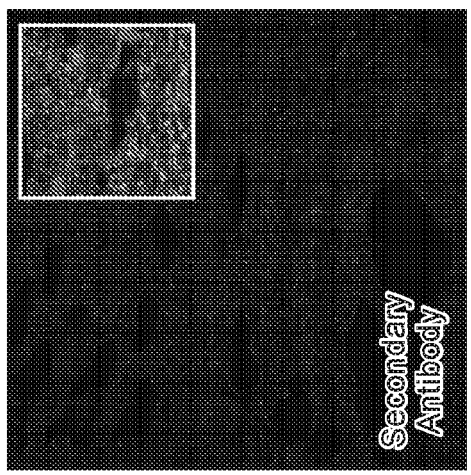
FIGS. 19A-19F illustrate exemplary images of 70 nm-thick sections of mouse brain cortex labelled with a DNA-tagged anti-acetylated tubulin primary antibody, imaged at 63×/1.4 NA under oil immersion.
Figure 19B:
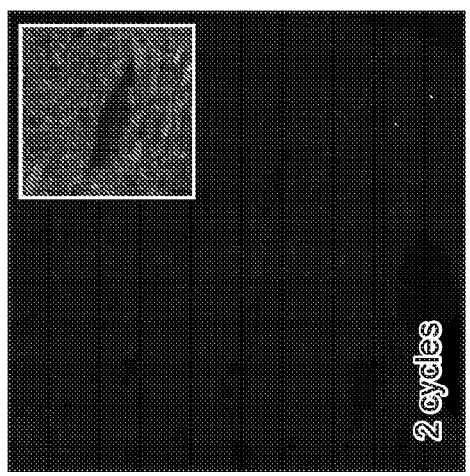
Figure 19C:
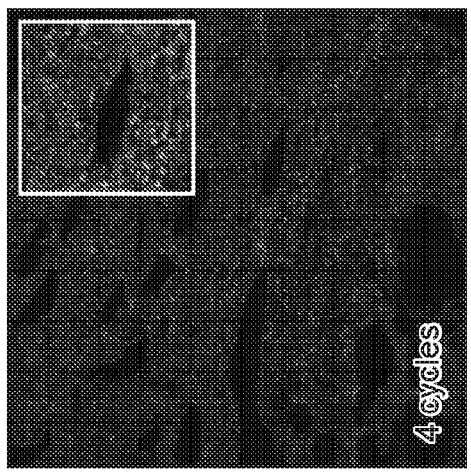
Figure 19D:
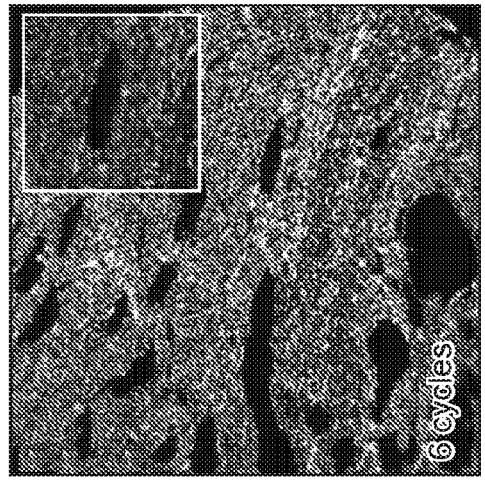
Figure 19E:
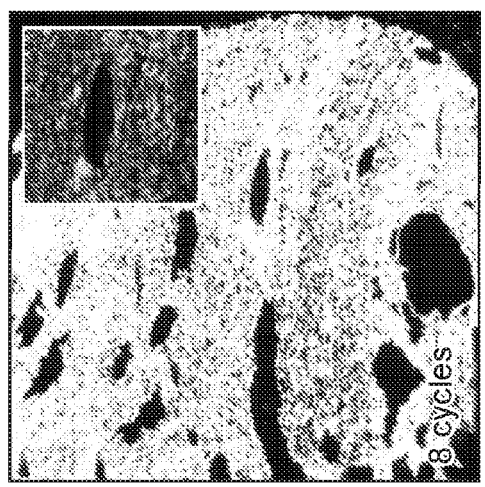
Figure 19F:
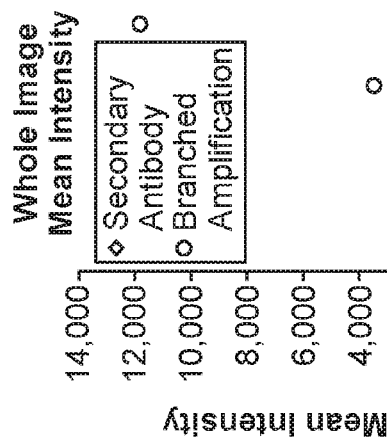

Example 14. Branched Oligomerization Greatly Amplifies the Signal in Resin-Embedded Tissue FIG. 19A-19F shows exemplary images of 70 nm-thick sections of mouse brain cortex labelled with a DNA-tagged anti-acetylated tubulin primary antibody, imaged at 63×/1.4 NA under oil immersion. The primary antibody was detected with an alexa-594 labelled secondary antibody (FIG. 19A) or branched oligomerization (FIG. 19B-19E). Tissues were incubated with a detector probe complementary to the tag, and then with cycles of branched "T" and alexa-594-labelled linear detectors through two (FIG. 19B), four (FIG. 19C), six (FIG. 19D), or eight (FIG. 19E) cycles, where a cycle comprises one "T" and one linear detector ligation reaction. Main images are shown at identical exposure and contrast. Insets show a sub-region of each at optimum contrast settings, centered on the same blood vessel, with DAPI stained nuclei in blue, and tubulin immunofluorescence in green. FIG. 19F shows the mean image intensity (grey value from the 16-bit image) for secondary antibody (diamond) and 2-8 cycles of branched oligomerization (circles).

What is claimed is:

1. A composition that comprises:
 - a detection molecule and an antisense oligomer, wherein the detection molecule comprises: i) a ligand that binds a target molecule in a sample; and ii) a single-stranded nucleic acid linked to the ligand, and wherein the single-stranded nucleic acid is capable of hybridizing to the antisense oligomer to form a double-stranded nucleic acid that has an overhang comprising one or more unpaired nucleotides in the single-stranded nucleic acid or the antisense oligomer, and
 - a branched detector that is a double-stranded DNA and comprises at least three overhangs: one overhang for in situ ligation with the double-stranded nucleic acid; and two or more overhangs for in situ ligation with two or more linear detectors, and
 - wherein at least one of the linear detectors comprises a detection tag.

2. The composition of claim 1, wherein the ligand is an antibody, or wherein the target molecule is a protein.

3. The composition of claim 1, wherein the overhang of the double-stranded nucleic acid or the overhangs of the branched detector independently comprise at least: 5, 10, 15, 20, 25, or 30 nucleotides.

4. The composition of claim 1, wherein the composition comprises a plurality of the detection molecules.

5. The composition of claim 4, wherein each of the plurality of detection molecules binds a different target molecule.

6. The composition of claim 1, wherein the sample is an intact tissue sample.

7. The composition of claim 1 that further comprises a DNA ligase.

8. The composition of claim 1, wherein the detection tag comprises a fluorophore.

9. The composition of claim 8, wherein the fluorophore comprises coumarin, rhodamine, xanthene, fluorescein, or cyanine.

10. The composition of claim 1, wherein the one overhang of the branched detector is linked to the overhang of the double-stranded nucleic acid by direct hybridization.

11. The composition of claim 1, wherein the branched detector comprises a multi-way branch.

12. The composition of claim 11, wherein the multi-way branch is a three-way branch or a four-way branch.

13. The composition of claim 11, wherein the multi-way branch has a T-structure with 3 overhangs, or a cross structure with 4 overhangs.

14. The composition of claim 11, wherein the composition comprises a complex generated by cycling of the multi-way branches.

15. The composition of claim 14, wherein a number of the cycling is from 2 to 10.

16. The composition of claim 14, wherein the cycling comprises a sequential application of the multi-way branch and then the linear detectors.

17. A kit that comprises the detection molecule, the antisense oligomer, the branched detector and the linear detector of claim 1.

18. A method, comprising contacting the target molecule with the detection molecule, the antisense oligomer, the branched detector and the linear detector of claim 1.

19. A composition that comprises:
 - a detection molecule, wherein the detection molecule comprises: i) an antibody that binds a target protein, and ii) a single-stranded nucleic acid linked to the antibody;
 - an antisense oligomer, wherein the antisense oligomer is capable of hybridizing to the single-stranded nucleic acid to form a double-stranded nucleic acid that has an overhang comprising one or more unpaired nucleotides in the single-stranded nucleic acid or the antisense oligomer; and
 - a branched detector that is a double-stranded DNA and comprises at least three overhangs: one overhang for in situ ligation with the double-stranded nucleic acid; and two or more overhangs for in situ ligation with two or more linear detectors, and wherein at least one of the linear detectors comprises a detection tag.

20. The composition of claim 19, wherein the branched detector has no detection tag.

21. The composition of claim 1, wherein the target molecule is a protein.

22. The composition of claim 1, wherein the target molecule is a cell surface protein.

23. The method of claim 18, further comprising a sequential application of contacting the target molecule with the linear detectors after contacting the target molecule with the branched detector.

24. The method of claim 23, wherein the sequential application is repeated by a number of cycles.

25. The method of claim 24, wherein the number of the cycles is from 2 to 10.

26. The method of claim 24, wherein the branched detector is ligated with the linear detectors in the cycle.

27. The method of claim 24, wherein the branched detector is ligated with the linear detectors after the cycle.

* * * * *

SEQUENCE LISTING

<160> NUMBER OF SEQ ID NOS: 3

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1
atctgactac a                                                           11

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gactgactga ctgactgact                                                  20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agtcagtcag tcagtcagt                                                   19
```